US012559509B1

(12) United States Patent
Dickson et al.

(10) Patent No.: US 12,559,509 B1
(45) Date of Patent: Feb. 24, 2026

(54) CITRATE COORDINATION COMPLEX OF AN ORALLY-DELIVERED BETA-LACTAMASE INHIBITOR AND USES THEREOF

(71) Applicant: Venatorx Pharmaceuticals, Inc., Malvern, PA (US)

(72) Inventors: David P. Dickson, Merion Station, PA (US); Anthony Drager, Thorndale, PA (US); Gopinath Rongala, Malvern, PA (US); Allison L. Zulli, Chesterbrook, PA (US)

(73) Assignee: Venatorx Pharmaceuticals, Inc., Malvern, PA (US)

( * ) Notice: Subject to any disclaimer, the term of this patent is extended or adjusted under 35 U.S.C. 154(b) by 0 days.

(21) Appl. No.: 19/079,297

(22) Filed: Mar. 13, 2025

Related U.S. Application Data

(63) Continuation of application No. PCT/US2024/056643, filed on Nov. 20, 2024.

(60) Provisional application No. 63/601,661, filed on Nov. 21, 2023.

(51) Int. Cl.
*C07F 5/02* (2006.01)
*A61K 9/48* (2006.01)
*A61K 31/546* (2006.01)
*A61K 31/69* (2006.01)

(52) U.S. Cl.
CPC .............. *C07F 5/025* (2013.01); *A61K 9/485* (2013.01); *A61K 9/4858* (2013.01); *A61K 9/4866* (2013.01); *A61K 31/546* (2013.01); *A61K 31/69* (2013.01); *C07B 2200/13* (2013.01)

(58) Field of Classification Search
CPC ....... C07F 5/025; A61K 9/485; A61K 9/4858; A61K 9/4866; A61K 31/546; A61K 31/69; C07B 2200/13
See application file for complete search history.

(56) References Cited

U.S. PATENT DOCUMENTS

| | | | |
|---|---|---|---|
| 7,271,186 | B1 | 9/2007 | Shoichet et al. |
| 9,040,504 | B2 | 5/2015 | Burns et al. |
| 9,637,504 | B2 | 5/2017 | Burns et al. |
| 9,783,555 | B2 | 10/2017 | Burns et al. |
| 9,926,336 | B2 | 3/2018 | Burns et al. |
| 11,008,346 | B2 | 5/2021 | Burns et al. |
| 2010/0292185 | A1 | 11/2010 | Burns et al. |
| 2015/0291630 | A1 | 10/2015 | Burns et al. |
| 2015/0361107 | A1 | 12/2015 | Trout |
| 2017/0342092 | A1 | 11/2017 | Burns et al. |
| 2018/0002351 | A1 | 1/2018 | Hecker et al. |
| 2022/0125812 | A1 | 4/2022 | Burns et al. |
| 2022/0194964 | A1 | 6/2022 | Burns et al. |

FOREIGN PATENT DOCUMENTS

| | | | |
|---|---|---|---|
| WO | WO-2010056827 | A1 | 5/2010 |
| WO | WO-2010130708 | A1 | 11/2010 |
| WO | WO-2013092979 | A1 | 6/2013 |
| WO | WO-2014107536 | A1 | 7/2014 |
| WO | WO-2014151958 | A1 | 9/2014 |
| WO | WO-2015191907 | A1 | 12/2015 |
| WO | WO-2020112542 | A1 | 6/2020 |
| WO | WO-2020205932 | A1 | 10/2020 |
| WO | WO-2025111328 | A1 | 5/2025 |

OTHER PUBLICATIONS

Trout, J. Med. Chem. 2021, 64, 10155-10166 (Year: 2021).*
Streck, Streck, Ambler Classification of β-lactamase, published 2020, url=https://www.streck.com/blog/ambler-classification-of-%CE% B2-lactamases, accessed Jul. 7, 2025 (Year: 2020).*
Bauernfeind, Review of Infectious Disease, vol. 8, Supp. 5, 1986 (Year: 1986).*
Co-Pending PCT Application No. PCT/US2024/056643, inventors Dickson, David et al., filed on Nov. 24, 2011.
PCT/US2015/035407 International Search Report and Written Opinion dated Oct. 20, 2015.
PCT/US2019/062798 International Search Report and Written Opinion dated Jan. 27, 2020.
PCT/US2020/026114 International Search Report and Written Opinion dated Jul. 23, 2020.
PCT/US2024/056643 International Search Report and Written Opinion dated Feb. 4, 2025.
Rautio, Jarkko. et al. Prodrugs—Recent approvals and a glimpse of the pipeline. European Journal of Pharmaceutical Sciences 109:146-161 (2017).
Trout, Robert E. et al. Discovery of VNRX-7145 (VNRX-5236 etzadroxil): an orally bioavailable β-lactamase inhibitor for Enterobacterales expressing Ambler class A, C, and D enzymes. Journal of medicinal chemistry 64(14):10155-10166 (2021).

* cited by examiner

*Primary Examiner* — Susanna Moore
*Assistant Examiner* — Luisalberto Gonzalez
(74) *Attorney, Agent, or Firm* — WILSON SONSINI GOODRICH & ROSATI

(57) ABSTRACT

Disclosed herein is a compound that is (R)-(2-(3-((((2-ethylbutanoyl)oxy)methoxy)carbonyl)-2-hydroxyphenyl)-1-propionamidoethyl)boronic acid citrate coordination complex, or a pharmaceutically acceptable salt or solvate thereof. Also disclosed herein are methods of treating a bacterial with a compound that is (R)-(2-(3-((((2-ethylbutanoyl)oxy)methoxy)carbonyl)-2-hydroxyphenyl)-1-propionamidoethyl)boronic acid citrate coordination complex, or a pharmaceutically acceptable salt or solvate thereof in combination with ceftibuten.

22 Claims, 12 Drawing Sheets

Compound 1 citrate coordination complex

Ceftibuten (in citrate FDC)

Compound 1 ethanolate

Ceftibuten (in ethanolate FDC)

Compound 1 ethanolate capsules

Ceftibuten capsules

Ceftibuten FDC

Compound 1 citrate coordination complex FDC

CITRATE COORDINATION COMPLEX OF AN ORALLY-DELIVERED BETA-LACTAMASE INHIBITOR AND USES THEREOF

CROSS-REFERENCE

This patent application is a continuation of International Application No. PCT/US2024/056643, filed Nov. 20, 2024, which claims the benefit of U.S. Provisional Application Ser. No. 63/601,661 filed Nov. 21, 2023; which are hereby incorporated by reference in their entirety.

STATEMENT AS TO FEDERALLY SPONSORED RESEARCH

This invention was made with government support under Contract number HHSN272201600029C awarded by the National Institutes of Health (NIH). The government has certain rights in the invention.

BACKGROUND OF THE INVENTION

Antibiotics are the most effective drugs for treating bacterial infectious diseases. They are largely used in the clinic because of their good antibacterial effect with limited side effects. Among them, the beta-lactam class of antibiotics (for example, penicillins, cephalosporins, monobactams and carbapenems) are preferred because their effect is bactericidal, and their target is absent in eukaryotic cells with consequent low toxicity.

To counter the efficacy of the various beta-lactams, bacteria have evolved to produce variants of beta-lactam deactivating enzymes called beta-lactamases, and in the ability to share this tool both vertically and horizontally inter- and intra-species. These beta-lactamases are categorized as "serine" or "metallo" based, respectively, based on the presence of a key serine or zinc in the enzyme active site. The rapid induction, selection and spread of this mechanism of bacterial resistance can severely limit the whole class of beta-lactam treatment options in the hospital and in the community. There is a need for stable, effective, and safe therapeutic agents, combining a beta-lactam antibiotic and a beta-lactamase inhibitor, that can treat such resistant infections. There is also a need for such a therapeutic agent that can be formulated into a stable immediate release tablet.

SUMMARY OF THE INVENTION

Disclosed herein is a compound that is (R)-(2-(3-((((2-ethylbutanoyl)oxy)methoxy)carbonyl)-2-hydroxyphenyl)-1-propionamidoethyl)boronic acid citrate coordination complex:

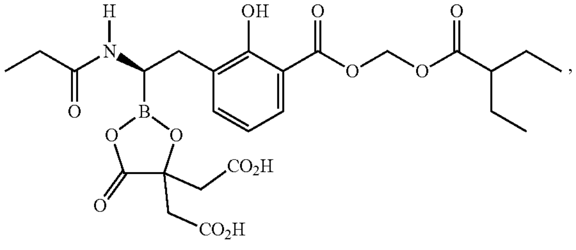 [SMILES: CCC(=O)N[C@@H](Cc1cccc(C(=O)OCOC(=O)C(CC)CC)c1O)B1OC(=O)C(CC(=O)O)(CC(=O)O)O1]

or a pharmaceutically acceptable salt or solvate thereof.

Also disclosed herein is a crystalline form of a compound that is (R)-(2-(3-((((2-ethylbutanoyl)oxy)methoxy)carbonyl)-2-hydroxyphenyl)-1-propionamidoethyl)boronic acid citrate coordination complex:

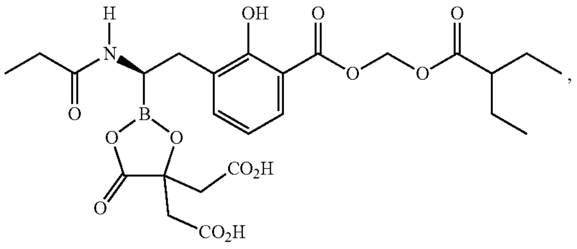 [SMILES: CCC(=O)N[C@@H](Cc1cccc(C(=O)OCOC(=O)C(CC)CC)c1O)B1OC(=O)C(CC(=O)O)(CC(=O)O)O1]

or a pharmaceutically acceptable salt or solvate thereof.

Also disclosed herein is a pharmaceutical composition comprising:

(i) a compound that is (R)-(2-(3-((((2-ethylbutanoyl)oxy)methoxy)carbonyl)-2-hydroxyphenyl)-1-propionamidoethyl)boronic acid citrate coordination complex:

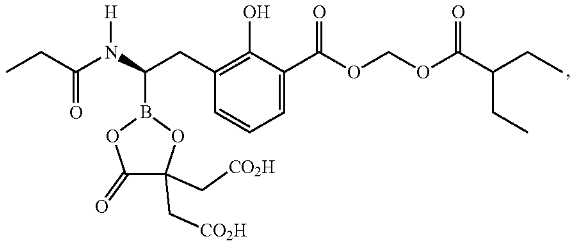 [SMILES: CCC(=O)N[C@@H](Cc1cccc(C(=O)OCOC(=O)C(CC)CC)c1O)B1OC(=O)C(CC(=O)O)(CC(=O)O)O1]

or a pharmaceutically acceptable salt or solvate thereof; and (ii) ceftibuten.

In some embodiments, ceftibuten is in the form of ceftibuten dihydrate.

In some embodiments, the compound is (R)-(2-(3-((((2-ethylbutanoyl)oxy)methoxy)carbonyl)-2-hydroxyphenyl)-1-propionamidoethyl)boronic acid citrate coordination complex:

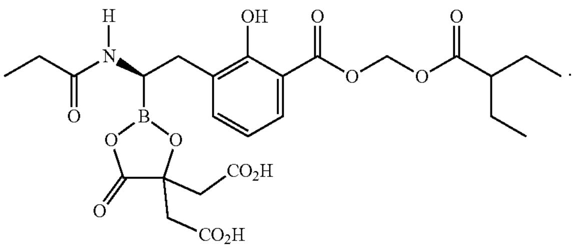 [SMILES: CCC(=O)N[C@@H](Cc1cccc(C(=O)OCOC(=O)C(CC)CC)c1O)B1OC(=O)C(CC(=O)O)(CC(=O)O)O1]

Also disclosed herein is a pharmaceutical composition comprising:

(i) a crystalline form of a compound that is (R)-(2-(3-((((2-ethylbutanoyl)oxy)methoxy)carbonyl)-2-hydroxyphenyl)-1-propionamidoethyl)boronic acid citrate coordination complex:

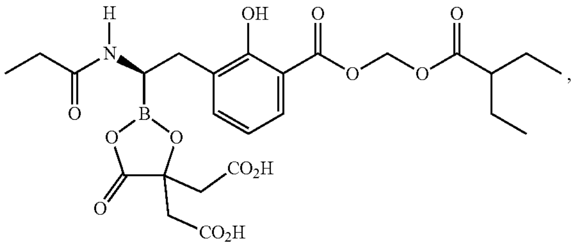

or a pharmaceutically acceptable salt solvate thereof; and (ii) ceftibuten.

In some embodiments, ceftibuten is in the form of ceftibuten dihydrate.

In some embodiments, the compound and ceftibuten are formulated in a single dosage form.

In some embodiments, the crystalline form and ceftibuten are formulated in a single dosage form.

In some embodiments, the single dosage form is a capsule.

Also disclosed herein is a method of treating a bacterial infection in a subject, the method comprising administering to the subject a pharmaceutical composition disclosed herein.

In some embodiments, the bacterial infection is caused by carbapenem-resistant Enterobacteriaceae (CRE) or extended-spectrum beta-lactamase (ESBL) producing gram-negative bacteria.

In some embodiments, the bacterial infection is acute bacterial exacerbations of chronic bronchitis (ABECB), acute bacterial otitis media, pharyngitis, or tonsillitis.

In some embodiments, the bacterial infection is pneumonia, urinary tract infections, enteritis, or gastroenteritis.

In some embodiments, the bacterial infection is otitis media, strep throat, pneumonia, urinary tract infections, gonorrhea, or Lyme disease.

DETAILED DESCRIPTION

Figure 1:
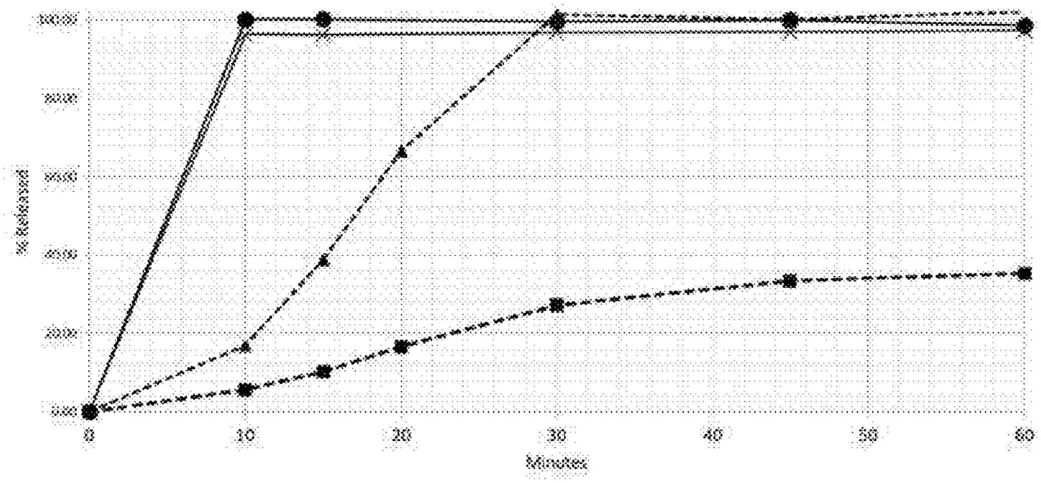
FIG. 1 shows the dissolution profile comparison of fixed dose capsule prototypes of ceftibuten dihydrate combined with either compound 1 ethanolate complex or compound 1 citrate coordination complex.

The challenge for the development of a solid oral dosage form comprising a fixed dose combination (FDC) of ceftibuten and a prodrug for oral delivery of (R)-2-hydroxy-3-propionamido-3,4-dihydro-2H-benzo[e][1,2]oxaborinine-8-carboxylic acid is to find a prodrug and solid form of (R)-2-hydroxy-3-propionamido-3,4-dihydro-2H-benzo[e][1,2]oxaborinine-8-carboxylic acid that is stable when combined with ceftibuten while providing the desired immediate release dissolution profile and oral bioavailability.

Definitions

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Oxo" refers to =O.

"Amine" refers to $-NH_2$.

"Hydroxyl" refers to —OH.

"Carboxyl" refers to —COOH.

"Alkyl" refers to a straight-chain or branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl. In some embodiments, the alkyl is a $C_1$-$C_6$ alkyl. In some embodiments, the alkyl is a $C_1$-$C_5$ alkyl. In some embodiments, the alkyl is a $C_1$-$C_4$ alkyl. In some embodiments, the alkyl is a $C_1$-$C_3$ alkyl. Unless stated otherwise specifically in the specification, an alkyl group may be optionally substituted, for example, with one or more oxo, halogen, amino, nitrile, nitro, hydroxyl, haloalkyl, alkoxy, carboxyl, carboxylate, aryl, cycloalkyl, heterocycloalkyl, or heteroaryl, and the like. In some embodiments, the alkyl is optionally substituted with one or more oxo, halogen, —CN, —COOH, —COOMe, —OH, —OMe, —$NH_2$, or —$NO_2$. In some embodiments, the alkyl is optionally substituted with one or more halogen, —CN, —OH, or —OMe. In some embodiments, the alkyl is optionally substituted with halogen.

"Alkenyl" refers to a straight-chain or branched-chain hydrocarbon monoradical having one or more carbon-carbon double-bonds and having from two to about ten carbon atoms, more preferably two to about six carbon atoms. The group may be in either the cis or trans or Z or E conformation about the double bond(s), and should be understood to include both isomers. Examples include, but are not limited to ethenyl (—CH=$CH_2$), 1-propenyl (—$CH_2$CH=$CH_2$), isopropenyl [—C($CH_3$)=$CH_2$], butenyl, 1,3-butadienyl and the like. Whenever it appears herein, a numerical range such as "$C_2$-$C_6$ alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkenyl is optionally substituted with one or more oxo, halogen, —CN, —COOH, —COOMe, —OH, —OMe, —$NH_2$, or —$NO_2$. In some embodiments, the alkenyl is optionally substituted with one or more halogen, —CN, —OH, or —OMe. In some embodiments, the alkenyl is optionally substituted with halogen.

"Alkynyl" refers to a straight-chain or branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "$C_2$-$C_6$ alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkynyl is optionally substituted with one or more oxo, halogen, —CN, —COOH, —COOMe, —OH, —OMe, —$NH_2$, or —$NO_2$. In some embodiments, the alkynyl is optionally substituted with one or more halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkylene is optionally substituted with one or more oxo, halogen, —CN, —COOH, —COOMe, —OH, —OMe, —$NH_2$, or —$NO_2$. In some embodiments, the alkylene is optionally substituted with one or more halogen, —CN, —OH, or —OMe. In some embodiments, the alkylene is optionally substituted with halogen.

"Alkoxy" refers to a radical of the formula —O-alkyl where alkyl is defined as above. Unless stated otherwise specifically in the specification, an alkoxy group may be optionally substituted, for example, with one or more oxo, halogen, amino, nitrile, nitro, hydroxyl, alkyl, haloalkyl, alkoxy, carboxyl, carboxylate, aryl, cycloalkyl, heterocycloalkyl, or heteroaryl, and the like. In some embodiments, the alkoxy is optionally substituted with one or more halogen, —CN, —COOH, —COOMe, —OH, —OMe, —$NH_2$, or —$NO_2$. In some embodiments, the alkoxy is optionally substituted with one or more halogen, —CN, —OH, or —OMe. In some embodiments, the alkoxy is optionally substituted with halogen.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl include, for example, aminomethyl, aminoethyl, aminopropyl, aminobutyl, or aminopentyl. In some embodiments, the aminoalkyl is aminomethyl.

"Aryl" refers to a radical derived from a hydrocarbon ring system comprising 6 to 30 carbon atoms and at least one aromatic ring. The aryl radical may be a monocyclic, bicyclic, tricyclic, or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to anthracenyl, naphthyl, phenanthrenyl, azulenyl, phenyl, chrysenyl, fluoranthenyl, fluorenyl, as-indacenyl, s-indacenyl, indanyl, indenyl, phenalenyl, phenanthrenyl, pleiadenyl, pyrenyl, and triphenylenyl. Unless stated otherwise specifically in the specification, an aryl may be optionally substituted, for example, with one or more halogen, amino, nitrile, nitro, hydroxyl, alkyl, alkenyl, alkynyl, haloalkyl, alkoxy, carboxyl, carboxylate, aryl, cycloalkyl, heterocycloalkyl, or heteroaryl, and the like. In some embodiments, the aryl is optionally substituted with one or more halogen, methyl, ethyl, —CN, —COOH, —COOMe, —$CF_3$, —OH, —OMe, —$NH_2$, or —$NO_2$. In some embodiments, the aryl is optionally substituted with one or more halogen, methyl, ethyl, —CN, —$CF_3$, —OH, or —OMe. In some embodiments, the aryl is optionally substituted with halogen.

"Cycloalkyl" refers to a partially or fully saturated, monocyclic, or polycyclic carbocyclic ring, which may include fused (when fused with an aryl or a heteroaryl ring, the cycloalkyl is bonded through a non-aromatic ring atom), spiro, and/or bridged ring systems. In some embodiments, the cycloalkyl is fully saturated. Representative cycloalkyls include, but are not limited to, cycloalkyls having from three to fifteen carbon atoms (e.g., $C_3$-$C_{15}$ fully saturated cycloalkyl or $C_3$-$C_{15}$ cycloalkenyl), from three to ten carbon atoms (e.g., $C_3$-$C_{10}$ fully saturated cycloalkyl or $C_3$-$C_{10}$ cycloalkenyl), from three to eight carbon atoms (e.g., $C_3$-$C_8$ fully saturated cycloalkyl or $C_3$-$C_8$ cycloalkenyl), from three to six carbon atoms (e.g., $C_3$-$C_6$ fully saturated cycloalkyl or $C_3$-$C_6$ cycloalkenyl), from three to five carbon atoms (e.g., $C_3$-$C_5$ fully saturated cycloalkyl or $C_3$-$C_5$ cycloalkenyl), or three to four carbon atoms (e.g., $C_3$-$C_4$ fully saturated cycloalkyl or $C_3$-$C_4$ cycloalkenyl). In some embodiments, the cycloalkyl is a 3- to 10-membered fully saturated cycloalkyl or a 3- to 10-membered cycloalkenyl. In some embodiments, the cycloalkyl is a 3- to 6-membered fully saturated cycloalkyl or a 3- to 6-membered cycloalkenyl. In some embodiments, the cycloalkyl is a 5- to 6-membered fully saturated cycloalkyl or a 5- to 6-membered cycloalkenyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octyl, bicyclo[4.3.0]nonyl, cis-decalinyl, trans-decalinyl, bicyclo [2.1.1]hexyl, bicyclo[2.2.1]heptyl, bicyclo[2.2.2]octyl, bicyclo[3.2.1]octyl, bicyclo[3.2.2]nonyl, and bicyclo[3.3.2] decyl, bicyclo[1.1.1]pentyl, bicyclo[3.1.0]hexyl, bicyclo [3.1.1]heptyl, 7,7-dimethyl-bicyclo[2.2.1]heptanyl, Spiro [4.2]heptyl, spiro[4.3]octyl, spiro[5.2]octyl, spiro[3.3] heptyl, and spiro[5.3]nonyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with one or more oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, or heteroaryl, and the like. In some embodiments, a cycloalkyl is optionally substituted with one or more oxo, halogen, methyl, ethyl, —CN, —COOH, —COOMe, —$CF_3$, —OH, —OMe, —$NH_2$, or —$NO_2$. In some embodiments, a cycloalkyl is optionally substituted with one or more oxo, halogen, methyl, ethyl, —CN, —$CF_3$, —OH, or —OMe. In some embodiments, the cycloalkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 2-fluoroethyl, 3-bromo-2-fluoropropyl, 1,2-dibromoethyl, and the like.

"Haloalkoxy" refers to —O-haloalkyl, with haloalkyl as defined above.

"Hydroxyalkyl" refers to an alkyl radical, as defined above, that is substituted by one or more hydroxyls. In some embodiments, the alkyl is substituted with one hydroxyl. In some embodiments, the alkyl is substituted with one, two, or three hydroxyls. Hydroxyalkyl includes, for example, hydroxymethyl, hydroxyethyl, hydroxypropyl, hydroxybutyl, or hydroxypentyl. In some embodiments, the hydroxyalkyl is hydroxymethyl.

"Aminoalkyl" refers to an alkyl radical, as defined above, that is substituted by one or more amines. In some embodiments, the alkyl is substituted with one amine. In some embodiments, the alkyl is substituted with one, two, or three amines. Aminoalkyl includes, for example, aminomethyl, aminoethyl, aminopropyl, aminobutyl, or aminopentyl. In some embodiments, the aminoalkyl is aminomethyl.

"Deuteroalkyl" refers to an alkyl radical, as defined above, that is substituted by one or more deuteriums. In some embodiments, the alkyl is substituted with one deuterium. In some embodiments, the alkyl is substituted with one, two, or three deuteriums. In some embodiments, the alkyl is substituted with one, two, three, four, five, or six deuteriums. Deuteroalkyl includes, for example, $CD_3$, $CH_2D$, $CHD_2$, $CH_2CD_3$, $CD_2CD_3$, $CHDCD_3$, $CH_2CH_2D$, or $CH_2CHD_2$. In some embodiments, the deuteroalkyl is $CD_3$.

"Heteroalkyl" refers to an alkyl group in which one or more skeletal atoms of the alkyl are selected from an atom other than carbon, e.g., oxygen, nitrogen, sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen, sulfur, phosphorus, or combinations thereof wherein the heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or two atoms selected from the group consisting of oxygen, nitrogen, and sulfur wherein the heteroalkyl is attached to the rest of the molecule at a carbon atom of the heteroalkyl. Examples of such heteroalkyl are, for example, —$CH_2OCH_3$, —$CH_2CH_2OCH_3$, —$CH_2CH_2OCH_2CH_2OCH_3$, —$CH(CH_3)OCH_3$, —$CH_2NHCH_3$, —$CH_2N(CH_3)_2$, —$CH_2CH_2NHCH_3$, or —$CH_2CH_2N(CH_3)_2$. Unless stated otherwise specifically in the specification, a heteroalkyl is optionally substituted for example, with one or more oxo, halogen, amino, nitrile, nitro, hydroxyl, alkyl, alkenyl, alkynyl, haloalkyl, alkoxy, aryl, cycloalkyl, heterocycloalkyl, or heteroaryl, and the like. In some embodiments, a heteroalkyl is optionally substituted with one or more oxo, halogen, methyl, ethyl, —CN, —$CF_3$, —OH, —OMe, —$NH_2$, or —$NO_2$. In some embodiments, a heteroalkyl is optionally substituted with one or more oxo, halogen, methyl, ethyl, —CN, —$CF_3$, —OH, or —OMe. In some embodiments, the heteroalkyl is optionally substituted with halogen.

"Heterocycloalkyl" refers to a 3- to 24-membered partially or fully saturated ring radical comprising 2 to 23 carbon atoms and from one to 8 heteroatoms selected from the group consisting of nitrogen, oxygen, phosphorous, silicon, and sulfur. In some embodiments, the heterocycloalkyl is fully saturated. In some embodiments, the heterocycloalkyl is C-linked. In some embodiments, the heterocycloalkyl is N-linked. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic, or tetracyclic ring system, which may include fused (when fused with an aryl or a heteroaryl ring, the heterocycloalkyl is bonded through a non-aromatic ring atom), spiro, or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (e.g., $C_2$-$C_{15}$ fully saturated heterocycloalkyl or $C_2$-$C_{15}$ heterocycloalkenyl), from two to ten carbon atoms (e.g., $C_2$-$C_{10}$ fully saturated heterocycloalkyl or $C_2$-$C_{10}$ heterocycloalkenyl), from two to eight carbon atoms (e.g., $C_2$-$C_8$ fully saturated heterocycloalkyl or $C_2$-$C_8$ heterocycloalkenyl), from two to seven carbon atoms (e.g., $C_2$-$C_7$ fully saturated heterocycloalkyl or $C_2$-$C_7$ heterocycloalkenyl), from two to six carbon atoms (e.g., $C_2$-$C_6$ fully saturated heterocycloalkyl or $C_2$-$C_7$ heterocycloalkenyl), from two to five carbon atoms (e.g., $C_2$-$C_5$ fully saturated heterocycloalkyl or $C_2$-$C_5$ heterocycloalkenyl), or two to four carbon atoms (e.g., $C_2$-$C_4$ fully saturated heterocycloalkyl or $C_2$-$C_4$ heterocycloalkenyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides, and the oligosaccharides. In some embodiments, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. In some embodiments, the heterocycloalkyl is a 3- to 8-membered heterocycloalkenyl. In some embodiments, the heterocycloalkyl is a 3- to 7-membered heterocycloalkenyl. In some embodiments, the heterocycloalkyl is a 3- to 6-membered heterocycloalkenyl. In some embodiments, the heterocycloalkyl is a 4- to 6-membered heterocycloalkenyl. In some embodiments, the heterocycloalkyl is a 5- to 6-membered heterocycloalkenyl. Unless stated otherwise specifically in the specification, a heterocycloalkyl is optionally substituted, for example, with one or more oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycloalkyl is optionally substituted with one or more oxo, halogen, methyl, ethyl, —CN, —COOH, —COOMe, —$CF_3$, —OH, —OMe, —$NH_2$, or —$NO_2$. In some embodiments, the heterocycloalkyl is optionally substituted with one or more halogen, methyl, ethyl, —CN, —$CF_3$, —OH, or —OMe. In some embodiments, the heterocycloalkyl is optionally substituted with halogen.

"Heteroaryl" refers to a 5- to 14-membered ring system radical comprising one to thirteen carbon atoms, one to six heteroatoms selected from the group consisting of nitrogen, oxygen, phosphorous, and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. In some embodiments, the heteroaryl is C-linked. In some embodiments, the heteroaryl is N-linked. The heteroaryl radical may be a monocyclic, bicyclic, tricyclic, or tetracyclic ring system, which may include fused (when fused with a cycloalkyl or heterocycloalkyl ring, the heteroaryl is bonded through an aromatic ring atom) or bridged ring systems; and the nitrogen, carbon, or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. In some embodiments, the heteroaryl is a 5- to 6-membered ring comprising 1, 2, or 3 heteroatoms selected from the group consisting of oxygen, nitrogen, or sulfur. Examples include, but are not limited to, azepinyl, acridinyl, benzimidazolyl, benzothiazolyl, benzindolyl, benzodioxolyl, benzofuranyl, benzoxazolyl, benzothiadiazolyl, benzo[b][1,4]dioxepinyl, 1,4-benzodioxanyl, benzonaphthofuranyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, isothiazolyl, imidazolyl, indazolyl, indolyl, isoindolyl, indolinyl, isoindolinyl, isoquinolyl, indolizinyl, isoxazolyl, naphthyridinyl, oxadiazolyl, 2-oxoazepinyl, oxazolyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl is optionally substituted, for example, with one or more halogen, amino, nitrile, nitro, hydroxyl, alkyl, alkenyl, alkynyl, haloalkyl, alkoxy, carboxyl, carboxylate, aryl, cycloalkyl, heterocycloalkyl, or heteroaryl, and the like. In some embodiments, the heteroaryl is optionally substituted with one or more halogen, methyl, ethyl, —CN, —COOH, —COOMe, —$CF_3$, —OH, —OMe, —$NH_2$, or —$NO_2$. In some embodiments, the heteroaryl is optionally substituted with one or more halogen, methyl, ethyl, —CN, —$CF_3$, —OH, or —OMe. In some embodiments, the heteroaryl is optionally substituted with halogen.

The term "one or more" when referring to an optional substituent means that the subject group is optionally substituted with one, two, three, four, or more substituents. In some embodiments, the subject group is optionally substituted with one, two, three, or four substituents. In some embodiments, the subject group is optionally substituted with one, two, or three substituents. In some embodiments, the subject group is optionally substituted with one or two substituents. In some embodiments, the subject group is optionally substituted with one substituent. In some embodiments, the subject group is optionally substituted with two substituents.

The terms "effective amount" or "therapeutically effective amount," as used herein, refer to a sufficient amount of a compound disclosed herein being administered which will relieve to some extent one or more of the symptoms of the disease or condition being treated, e.g., cancer or an inflammatory disease. In some embodiments, the result is a reduction and/or alleviation of the signs, symptoms, or causes of a disease, or any other desired alteration of a biological system. For example, an "effective amount" for therapeutic uses is the amount of the composition comprising a compound disclosed herein required to provide a clinically significant decrease in disease symptoms. In some embodiments, an appropriate "effective" amount in any individual case is determined using techniques, such as a dose escalation study.

The term "substantially the same as" as used herein, refers to a powder x-ray diffraction pattern or differential scanning calorimetry pattern that is non-identical to those depicted herein, but that falls within the limits of experimental error, when considered by one of ordinary skill in the art.

As used herein, the term "therapeutic" means an agent utilized to treat, combat, ameliorate, or improve an unwanted condition or disease of a patient.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. "Administering" a pharmaceutical composition may be accomplished by injection, topical administration, and oral administration or by other methods alone or in combination with other known techniques.

By "pharmaceutically acceptable," it is meant the carrier, diluent or excipient must be compatible with the other ingredients of the composition and not deleterious to the recipient thereof.

The term "pharmaceutical composition" means a composition comprising at least one active ingredient, such as Compound 1 citrate coordination complex, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) inhibiting the disease; for example, inhibiting a disease, condition or disorder in an individual that is experiencing or displaying the pathology or symptomatology of the disease, condition or disorder (i.e., arresting further development of the pathology and/or symptomatology), and (2) ameliorating the disease; for example, ameliorating a disease, condition or disorder in an individual that is experiencing or displaying the pathology or symptomatology of the disease, condition or disorder (i.e., reversing the pathology and/or symptomatology).

The terms "treat," "treated," "treatment," or "treating" as used herein refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

Compound 1

Compound 1 is ((2-ethylbutanoyl)oxy)methyl (R)-2-hydroxy-3-propionamido-3,4-dihydro-2H-benzo[e][1,2]oxaborinine-8-carboxylate:

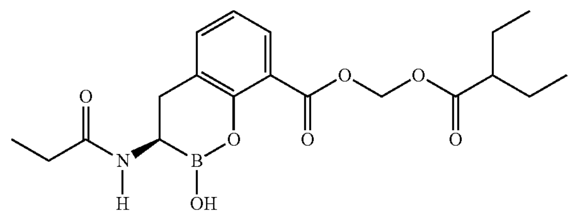 [SMILES: CCC(=O)N[C@H]1Cc2cccc(C(=O)OCOC(=O)C(CC)CC)c2OB1O]

but also exists in equilibrium with its open form (R)-(2-(3-((((2-ethylbutanoyl)oxy)methoxy)carbonyl)-2-hydroxyphenyl)-1-propionamidoethyl)boronic acid:

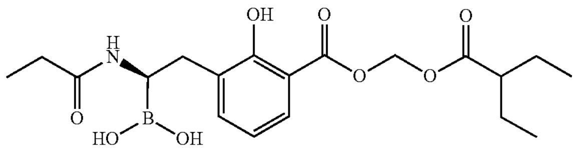 [SMILES: CCC(=O)N[C@@H](Cc1cccc(C(=O)OCOC(=O)C(CC)CC)c1O)B(O)O]

(Compound 1) and is also known as ledaborbactam etzadroxil.

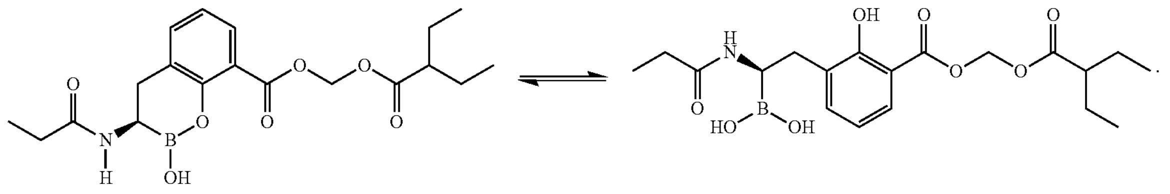 [SMILES: CCC(=O)N[C@H]1Cc2cccc(C(=O)OCOC(=O)C(CC)CC)c2OB1O ; CCC(=O)N[C@@H](Cc1cccc(C(=O)OCOC(=O)C(CC)CC)c1O)B(O)O]

Compound 1 Ethanolate

Compound 1 Ethanolate is ((2-ethylbutanoyl)oxy)methyl (R)-2-ethoxy-3-propionamido-3,4-dihydro-2H-benzo[e][1,2]oxaborinine-8-carboxylate:

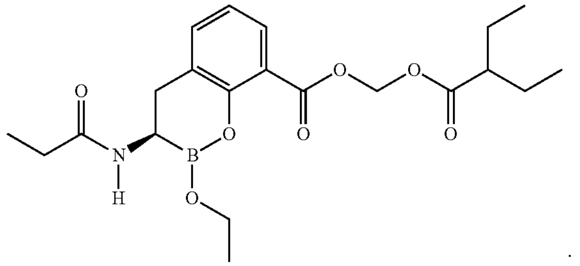 [SMILES: CCOB1Oc2c(cccc2C(=O)OCOC(=O)C(CC)CC)C[C@@H]1NC(=O)CC]

Compound 2

Compound 2 is (R)-2-hydroxy-3-propionamido-3,4-dihydro-2H-benzo[e][1,2]oxaborinine-8-carboxylic acid:

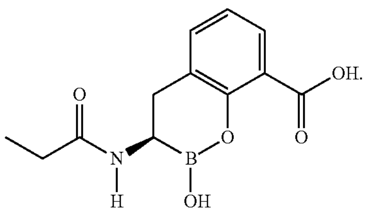 [SMILES: CCC(=O)N[C@H]1Cc2cccc(C(=O)O)c2OB1O]

Compound 1 Ester Coordination Complex

In some embodiments, Compound 1 ester coordination complex is a compound of Formula (I), or a pharmaceutically acceptable salt or solvate thereof:

Formula (I)

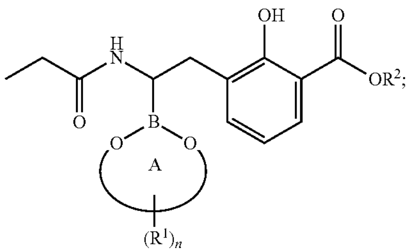

wherein:

- Ring A is a 4- to 8-membered heterocycloalkyl optionally comprising 1 or 2 additional heteroatoms selected from the group consisting of O, N, and S;
- each $R^1$ is independently halogen, —CN, —OH, -L-$OR^a$, -L-$NR^cR^d$, -L-C(=O)$R^a$, -L-C(=O)$OR^b$, -L-C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;
- or two $R^1$ on the same atom are taken together to form an oxo;
- n is 0, 1, 2, 3, 4, 5, or 6;
- $R^2$ is hydrogen, $R^4$, —$(R^3)_qOR^4$, —$(R^3)_qO(R^3)_qOR^4$, —$R^3$OC(=O)$R^4$, —$R^3$OC(=O)$OR^4$, —$R^3$OC(=O)$NHR^5$, or —$R^3$OC(=O)$N(R^5)_2$;
- each q is independently 2, 3, 4, 5, or 6;
- each $R^3$ is independently —$CH_2$—, —$CH(CH_3)$—, —$C(CH_3)_2$—, or 1,1-cyclopropylene;
- $R^4$ is $C_1$-$C_{12}$alkyl, $C_1$-$C_{12}$haloalkyl, $C_1$-$C_{12}$hydroxyalkyl, $C_1$-$C_{12}$aminoalkyl, $C_1$-$C_{12}$alkoxyalkyl, $C_2$-$C_{12}$alkenyl, $C_2$-$C_{12}$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;
- each $R^5$ is independently $C_1$-$C_{12}$alkyl, $C_1$-$C_{12}$haloalkyl, $C_1$-$C_{12}$hydroxyalkyl, $C_1$-$C_{12}$aminoalkyl, $C_1$-$C_{12}$alkoxyalkyl, $C_2$-$C_{12}$alkenyl, $C_2$-$C_{12}$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;
- or two $R^5$ are taken together with the nitrogen to which they are attached to form a heterocycloalkyl independently optionally substituted with one or more R;
- each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;
- each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;
- $R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;
- or $R^c$ and $R^d$ are taken together with the atom to which they are attached to form a heterocycloalkyl independently optionally substituted with one or more R; and
- L is absent or $C_1$-$C_3$alkylene independently optionally substituted with one or more R;
- each R is independently halogen, —CN, —OH, —$SF_5$, —SH, —S(=O)$C_1$-$C_3$alkyl, —S(=O)$_2C_1$-$C_3$alkyl, —S(=O)$_2NH_2$, —S(=O)$_2NHC_1$-$C_3$alkyl, —S(=O)$_2N(C_1$-$C_3$alkyl)$_2$, —S(=O)(=$NC_1$-$C_3$alkyl)($C_1$-$C_3$alkyl), —$NH_2$, —$NHC_1$-$C_3$alkyl, —$N(C_1$-$C_3$alkyl)$_2$, —N=S(=O)($C_1$-$C_3$alkyl)$_2$, —C(=O)$C_1$-$C_3$alkyl, —C(=O)OH, —C(=O)$OC_1$-$C_3$alkyl, —C(=O)$NH_2$, —C(=O)$NHC_1$-$C_3$alkyl, —C(=O)$N(C_1$-$C_3$alkyl)$_2$, —P(=O)($C_1$-$C_3$alkyl)$_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl;
- or two R on the same atom form an oxo.

In some embodiments of a compound of Formula (I), Ring A is a 5- to 6-membered heterocycloalkyl optionally comprising 1 or 2 additional heteroatoms selected from the group consisting of O, N, and S. In some embodiments of a compound of Formula (I), Ring A is a 5- to 6-membered heterocycloalkyl.

In some embodiments of a compound of Formula (I), Ring A is a 5-membered heterocycloalkyl optionally comprising 1 or 2 additional heteroatoms selected from the group consisting of O, N, and S. In some embodiments of a compound of Formula (I), Ring A is a 5-membered heterocycloalkyl.

In some embodiments of a compound of Formula (I), Ring A is a 6-membered heterocycloalkyl optionally comprising 1 or 2 additional heteroatoms selected from the group consisting of O, N, and S. In some embodiments of a compound of Formula (I), Ring A is a 6-membered heterocycloalkyl.

In some embodiments of a compound of Formula (I), n is 2, 3, 4, 5, or 6. In some embodiments of a compound of Formula (I), n is 2, 3, 4, or 5. In some embodiments of a compound of Formula (I), n is 2, 3, or 4. In some embodiments of a compound of Formula (I), n is 2. In some embodiments of a compound of Formula (I), n is 3. In some embodiments of a compound of Formula (I), n is 4.

In some embodiments of a compound of Formula (I), each $R^1$ is independently -L-C(=O)$R^a$, -L-C(=O)$OR^b$, -L-C(=O)$NR^cR^d$, $C_1$-$C_6$alkyl, $C_1$-$C_6$haloalkyl, $C_1$-$C_6$hydroxyalkyl or two $R^1$ on the same atom are taken together to form an oxo.

In some embodiments of a compound of Formula (I), each $R^1$ is independently -L-C(=O)$OR^b$, $C_1$-$C_6$alkyl, $C_1$-$C_6$haloalkyl, $C_1$-$C_6$hydroxyalkyl or two $R^1$ on the same atom are taken together to form an oxo.

In some embodiments of a compound of Formula (I), each $R^1$ is independently -L-C(=O)$OR^b$ or two $R^1$ on the same atom are taken together to form an oxo.

In some embodiments of a compound of Formula (I), each $R^1$ is independently —C(=O)$OR^b$ or —$CH_2$C(=O)$OR^b$ or two $R^1$ on the same atom are taken together to form an oxo.

In some embodiments of a compound of Formula (I), L is absent or $C_1$-$C_3$alkylene.

In some embodiments of a compound of Formula (I), L is absent. In some embodiments of a compound of Formula (I), L is $C_1$-$C_3$alkylene.

In some embodiments, the compound of Formula (I) is a compound of Formula (Ia), or a pharmaceutically acceptable salt or solvate thereof:

Formula (Ia)

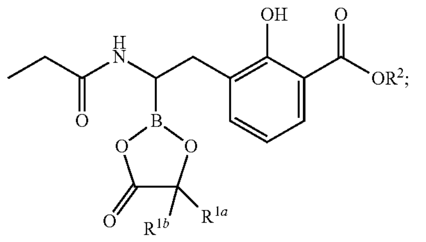

wherein:

$R^{1a}$ is hydrogen, halogen, —CN, —OH, -L-$OR^a$, -L-$NR^cR^d$, -L-C(=O)$R^a$, -L-C(=O)$OR^b$, -L-C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R; and $R^{1b}$ is hydrogen, halogen, —CN, —OH, -L-$OR^a$, -L-$NR^cR^d$, -L-C(=O)$R^a$, -L-C(=O)$OR^b$, -L-C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R.

In some embodiments, the compound of Formula (I) or (Ia) is a compound of Formula (Ia-1), or a pharmaceutically acceptable salt or solvate thereof:

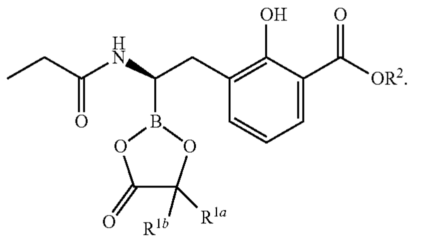

Formula (Ia-1). In some embodiments, the compound of Formula (I), (Ia), (Ia-1) is a compound of Formula (Ia-1a), or a pharmaceutically acceptable salt or solvate thereof:

Formula (Ia-1a)

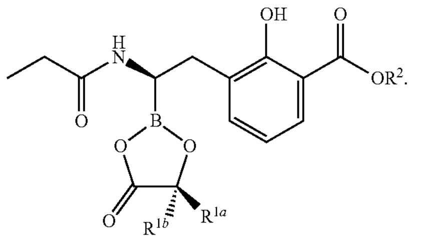

In some embodiments, the compound of Formula (I), (Ia), (Ia-1) is a compound of Formula (Ia-1b), or a pharmaceutically acceptable salt or solvate thereof:

Formula (Ia-1b)

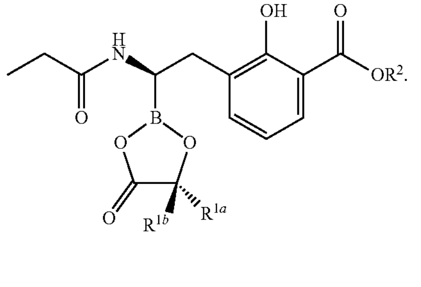

In some embodiments, the compound of Formula (I) is a compound of Formula (Ib), or a pharmaceutically acceptable salt or solvate thereof:

Formula (Ib)

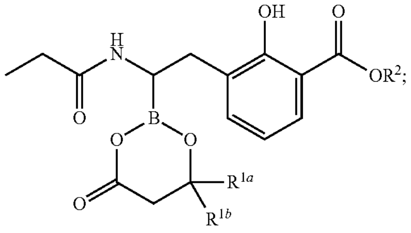

wherein:

$R^{1a}$ is hydrogen, halogen, —CN, —OH, -L-$OR^a$, -L-$NR^cR^d$, -L-C(=O)$R^a$, -L-C(=O)$OR^b$, -L-C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R; and $R^{1b}$ is hydrogen, halogen, —CN, —OH, -L-$OR^a$, -L-$NR^cR^d$, -L-C(=O)$R^a$, -L-C(=O)$OR^b$, -L-C(=O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R.

Formula (Ib). In some embodiments, the compound of Formula (I) or (Ib) is a compound of Formula (Ib-1), or a pharmaceutically acceptable salt or solvate thereof:

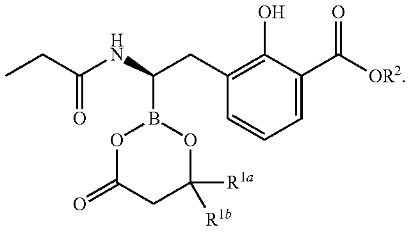

Formula (Ib-1). In some embodiments, the compound of Formula (I), (Ib), or (Ib-1) is a compound of Formula (Ib-1a), or a pharmaceutically acceptable salt or solvate thereof:

Formula (Ib-1a)

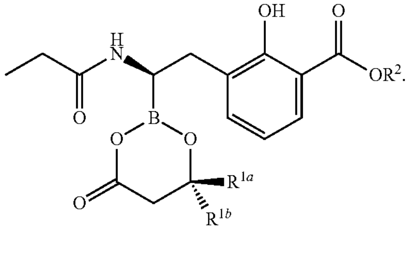

In some embodiments, the compound of Formula (I), (Ib), or (Ib-1) is a compound of Formula (Ib-1b), or a pharmaceutically acceptable salt or solvate thereof:

Formula (Ib-1b)

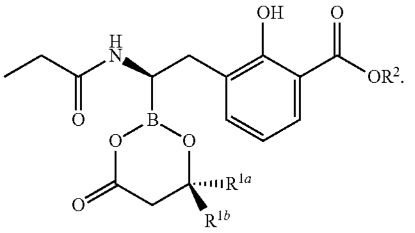

In some embodiments of a compound of Formula (Ia), (Ia-1), (Ia-1a), (Ia-1b), (Ib), (Ib-1), (Ib-1a), or (Ib-1b), $R^{1a}$ is hydrogen, -L-C(=O)$R^a$, -L-C(=O)$OR^b$, -L-C(=O)$NR^cR^d$, $C_1$-$C_6$alkyl, $C_1$-$C_6$haloalkyl, or $C_1$-$C_6$hydroxyalkyl.

In some embodiments of a compound of Formula (Ia), (Ia-1), (Ia-1a), (Ia-1b), (Ib), (Ib-1), (Ib-1a), or (Ib-1b), $R^{1a}$ is hydrogen, -L-C(=O)$OR^b$, $C_1$-$C_6$alkyl, $C_1$-$C_6$haloalkyl, or $C_1$-$C_6$hydroxyalkyl.

In some embodiments of a compound of Formula (Ia), (Ia-1), (Ia-1a), (Ia-1b), (Ib), (Ib-1), (Ib-1a), or (Ib-1b), $R^{1a}$ is -L-C(=O)$OR^b$.

In some embodiments of a compound of Formula (Ia), (Ia-1), (Ia-1a), (Ia-1b), (Ib), (Ib-1), (Ib-1a), or (Ib-1b), $R^{1a}$ is —C(=O)$OR^b$ or —$CH_2$C(=O)$OR^b$.

In some embodiments of a compound of Formula (Ia), (Ia-1), (Ia-1a), (Ia-1b), (Ib), (Ib-1), (Ib-1a), or (Ib-1b), $R^{1a}$ is —C(=O)$OR^b$.

In some embodiments of a compound of Formula (Ia), (Ia-1), (Ia-1a), (Ia-1b), (Ib), (Ib-1), (Ib-1a), or (Ib-1b), $R^{1a}$ is —C(=O)OH.

In some embodiments of a compound of Formula (Ia), (Ia-1), (Ia-1a), (Ia-1b), (Ib), (Ib-1), (Ib-1a), or (Ib-1b), $R^{1a}$ is —$CH_2$C(=O)$OR^b$.

In some embodiments of a compound of Formula (Ia), (Ia-1), (Ia-1a), (Ia-1b), (Ib), (Ib-1), (Ib-1a), or (Ib-1b), $R^{1a}$ is —$CH_2$C(=O)OH.

In some embodiments of a compound of Formula (Ia), (Ia-1), (Ia-1a), (Ia-1b), (Ib), (Ib-1), (Ib-1a), or (Ib-1b), $R^{1b}$ is hydrogen, -L-C(=O)$R^a$, -L-C(=O)$OR^b$, -L-C(=O)$NR^cR^d$, $C_1$-$C_6$alkyl, $C_1$-$C_6$haloalkyl, or $C_1$-$C_6$hydroxyalkyl.

In some embodiments of a compound of Formula (Ia), (Ia-1), (Ia-1a), (Ia-1b), (Ib), (Ib-1), (Ib-1a), or (Ib-1b), $R^{1b}$ is hydrogen, -L-C(=O)$OR^b$, $C_1$-$C_6$alkyl, $C_1$-$C_6$haloalkyl, or $C_1$-$C_6$hydroxyalkyl.

In some embodiments of a compound of Formula (Ia), (Ia-1), (Ia-1a), (Ia-1b), (Ib), (Ib-1), (Ib-1a), or (Ib-1b), $R^{1b}$ is -L-C(=O)$OR^b$.

In some embodiments of a compound of Formula (Ia), (Ia-1), (Ia-1a), (Ia-1b), (Ib), (Ib-1), (Ib-1a), or (Ib-1b), $R^{1b}$ is —C(=O)$OR^b$ or —$CH_2$C(=O)$OR^b$.

In some embodiments of a compound of Formula (Ia), (Ia-1), (Ia-1a), (Ia-1b), (Ib), (Ib-1), (Ib-1a), or (Ib-1b), $R^{1b}$ is —C(=O)$OR^b$.

In some embodiments of a compound of Formula (Ia), (Ia-1), (Ia-1a), (Ia-1b), (Ib), (Ib-1), (Ib-1a), or (Ib-1b), $R^{1b}$ is —C(=O)OH.

In some embodiments of a compound of Formula (Ia), (Ia-1), (Ia-1a), (Ia-1b), (Ib), (Ib-1), (Ib-1a), or (Ib-1b), $R^{1b}$ is —$CH_2$C(=O)$OR^b$.

In some embodiments of a compound of Formula (Ia), (Ia-1), (Ia-1a), (Ia-1b), (Ib), (Ib-1), (Ib-1a), or (Ib-1b), $R^{1b}$ is —$CH_2$C(=O)OH.

In some embodiments of a compound of Formula (I), (Ia), (Ia-1), (Ia-1a), (Ia-1b), (Ib), (Ib-1), (Ib-1a), or (Ib-1b), $R^2$ is hydrogen, $R^4$, $—R^3OC(=O)R^4$, or $—R^3OC(=O)OR^4$. In some embodiments of a compound of Formula (I), (Ia), (Ia-1), (Ia-1a), (Ia-1b), (Ib), (Ib-1), (Ib-1a), or (Ib-1b), $R^2$ is hydrogen. In some embodiments of a compound of Formula (I), (Ia), (Ia-1), (Ia-1a), (Ia-1b), (Ib), (Ib-1), (Ib-1a), or (Ib-1b), $R^2$ is $R^4$. In some embodiments of a compound of Formula (I), (Ia), (Ia-1), (Ia-1a), (Ia-1b), (Ib), (Ib-1), (Ib-1a), or (Ib-1b), $R^2$ is $—R^3OC(=O)R^4$ or $—R^3OC(=O)OR^4$. In some embodiments of a compound of Formula (I), (Ia), (Ia-1), (Ia-1a), (Ia-1b), (Ib), (Ib-1), (Ib-1a), or (Ib-1b), $R^2$ is $—R^3OC(=O)R^4$. In some embodiments of a compound of Formula (I), (Ia), (Ia-1), (Ia-1a), (Ia-1b), (Ib), (Ib-1), (Ib-1a), or (Ib-1b), $R^2$ is $—R^3OC(=O)OR^4$.

In some embodiments of a compound of Formula (I), (Ia), (Ia-1), (Ia-1a), (Ia-1b), (Ib), (Ib-1), (Ib-1a), or (Ib-1b), each $R^3$ is independently $—CH_2—$ or $—CH(CH_3)—$. In some embodiments of a compound of Formula (I), (Ia), (Ia-1), (Ia-1a), (Ia-1b), (Ib), (Ib-1), (Ib-1a), or (Ib-1b), each $R^3$ is independently $—CH_2—$.

In some embodiments of a compound of Formula (I), (Ia), (Ia-1), (Ia-1a), (Ia-1b), (Ib), (Ib-1), (Ib-1a), or (Ib-1b), $R^4$ is $C_1$-$C_{12}$alkyl, -L-aryl, or -L-heteroaryl; wherein each alkyl, aryl, and heteroaryl is independently optionally substituted with one or more R.

In some embodiments of a compound of Formula (I), (Ia), (Ia-1), (Ia-1a), (Ia-1b), (Ib), (Ib-1), (Ib-1a), or (Ib-1b), $R^4$ is $C_1$-$C_{12}$alkyl.

In some embodiments of a compound of Formula (I), (Ia), (Ia-1), (Ia-1a), (Ia-1b), (Ib), (Ib-1), (Ib-1a) or (Ib-1b) $R^4$ is

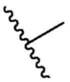, 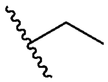, 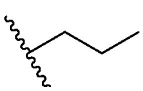,

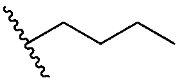, 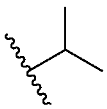, 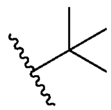,

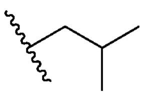, 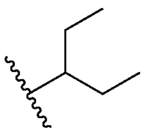, or 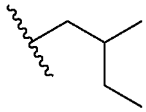.

In some embodiments of a compound of Formula (I), (Ia), (Ia-1), (Ia-1a), (Ia-1b), (Ib), (Ib-1), (Ib-1a), or (Ib-1b), $R^4$ is

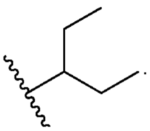 [SMILES: *C(CC)CC].

In some embodiments of a compound of Formula (I), (Ia), (Ia-1), (Ia-1a), (Ia-1b), (Ib), (Ib-1), (Ib-1a), or (Ib-1b), each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, -L-cycloalkyl, or -L-heterocycloalkyl; wherein each alkyl, cycloalkyl, or heterocycloalkyl is independently optionally substituted with one or more R. In some embodiments of a compound of Formula (I), (Ia), (Ia-1), (Ia-1a), (Ia-1b), (Ib), (Ib-1), (Ib-1a), or (Ib-1b), each $R^a$ is independently $C_1$-$C_6$alkyl or $C_1$-$C_6$haloalkyl; wherein each alkyl is independently optionally substituted with one or more R. In some embodiments of a compound of Formula (I), (Ia), (Ia-1), (Ia-1a), (Ia-1b), (Ib), (Ib-1), (Ib-1a), or (Ib-1b), each $R^a$ is independently $C_1$-$C_6$alkyl or $C_1$-$C_6$haloalkyl. In some embodiments of a compound of Formula (I), (Ia), (Ia-1), (Ia-1a), (Ia-1b), (Ib), (Ib-1), (Ib-1a), or (Ib-1b), each $R^a$ is independently $C_1$-$C_6$alkyl.

In some embodiments of a compound of Formula (I), (Ia), (Ia-1), (Ia-1a), (Ia-1b), (Ib), (Ib-1), (Ib-1a), or (Ib-1b), each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, -L-cycloalkyl, or -L-heterocycloalkyl; wherein each alkyl, cycloalkyl, or heterocycloalkyl is independently optionally substituted with one or more R. In some embodiments of a compound of Formula (I), (Ia), (Ia-1), (Ia-1a), (Ia-1b), (Ib), (Ib-1), (Ib-1a), or (Ib-1b), each $R^b$ is independently hydrogen, $C_1$-$C_6$alkyl or $C_1$-$C_6$haloalkyl; wherein each alkyl is independently optionally substituted with one or more R. In some embodiments of a compound of Formula (I), (Ia), (Ia-1), (Ia-1a), (Ia-1b), (Ib), (Ib-1), (Ib-1a), or (Ib-1b), each $R^b$ is independently hydrogen, $C_1$-$C_6$alkyl, or $C_1$-$C_6$haloalkyl. In some embodiments of a compound of Formula (I), (Ia), (Ia-1), (Ia-1a), (Ia-1b), (Ib), (Ib-1), (Ib-1a), or (Ib-1b), each $R^b$ is independently hydrogen or $C_1$-$C_6$alkyl. In some embodiments of a compound of Formula (I), (Ia), (Ia-1), (Ia-1a), (Ia-1b), (Ib), (Ib-1), (Ib-1a), or (Ib-1b), each $R^b$ is hydrogen. In some embodiments of a compound of Formula (I), (Ia), (Ia-1), (Ia-1a), (Ia-1b), (Ib), (Ib-1), (Ib-1a), or (Ib-1b), each $R^b$ is independently $C_1$-$C_6$alkyl.

In some embodiments of a compound of Formula (I), (Ia), (Ia-1), (Ia-1a), (Ia-1b), (Ib), (Ib-1), (Ib-1a), or (Ib-1b), $R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, -L-cycloalkyl, or -L-heterocycloalkyl; wherein each alkyl, cycloalkyl, or heterocycloalkyl is independently optionally substituted with one or more R. In some embodiments of a compound of Formula (I), (Ia), (Ia-1), (Ia-1a), (Ia-1b), (Ib), (Ib-1), (Ib-1a), or (Ib-1b), $R^c$ and $R^d$ are each independently hydrogen, $C_1$-$C_6$alkyl or $C_1$-$C_6$haloalkyl; wherein each alkyl is independently optionally substituted with one or more R. In some embodiments of a compound of Formula (I), (Ia), (Ia-1), (Ia-1a), (Ia-1b), (Ib), (Ib-1), (Ib-1a), or (Ib-1b), $R^c$ and $R^d$ are each independently hydrogen, $C_1$-$C_6$alkyl, or $C_1$-$C_6$haloalkyl. In some embodiments of a compound of Formula (I), (Ia), (Ia-1), (Ia-1a), (Ia-1b), (Ib), (Ib-1), (Ib-1a), or (Ib-1b), $R^c$ and $R^d$ are each independently hydrogen or $C_1$-$C_6$alkyl. In some embodiments of a compound of Formula (I), (Ia), (Ia-1), (Ia-1a), (Ia-1b), (Ib), (Ib-1), (Ib-1a), or (Ib-1b), $R^c$ and $R^d$ are each hydrogen. In some embodiments of a compound of Formula (I), (Ia), (Ia-1), (Ia-1a), (Ia-1b), (Ib), (Ib-1), (Ib-1a), or (Ib-1b), $R^c$ and $R^d$ are each independently $C_1$-$C_6$alkyl.

In some embodiments of a compound of Formula (I), (Ia), (Ia-1), (Ia-1a), (Ia-1b), (Ib), (Ib-1), (Ib-1a), or (Ib-1b), L is absent or $C_1$-$C_3$alkylene. In some embodiments of a compound of Formula (I), (Ia), (Ia-1), (Ia-1a), (Ia-1b), (Ib), (Ib-1), (Ib-1a), or (Ib-1b), L is absent. In some embodiments of a compound of Formula (I), (Ia), (Ia-1), (Ia-1a), (Ia-1b), (Ib), (Ib-1), (Ib-1a), or (Ib-1b), L is $C_1$-$C_3$alkylene.

In some embodiments of a compound of Formula (I), (Ia), (Ia-1), (Ia-1a), (Ia-1b), (Ib), (Ib-1), (Ib-1a), or (Ib-1b), each R is independently halogen, —CN, —OH, $—NH_2$, $—NHC_1$-$C_3$alkyl, $—N(C_1$-$C_3alkyl)_2$, $—C(=O)C_1$-$C_3$alkyl, $—C(=O)OH$, $—C(=O)OC_1$-$C_3$alkyl, $—C(=O)NH_2$, $—C(=O)NHC_1$-$C_3$alkyl, $—C(=O)N(C_1$-$C_3alkyl)_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl. In some embodiments of a compound of Formula (I), (Ia), (Ia-1), (Ia-1a), (Ia-1b), (Ib), (Ib-1), (Ib-1a), or (Ib-1b), each R is independently halogen, —CN, —OH, —$NH_2$, —$NHC_1$-$C_3$alkyl, —N($C_1$-$C_3$alkyl)$_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl. In some embodiments of a compound of Formula (I), (Ia), (Ia-1), (Ia-1a), (Ia-1b), (Ib), (Ib-1), (Ib-1a), or (Ib-1b), each R is independently halogen, —CN, —OH, —$NH_2$, —C(═O)$C_1$-$C_3$alkyl, —C(═O)OH, —C(═O)O$C_1$-$C_3$alkyl, —C(═O)$NH_2$, —C(═O)NH$C_1$-$C_3$alkyl, —C(═O)N($C_1$-$C_3$alkyl)$_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl. In some embodiments of a compound of Formula (I), (Ia), (Ia-1), (Ia-1a), (Ia-1b), (Ib), (Ib-1), (Ib-1a), or (Ib-1b), each R is independently halogen, —CN, —OH, —$NH_2$, —$NHC_1$-$C_3$alkyl, —N($C_1$-$C_3$alkyl)$_2$, $C_1$-$C_3$alkyl, or $C_1$-$C_3$haloalkyl. In some embodiments of a compound of Formula (I), (Ia), (Ia-1), (Ia-1a), (Ia-1b), (Ib), (Ib-1), (Ib-1a), or (Ib-1b), each R is independently halogen, $C_1$-$C_3$alkyl, or $C_1$-$C_3$haloalkyl.

Compound 1 Citrate Coordination Complex

In some embodiments, Compound 1 exists in solid form as a covalently bound citrate coordination complex. In some embodiments, Compound 1 citrate coordination complex is (R)-(2-(3-((((2-ethylbutanoyl)oxy)methoxy)carbonyl)-2-hydroxyphenyl)-1-propionamidoethyl)boronic acid citrate coordination complex.

In some embodiments, Compound 1 citrate coordination complex is (R)-2,2'-(2-(2-(3-((((2-ethylbutanoyl)oxy)methoxy)carbonyl)-2-hydroxyphenyl)-1-propionamidoethyl)-5-oxo-1,3,2-dioxaborolane-4,4-diyl)diacetic acid:

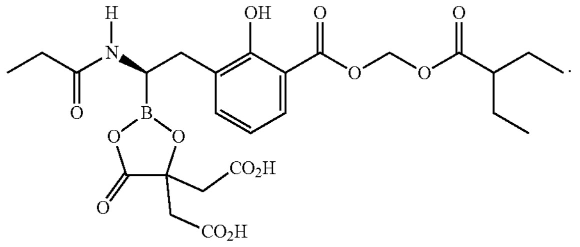 [SMILES: CCC(=O)N[C@@H](Cc1cccc(C(=O)OCOC(=O)C(CC)CC)c1O)B1OC(=O)C(CC(=O)O)(CC(=O)O)O1]

In some embodiments, the Compound 1 citrate coordination complex converts to Compound 1 closed form when in contact with water:

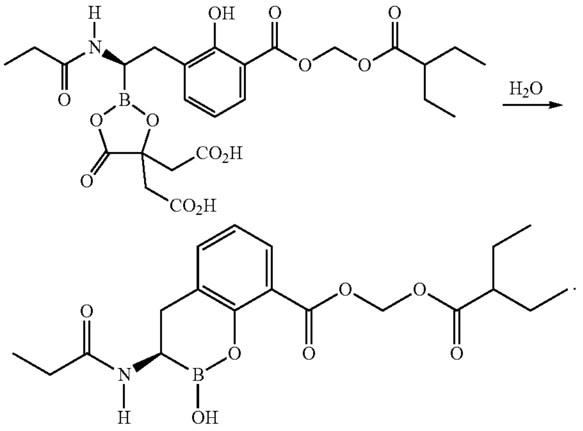

Alternate Compound 1 Citrate Coordination Complex

In some embodiments, Compound 1 citrate coordination complex is 4-(carboxymethyl)-2-((R)-2-(3-((((2-ethylbutanoyl)oxy)methoxy)carbonyl)-2-hydroxyphenyl)-1-propionamidoethyl)-6-oxo-1,3,2-dioxaborinane-4-carboxylic acid:

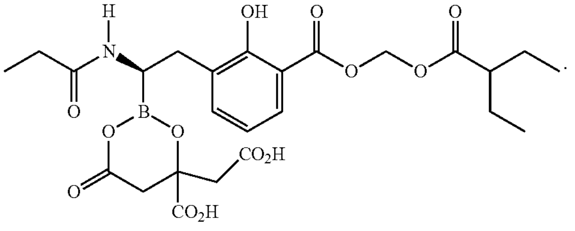 [SMILES: CCC(=O)N[C@@H](Cc1cccc(C(=O)OCOC(=O)C(CC)CC)c1O)B1OC(=O)CC(CC(=O)O)(C(=O)O)O1]

In some embodiments, the alternate Compound 1 citrate coordination complex is a racemic mixture. In some embodiments, the alternate Compound 1 citrate coordination complex is a pure stereoisomer.

In some embodiments, the alternate Compound 1 citrate coordination complex is (S)-4-(carboxymethyl)-2-((R)-2-(3-((((2-ethylbutanoyl)oxy)methoxy)carbonyl)-2-hydroxyphenyl)-1-propionamidoethyl)-6-oxo-1,3,2-dioxaborinane-4-carboxylic acid:

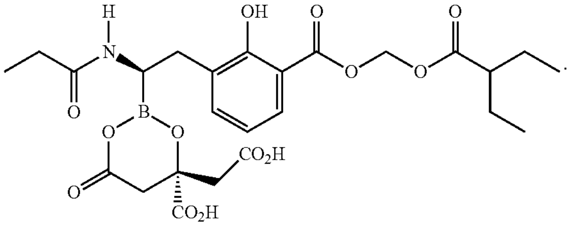 [SMILES: CCC(=O)N[C@@H](Cc1cccc(C(=O)OCOC(=O)C(CC)CC)c1O)B1OC(=O)C[C@@](CC(=O)O)(C(=O)O)O1]

In some embodiments, the alternate Compound 1 citrate coordination complex is (R)-4-(carboxymethyl)-2-((R)-2-(3-((((2-ethylbutanoyl)oxy)methoxy)carbonyl)-2-hydroxyphenyl)-1-propionamidoethyl)-6-oxo-1,3,2-dioxaborinane-4-carboxylic acid:

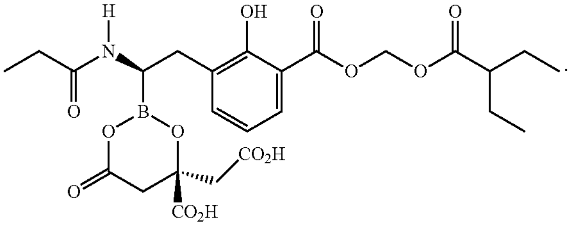 [SMILES: CCC(=O)N[C@@H](Cc1cccc(C(=O)OCOC(=O)C(CC)CC)c1O)B1OC(=O)C[C@](CC(=O)O)(C(=O)O)O1]

In some embodiments, the alternate Compound 1 citrate coordination complex is

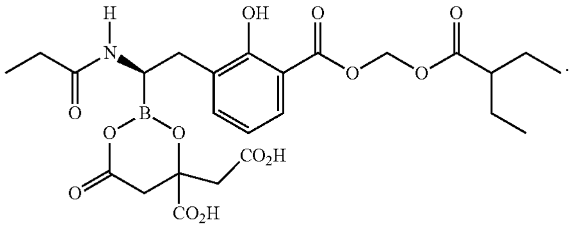 [SMILES: CCC(=O)N[C@@H](Cc1cccc(C(=O)OCOC(=O)C(CC)CC)c1O)B1OC(=O)CC(CC(=O)O)(C(=O)O)O1]

In some embodiments, the alternate Compound 1 citrate coordination complex converts to Compound 1 closed form when in contact with water:

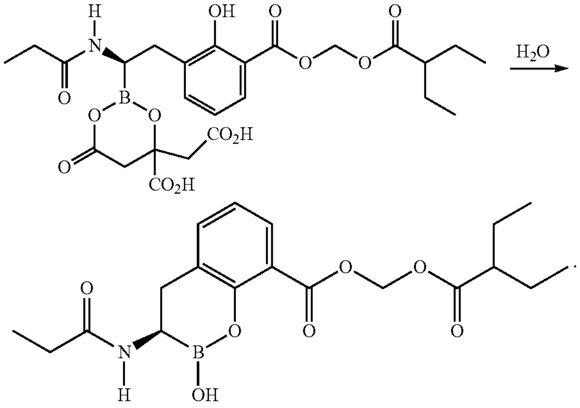

In some embodiments, the citrate coordination complex allows for the development of a dry powder, immediate release formulation as compared to other forms, such as the ethanolate, which could not be formulated directly as an immediate release formulation. This is shown in FIG. 1 which compares a fixed dose combination of ceftibuten dihydrate with the citrate coordination complex (see Example 15a) to a comparable fixed dose combination of ceftibuten dihydrate with the ethanolate complex (see Example 15b). Dissolution testing (Apparatus II method) was performed using 900 mL of pH 6.8 50 mM sodium bicarbonate buffer solution and a 75 RPM paddle speed. The dissolution profile of the ethanolate complex showed <40% release of the drug substance at 60 minutes, while compound 1 citrate coordination complex released 100% by 10 minutes.

Further Forms of Complex Disclosed Herein

In some embodiments, the amide oxygen atom of compound 1 citrate coordination complex may be coordinated to the boron atom in solution or in solid form and consequently the compounds described herein may be drawn (or depicted) as either

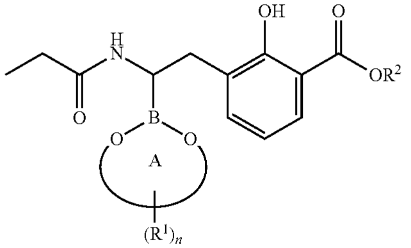

or

-continued

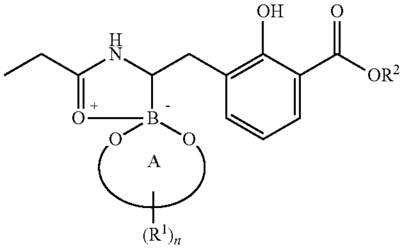

but both of them are just depictions of compound 1 citrate coordination complex of Formula (I).

Similarly, compound 1 citrate coordination complex may be drawn (or depicted) as either

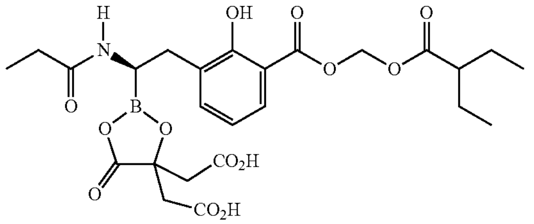

or

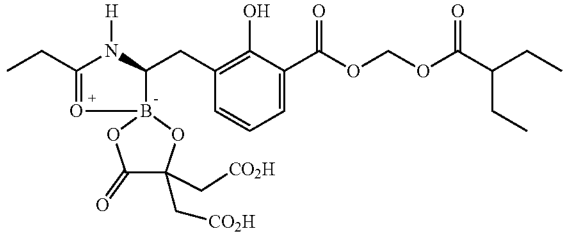

but both of them are just depictions of compound 1 citrate coordination complex.

Accordingly, the alternate compound 1 citrate coordination complex may be drawn (or depicted) as either

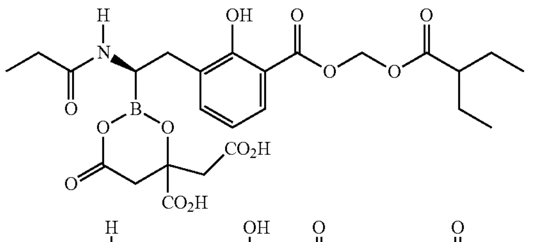

or

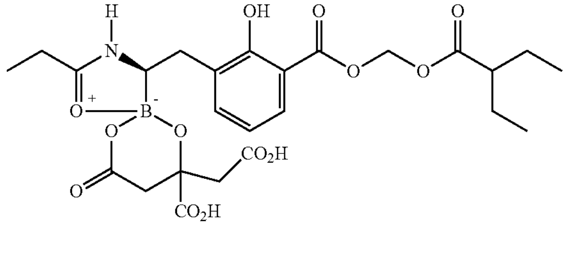

but both of them are just depictions of the alternate compound 1 citrate coordination complex.

Similarly, compound 1 citrate coordination complex may be drawn (or depicted) as either

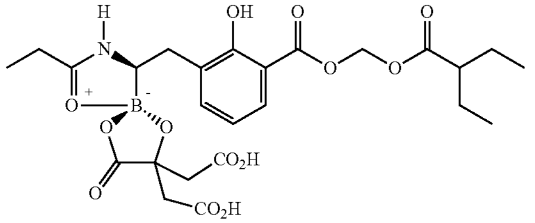

or

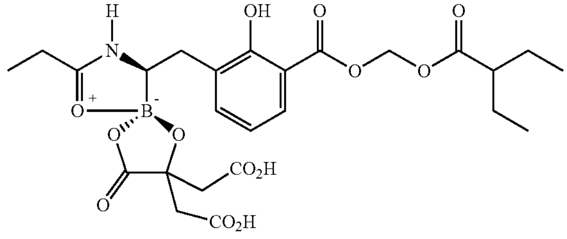

but both of them are just depictions of compound 1 citrate coordination complex.

Accordingly, the alternate compound 1 citrate coordination complex may be drawn (or depicted) as either

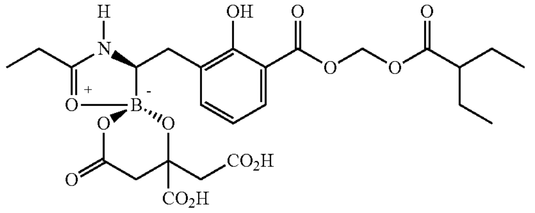

or

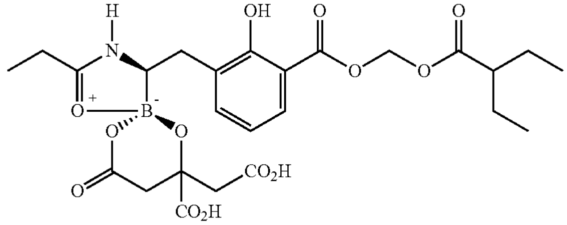

but both of them are just depictions of the alternate compound 1 citrate coordination complex.

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center independently exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, boron, carbon, nitrogen, oxygen, phosphorous, sulfur, fluorine, and chlorine, such as $^{2}H$, $^{3}H$, $^{10}B$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, one or more hydrogen in a compound disclosed herein has been replaced by a deuterium atom. In some embodiments, one or more alkyl substituents in a compound disclosed herein has been replaced by a deuteroalkyl substituents.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, but not limited to, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, gluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate, undecanoate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^{+}(C_1\text{-}C_4\ alkyl)_4$ hydroxide, and the like. In some embodiments, the compounds described herein are sodium salts. In some embodiments, the compounds described herein are disodium salts.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Solid State Forms

Provided herein is a solid state form of (R)-(2-(3-((((2-ethylbutanoyl)oxy)methoxy)carbonyl)-2-hydroxyphenyl)-1-propionamidoethyl)boronic acid citrate (Compound 1 citrate coordination complex) or a pharmaceutically acceptable salt or solvate thereof. In some embodiments, the solid state form is a crystalline form. In some embodiments, the solid state form is crystalline (R)-(2-(3-((((2-ethylbutanoyl)oxy)methoxy)carbonyl)-2-hydroxyphenyl)-1-propionamidoethyl)boronic acid citrate (Compound 1 citrate coordination complex) as a free form. In some embodiments, the solid state form is crystalline (R)-(2-(3-((((2-ethylbutanoyl)oxy)methoxy)carbonyl)-2-hydroxyphenyl)-1-propionamidoethyl)boronic acid citrate (Compound 1 citrate coordination complex) as a pharmaceutically acceptable salt or solvate thereof. In some embodiments, the solid state form is crystalline (R)-(2-(3-((((2-ethylbutanoyl)oxy)methoxy)carbonyl)-2-hydroxyphenyl)-1-propionamidoethyl)boronic acid citrate (Compound 1 citrate coordination complex) as a pharmaceutically acceptable salt thereof. In some embodiments, the solid state form is crystalline (R)-(2-(3-((((2-ethylbutanoyl)oxy)methoxy)carbonyl)-2-hydroxyphenyl)-

1-propionamidoethyl)boronic acid citrate (Compound 1 citrate coordination complex) as a pharmaceutically acceptable solvate thereof.

Polymorph Form A

Figure 2:
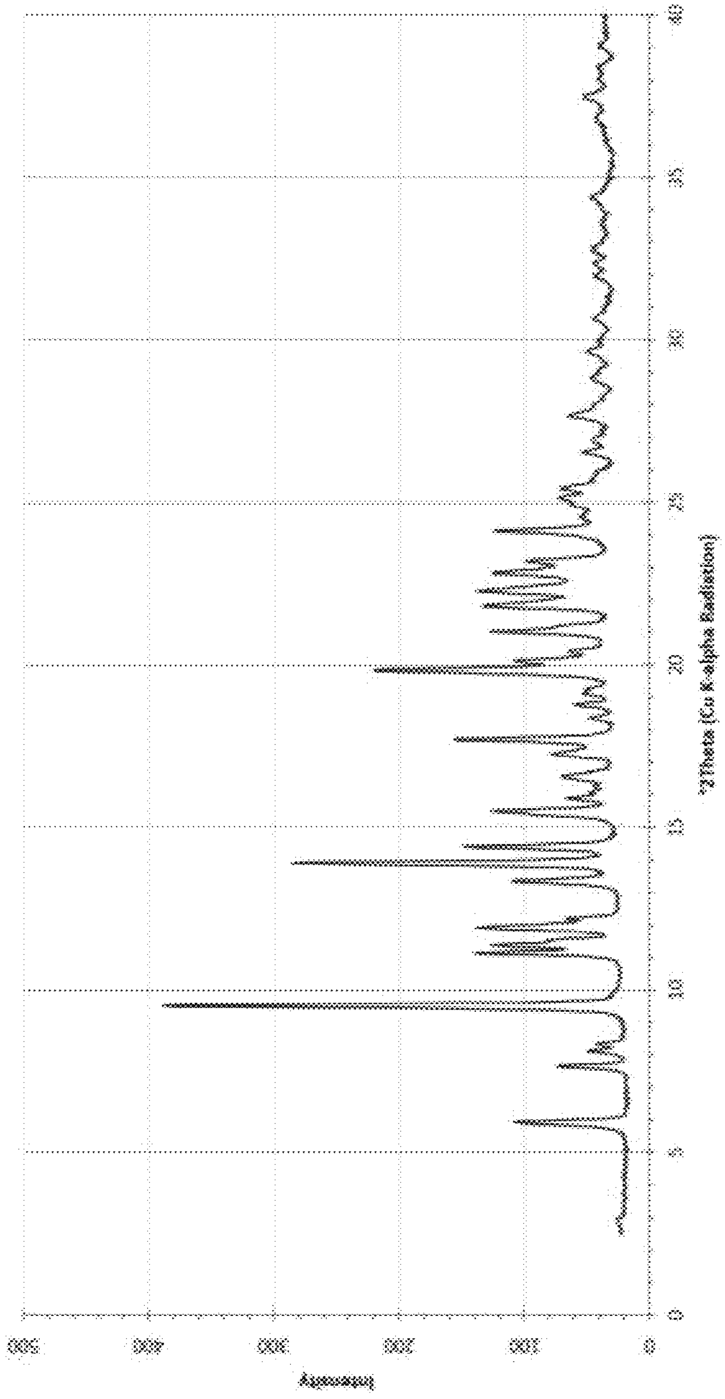
FIG. 2 shows the XRPD pattern for Compound 1 citrate coordination complex Form A.
Figure 3:
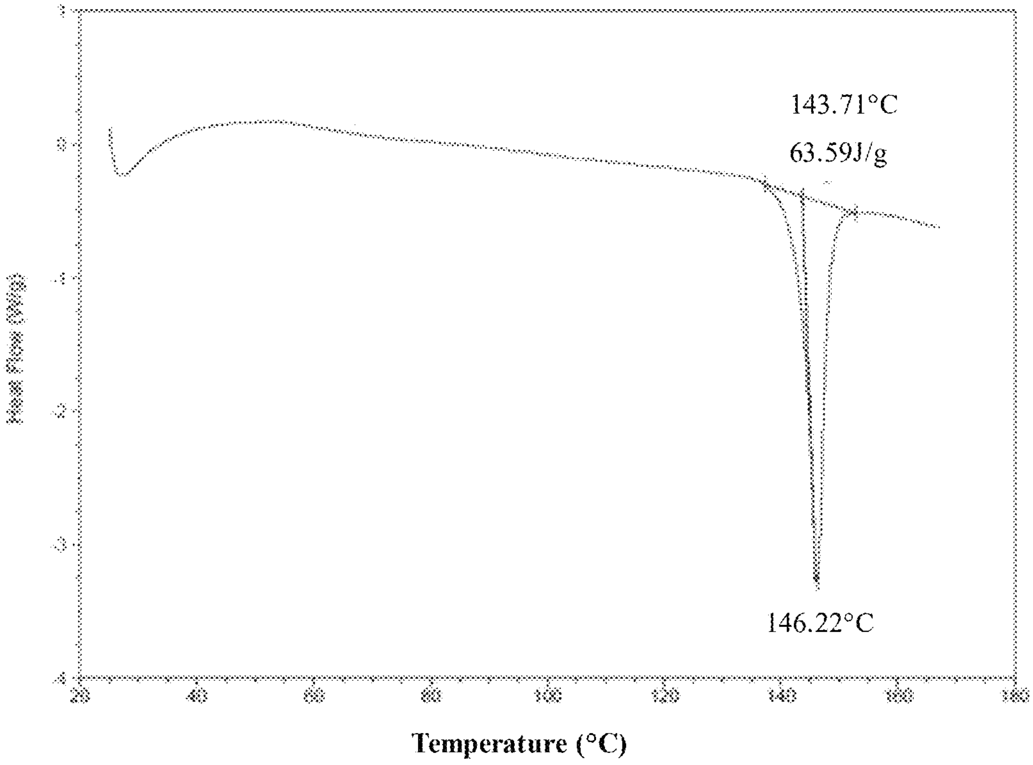
FIG. 3 shows the DSC thermogram of Compound 1 citrate coordination complex Form A.

The term "polymorph Form A" or "Form A" refers to a crystalline form of (R)-(2-(3-((((2-ethylbutanoyl)oxy)methoxy)carbonyl)-2-hydroxyphenyl)-1-propionamidoethyl)boronic acid citrate (Compound 1 citrate coordination complex) that exhibits an X-ray powder diffraction pattern substantially the same as that shown in FIG. 2 and/or a DSC thermogram substantially the same as that shown in FIG. 3.

In some embodiments, (R)-(2-(3-((((2-ethylbutanoyl)oxy)methoxy)carbonyl)-2-hydroxyphenyl)-1-propionamidoethyl)boronic acid citrate (Compound 1 citrate coordination complex) polymorph Form A exhibits an X-ray powder diffraction pattern characterized by the diffraction pattern summarized in Table 1. In some embodiments, the polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least 3 peaks of (±0.1° 2θ) of Table 1. In some embodiments, the polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least 4 peaks of (±0.1° 2θ) of Table 1, at least 5 peaks of (±0.1° 2θ) of Table 1, at least 6 peaks of (±0.1° 2θ) of Table 1, at least 7 peaks of (±0.1° 2θ) of Table 1, at least 8 peaks of (±0.1° 2θ) of Table 1, or at least 9 peaks of (±0.1° 2θ) of Table 1.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises characteristic peaks at 5.9°±0.1° 2θ, 11.1°±0.1° 2θ, and 13.9°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises a characteristic peak at 5.9°±0.1° 2θ, 11.1 0.1° 2θ, and 13.9°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises a characteristic peak at 11.1°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises a characteristic peak at 13.9°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises characteristic peaks at 9.5°±0.1° 2θ and 11.9°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 7.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 11.4°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 13.3°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 14.4°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 19.8°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises characteristic peaks at 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.9°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least three characteristic peaks selected from the group consisting of 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.9°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least four characteristic peaks selected from the group consisting of 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.9°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least five characteristic peaks selected from the group consisting of 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.9°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least six characteristic peaks selected from the group consisting of 5.9°±0.1° 2θ, 7.7°±0.1° 2θ, 9.5°±0.1° 2θ, 11.1°+0.1° 2θ, 11.4°±0.1° 2θ, 11.9°±0.1° 2θ, 13.9°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least seven characteristic peaks selected from the group consisting of 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.9°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises characteristic peaks at 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.3°±0.1° 2θ, 13.9°±0.1° 2θ, 14.4°±0.1° 2θ, 17.7°±0.1° 2θ, and 19.8°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least three characteristic peaks selected from the group consisting of 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.3°±0.1° 2θ, 13.9°±0.1° 2θ, 14.4°±0.1° 2θ, 17.7°±0.1° 2θ, and 19.8°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least four characteristic peaks selected from the group consisting of 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.3°±0.1° 2θ, 13.9°±0.1° 2θ, 14.4°±0.1° 2θ, 17.7°±0.1° 2θ, and 19.8°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least five characteristic peaks selected from the group consisting of 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.3°±0.1° 2θ, 13.9°±0.1° 2θ, 14.4°±0.1° 2θ, 17.7°±0.1° 2θ, and 19.8°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least six characteristic peaks selected from the group consisting of 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.3°±0.1° 2θ, 13.9°±0.1° 2θ, 14.4°±0.1° 2θ, 17.7°±0.1° 2θ, and 19.8°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least seven characteristic peaks selected from the group consisting of 5.9°±0.1° 2θ, 7.7°±0.1° 2θ, 9.5°±0.1° 2θ, 11.1°±0.1° 2θ, 11.4°±0.1° 2θ, 11.9°±0.1° 2θ, 13.3°±0.1° 2θ, 13.9°±0.1° 2θ, 14.4°±0.1° 2θ, 17.7°±0.1° 2θ, and 19.8°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises characteristic peaks at 5.9°±0.1° 2θ, 9.5°±0.1° 2θ, 11.1°±0.1° 2θ, 11.9°±0.1° 2θ, and 13.9°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises a characteristic peak at 5.9°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises a characteristic peak at 9.5°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises a characteristic peak at 11.1°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises a characteristic peak at 11.9°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises a characteristic peak at 13.9°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises characteristic peaks at 11.4°±0.1° 2θ, 13.3°±0.1° 2θ, 14.4°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises characteristic peaks at 8.1°±0.1° 2θ, 8.3°±0.1° 2θ, 11.5°±0.1° 2θ, and 17.2°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises characteristic peaks at 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least one characteristic peak selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least two characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least three characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least four characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least five characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least six characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least seven characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least eight characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least nine characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least ten characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least 11 characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least 12 characteristic peaks selected from the group consisting of 5.9°±0.1° 2θ, 8.1°±0.1° 2θ, 8.3°±0.1° 2θ, 9.5°±0.1° 2θ, 11.1°±0.1° 2θ, 11.4°±0.1° 2θ, 11.5°±0.1° 2θ, 11.9°±0.1° 2θ, 13.3°±0.1° 2θ, 13.9°±0.1° 2θ, 14.4°±0.1° 2θ, 17.2°±0.1° 2θ, and 17.7°±0.1° 2θ.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) has a single endotherm in DSC having an onset at about 143.7° C.

In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) crystalizes as needles and is thermodynamically stable. In some embodiments, polymorph Form A of (R)-(2-(3-((((2-ethylbutanoyl)oxy)methoxy)carbonyl)-2-hydroxyphenyl)-1-propionamidoethyl)boronic acid citrate (Compound 1 citrate coordination complex) is more thermodynamically stable than polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex).

TABLE 1

Form A Characteristic XRPD Signals (2θ, Cu)

| Angle 2-Theta ° | Intensity, normalized |
|---|---|
| 5.9 | 33.21 |
| 7.7 | 12.56 |
| 8.1 | 3.84 |
| 8.3 | 1.65 |
| 9.5 | 100.00 |
| 11.1 | 21.22 |
| 11.4 | 18.80 |
| 11.5 | 7.06 |
| 11.9 | 20.50 |
| 12.2 | 4.21 |
| 13.3 | 12.46 |
| 13.9 | 44.92 |
| 14.4 | 17.55 |
| 15.4 | 5.68 |
| 15.9 | 1.84 |
| 16.6 | 2.55 |
| 17.2 | 3.34 |
| 17.7 | 14.85 |
| 18.4 | 2.61 |
| 18.7 | 3.88 |
| 19.1 | 3.07 |
| 19.3 | 2.57 |
| 19.8 | 21.59 |
| 20.1 | 5.92 |
| 20.4 | 4.04 |
| 21.0 | 7.81 |
| 21.2 | 0.74 |
| 21.8 | 8.28 |
| 22.2 | 8.52 |
| 22.8 | 6.76 |
| 23.2 | 3.61 |
| 24.1 | 6.04 |

Polymorph Form B

Figure 6:
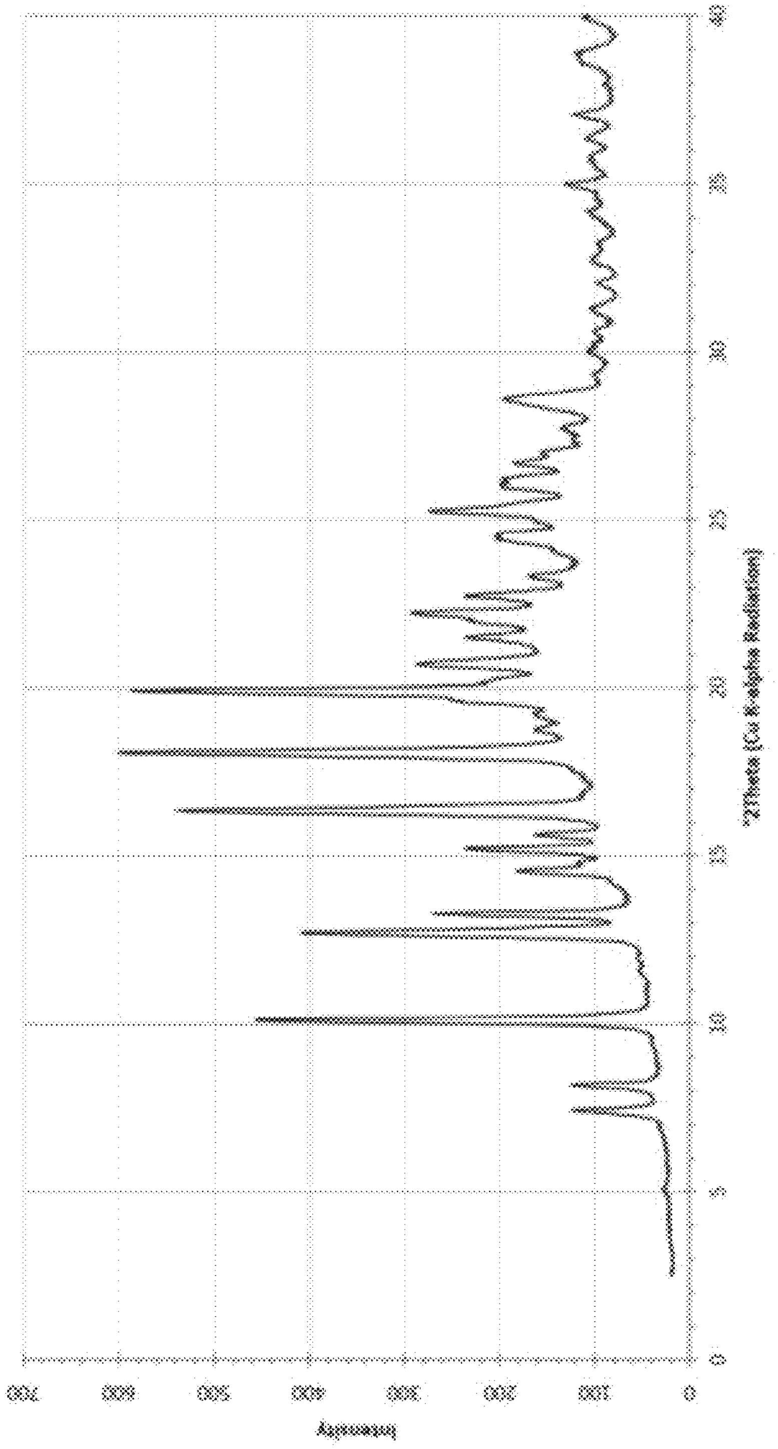
FIG. 6 shows the XRPD pattern for Compound 1 citrate coordination complex Form B.
Figure 7:
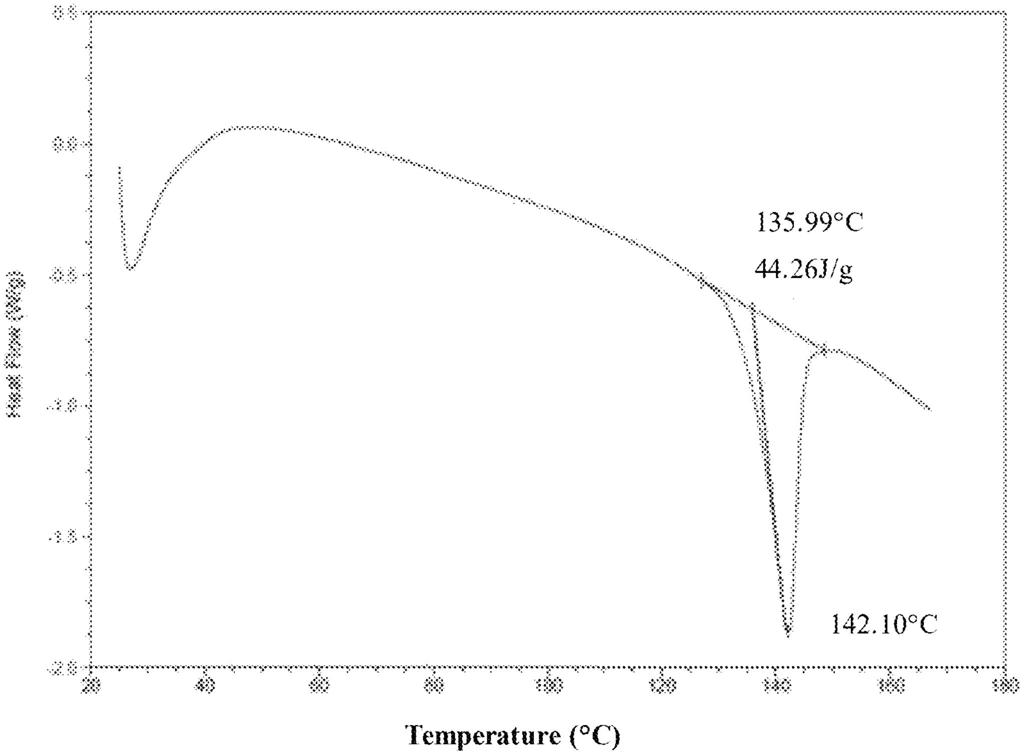
FIG. 7 shows the DSC thermogram of Compound 1 citrate coordination complex Form B.

The term "polymorph Form B" or "Form B" refers to a crystalline form of (R)-(2-(3-((((2-ethylbutanoyl)oxy)methoxy)carbonyl)-2-hydroxyphenyl)-1-propionamidoethyl)boronic acid citrate (Compound 1 citrate coordination complex) that exhibits an X-ray powder diffraction pattern substantially the same as that shown in FIG. 6 and/or a DSC thermogram substantially the same as that shown in FIG. 7.

In some embodiments, (R)-(2-(3-((((2-ethylbutanoyl)oxy)methoxy)carbonyl)-2-hydroxyphenyl)-1-propionamidoethyl)boronic acid citrate (Compound 1 citrate coordination complex) polymorph Form B exhibits an X-ray powder diffraction pattern characterized by the diffraction pattern summarized in Table 2. In some embodiments, the polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least 3 peaks of (±0.1° 2θ) of Table 2. In some embodiments, the polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least 4 peaks of (±0.1° 2θ) of Table 2, at least 5 peaks of (±0.1° 2θ) of Table 2, at least 6 peaks of (±0.1° 2θ) of Table 2, at least 7 peaks of (±0.1° 2θ) of Table 2, at least 8 peaks of (±0.1° 2θ) of Table 2, or at least 9 peaks of (±0.1° 2θ) of Table 2.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises characteristic peaks at 10.1°±0.1° 2θ and 12.7°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 16.3°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 18.1°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 8.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 13.3°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 15.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 19.9°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) further comprises a characteristic peak at 22.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises characteristic peaks at 10.1°±0.1° 2θ, 12.7°±0.1° 2θ, 16.3°±0.1° 2θ, and 18.1°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least three characteristic peaks selected from the group consisting of 10.1°±0.1° 2θ, 12.7°±0.1° 2θ, 16.3°±0.1° 2θ, and 18.1°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises characteristic peaks at 8.2°±0.1° 2θ, 10.1°±0.1° 2θ, 12.7°±0.1° 2θ, 13.3°±0.1° 2θ, 15.2°±0.1° 2θ, 16.3°±0.1° 2θ, 18.1°±0.1° 2θ, 19.9°±0.1° 2θ, and 22.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least three characteristic peaks selected from the group consisting of 8.2°±0.1° 2θ, 10.1°±0.1° 2θ, 12.7°±0.1° 2θ, 13.3°±0.1° 2θ, 15.2°±0.1° 2θ, 16.3°±0.1° 2θ, 18.1°±0.1° 2θ, 19.9°±0.1° 2θ, and 22.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least four characteristic peaks selected from the group consisting of 8.2°±0.1° 2θ, 10.1°±0.1° 2θ, 12.7°±0.1° 2θ, 13.3°±0.1° 2θ, 15.2°±0.1° 2θ, 16.3°±0.1° 2θ, 18.1°±0.1° 2θ, 19.9°±0.1° 2θ, and 22.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least five characteristic peaks selected from the group consisting of 8.2°±0.1° 2θ, 10.1°±0.1° 2θ, 12.7°±0.1° 2θ, 13.3°±0.1° 2θ, 15.2°±0.1° 2θ, 16.3°±0.1° 2θ, 18.1°±0.1° 2θ, 19.9°±0.1° 2θ, and 22.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least six characteristic peaks selected from the group consisting of 8.2°±0.1° 2θ, 10.1°±0.1° 2θ, 12.7°±0.1° 2θ, 13.3°±0.1° 2θ, 15.2°±0.1° 2θ, 16.3°±0.1° 2θ, 18.1°±0.1° 2θ, 19.9°±0.1° 2θ, and 22.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least seven characteristic peaks selected from the group consisting of 8.2°±0.1° 2θ, 10.1°±0.1° 2θ, 12.7°±0.1° 2θ, 13.3°±0.1° 2θ, 15.2°±0.1° 2θ, 16.3°±0.1° 2θ, 18.1°±0.1° 2θ, 19.9°±0.1° 2θ, and 22.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) comprises at least eight characteristic peaks selected from the group consisting of 8.2°±0.1° 2θ, 10.1°±0.1° 2θ, 12.7°±0.1° 2θ, 13.3°±0.1° 2θ, 15.2°±0.1° 2θ, 16.3°±0.1° 2θ, 18.1°±0.1° 2θ, 19.9°±0.1° 2θ, and 22.2°±0.1° 2θ.

In some embodiments, polymorph Form B of (R)-(2-(3-((((2-ethylbutanoyl)oxy)methoxy)carbonyl)-2-hydroxyphenyl)-1-propionamidoethyl)boronic acid citrate (Compound 1 citrate coordination complex) has a single endotherm in DSC having an onset at about 136.0° C.

TABLE 2

| Form B Characteristic XRPD Signals (2θ, Cu Kα1) | |
|---|---|
| Angle 2-Theta ° | Intensity, normalized |
| 7.4 | 26.36 |
| 8.2 | 23.50 |

TABLE 2-continued

| Form B Characteristic XRPD Signals (2θ, Cu Kα1) | |
|---|---|
| Angle 2-Theta ° | Intensity, normalized |
| 10.1 | 100.00 |
| 12.7 | 66.43 |
| 13.3 | 34.35 |
| 14.5 | 14.84 |
| 14.8 | 3.39 |
| 15.2 | 20.94 |
| 15.6 | 8.11 |
| 16.3 | 65.90 |
| 18.1 | 65.65 |
| 18.7 | 2.81 |
| 19.2 | 2.32 |
| 19.6 | 11.98 |
| 19.9 | 54.81 |
| 20.2 | 7.38 |
| 20.7 | 15.69 |
| 21.5 | 9.42 |
| 21.9 | 8.20 |
| 22.2 | 15.65 |
| 22.7 | 8.93 |
| 23.3 | 1.90 |
| 24.3 | 4.48 |
| 24.9 | 1.28 |
| 25.2 | 12.66 |
| 25.5 | 2.91 |
| 25.9 | 5.02 |
| 26.2 | 4.52 |
| 26.7 | 4.19 |
| 27.0 | 1.47 |
| 27.7 | 2.31 |
| 28.6 | 5.90 |

Pharmaceutical Composition

Disclosed herein is a pharmaceutical composition comprising:

(i) a Compound 1 ester coordination complex of Formula (I), or a pharmaceutically acceptable salt or solvate thereof; and (ii) ceftibuten:

Formula (I)

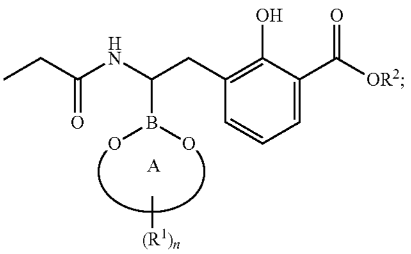

wherein:

Ring A is a 4- to 8-membered heterocycloalkyl optionally comprising 1 or 2 additional heteroatoms selected from the group consisting of O, N, and S;

each $R^1$ is independently halogen, —CN, —OH, -L-$OR^a$, -L-$NR^cR^d$, -L-C(═O)$R^a$, -L-C(═O)$OR^b$, -L-C(═O)$NR^cR^d$, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;

or two $R^1$ on the same atom are taken together to form an oxo;

n is 0, 1, 2, 3, 4, 5, or 6;

$R^2$ is hydrogen, $R^4$, —$(R^3)_q OR^4$, —$(R^3)_q O(R^3)_q OR^4$, —$R^3$OC(═O)$R^4$, —$R^3$OC(═O)$OR^4$, —$R^3$OC(═O)$NHR^5$, or —$R^3$OC(═O)$N(R^5)_2$;

each q is independently 2, 3, 4, 5, or 6;

each $R^3$ is independently —$CH_2$—, —$CH(CH_3)$—, —$C(CH_3)_2$—, or 1,1-cyclopropylene;

$R^4$ is $C_1$-$C_{12}$alkyl, $C_1$-$C_{12}$haloalkyl, $C_1$-$C_{12}$hydroxyalkyl, $C_1$-$C_{12}$aminoalkyl, $C_1$-$C_{12}$alkoxyalkyl, $C_2$-$C_{12}$alkenyl, $C_2$-$C_{12}$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;

each R is independently $C_1$-$C_{12}$alkyl, $C_1$-$C_{12}$haloalkyl, $C_1$-$C_{12}$hydroxyalkyl, $C_1$-$C_{12}$aminoalkyl, $C_1$-$C_{12}$alkoxyalkyl, $C_2$-$C_{12}$alkenyl, $C_2$-$C_{12}$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;

or two R are taken together with the nitrogen to which they are attached to form a heterocycloalkyl independently optionally substituted with one or more R;

each $R^a$ is independently $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;

each $R^b$ is independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;

$R^c$ and $R^d$ are each independently hydrogen, $C_1$-$C_6$alkyl, $C_1$-$C_6$haloalkyl, $C_1$-$C_6$hydroxyalkyl, $C_1$-$C_6$aminoalkyl, $C_1$-$C_6$heteroalkyl, $C_2$-$C_6$alkenyl, $C_2$-$C_6$alkynyl, -L-cycloalkyl, -L-heterocycloalkyl, -L-aryl, or -L-heteroaryl; wherein each alkyl, alkenyl, alkynyl, cycloalkyl, heterocycloalkyl, aryl, and heteroaryl is independently optionally substituted with one or more R;

or $R^c$ and $R^d$ are taken together with the atom to which they are attached to form a heterocycloalkyl independently optionally substituted with one or more R; and L is absent or $C_1$-$C_3$alkylene independently optionally substituted with one or more R;

each R is independently halogen, —CN, —OH, —$SF_5$, —SH, —S(═O)$C_1$-$C_3$alkyl, —$S(═O)_2C_1$-$C_3$alkyl, —$S(═O)_2NH_2$, —$S(═O)_2NHC_1$-$C_3$alkyl, —$S(═O)_2N(C_1$-$C_3$alkyl$)_2$, —S(═O)(═$NC_1$-$C_3$alkyl)($C_1$-$C_3$alkyl), —$NH_2$, —$NHC_1$-$C_3$alkyl, —$N(C_1$-$C_3$alkyl$)_2$, —N═S(═O)$(C_1$-$C_3$alkyl$)_2$, —C(═O)$C_1$-$C_3$alkyl, —C(═O)OH, —C(═O)$OC_1$-$C_3$alkyl, —C(═O)$NH_2$, —C(═O)$NHC_1$-$C_3$alkyl, —C(═O)$N(C_1$-$C_3$alkyl$)_2$, —P(═O)$(C_1$-$C_3$alkyl$)_2$, $C_1$-$C_3$alkyl, $C_1$-$C_3$alkoxy, $C_1$-$C_3$haloalkyl, $C_1$-$C_3$haloalkoxy, $C_1$-$C_3$hydroxyalkyl, $C_1$-$C_3$aminoalkyl, $C_1$-$C_3$heteroalkyl, or $C_3$-$C_6$cycloalkyl;

or two R on the same atom form an oxo.

In some embodiments, ceftibuten is in the form of ceftibuten dihydrate.

Disclosed herein is a pharmaceutical composition comprising:

(i) a compound that is (R)-(2-(3-((((2-ethylbutanoyl)oxy)methoxy)carbonyl)-2-hydroxyphenyl)-1-propionamidoethyl)boronic acid citrate coordination complex, or a pharmaceutically acceptable salt or solvate thereof; and (ii) ceftibuten.

In some embodiments, ceftibuten is in the form of ceftibuten dihydrate.

In some embodiments of the pharmaceutical composition, the compound is (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the compound is:

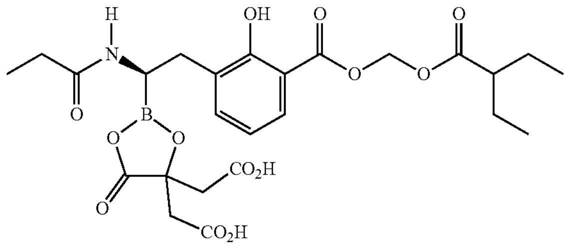 [SMILES: CCC(=O)N[C@@H](Cc1cccc(C(=O)OCOC(=O)C(CC)CC)c1O)B1OC(=O)C(CC(=O)O)(CC(=O)O)O1]

or a pharmaceutically acceptable salt or solvate thereof.

In some embodiments of the pharmaceutical composition, the compound is:

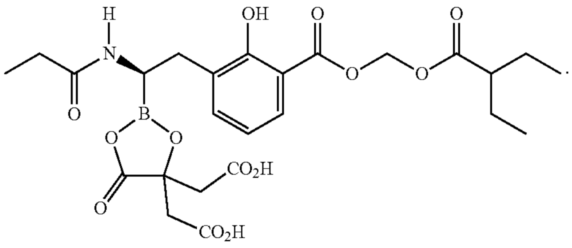 [SMILES: CCC(=O)N[C@@H](Cc1cccc(C(=O)OCOC(=O)C(CC)CC)c1O)B1OC(=O)C(CC(=O)O)(CC(=O)O)O1]

.

In some embodiments of the pharmaceutical composition, the compound is:

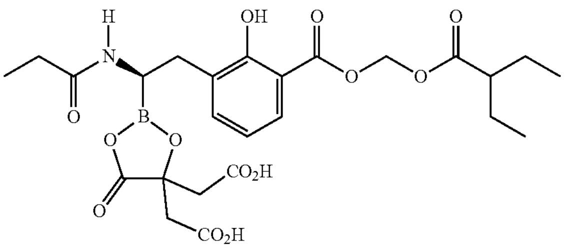 [SMILES: CCC(=O)N[C@@H](Cc1cccc(C(=O)OCOC(=O)C(CC)CC)c1O)B1OC(=O)C(CC(=O)O)(CC(=O)O)O1]

as a monosodium salt.

In some embodiments of the pharmaceutical composition, the compound is:

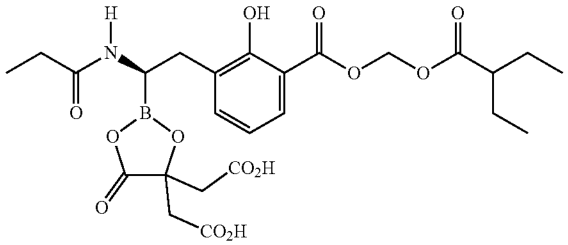 [SMILES: CCC(=O)N[C@@H](Cc1cccc(C(=O)OCOC(=O)C(CC)CC)c1O)B1OC(=O)C(CC(=O)O)(CC(=O)O)O1]

as a disodium salt.

In some embodiments of the pharmaceutical composition, the compound is:

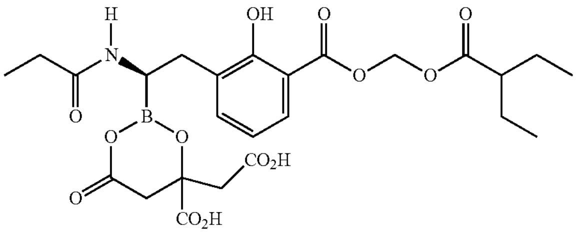 [SMILES: CCC(=O)N[C@@H](Cc1cccc(C(=O)OCOC(=O)C(CC)CC)c1O)B1OC(=O)CC(CC(=O)O)(C(=O)O)O1]

or a pharmaceutically acceptable salt or solvate thereof.

In some embodiments of the pharmaceutical composition, the compound is:

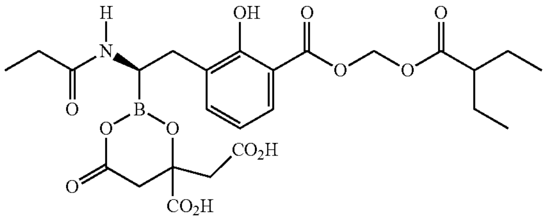 [SMILES: CCC(=O)N[C@@H](Cc1cccc(C(=O)OCOC(=O)C(CC)CC)c1O)B1OC(=O)CC(CC(=O)O)(C(=O)O)O1]

.

In some embodiments of the pharmaceutical composition, the compound is:

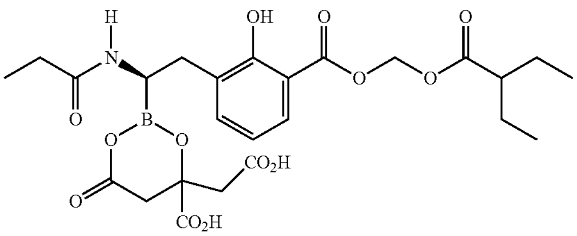

as a monosodium salt.

In some embodiments of the pharmaceutical composition, the compound is:

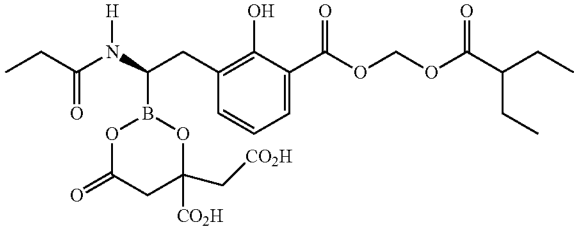 [SMILES: CCC(=O)N[C@@H](Cc1cccc(C(=O)OCOC(=O)C(CC)CC)c1O)B1OC(=O)CC(CC(=O)O)(C(=O)O)O1]

as a disodium salt.

In some embodiments of the pharmaceutical composition, (R)-(2-(3-((((2-ethylbutanoyl)oxy)methoxy)carbonyl)-2-hydroxyphenyl)-1-propionamidoethyl)boronic acid citrate coordination complex, or a pharmaceutically acceptable salt solvate thereof, is crystalline.

Disclosed herein is a pharmaceutical composition comprising:

(i) a crystalline form of a compound that is (R)-(2-(3-((((2-ethylbutanoyl)oxy)methoxy)carbonyl)-2-hydroxyphenyl)-1-propionamidoethyl)boronic acid citrate coordination complex, or a pharmaceutically acceptable salt or solvate thereof; and (ii) ceftibuten.

In some embodiments, ceftibuten is in the form of ceftibuten dihydrate.

In some embodiments of the pharmaceutical composition, the compound is (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the compound is:

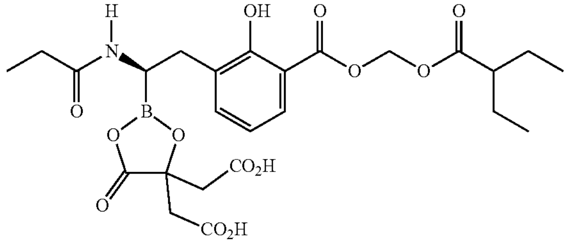 [SMILES: CCC(=O)N[C@@H](Cc1cccc(C(=O)OCOC(=O)C(CC)CC)c1O)B1OC(=O)C(CC(=O)O)(CC(=O)O)O1]

or a pharmaceutically acceptable salt or solvate thereof.

In some embodiments of the pharmaceutical composition, the compound is:

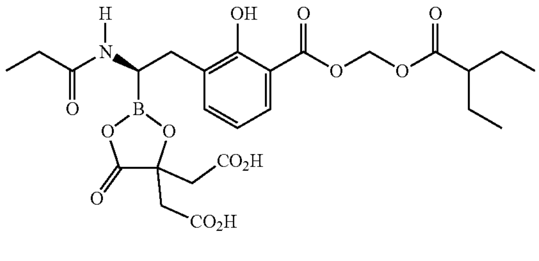 [SMILES: CCC(=O)N[C@@H](Cc1cccc(C(=O)OCOC(=O)C(CC)CC)c1O)B1OC(=O)C(CC(=O)O)(CC(=O)O)O1]

.

In some embodiments of the pharmaceutical composition, the compound is:

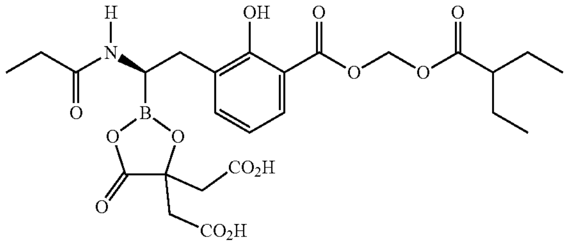

as a monosodium salt.

In some embodiments of the pharmaceutical composition, the compound is:

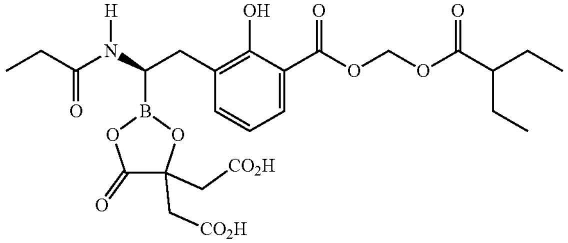 [SMILES: CCC(=O)N[C@@H](Cc1cccc(C(=O)OCOC(=O)C(CC)CC)c1O)B1OC(=O)C(CC(=O)O)(CC(=O)O)O1]

as a disodium salt.

In some embodiments of the pharmaceutical composition, the compound is:

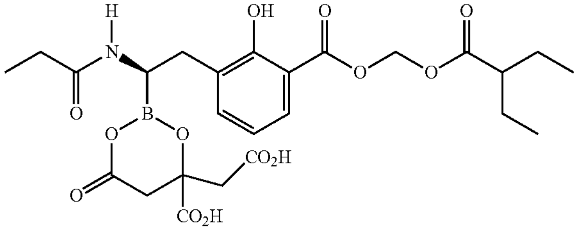 [SMILES: CCC(=O)N[C@@H](Cc1cccc(C(=O)OCOC(=O)C(CC)CC)c1O)B1OC(=O)CC(CC(=O)O)(C(=O)O)O1]

or a pharmaceutically acceptable salt or solvate thereof.

In some embodiments of the pharmaceutical composition, the compound is:

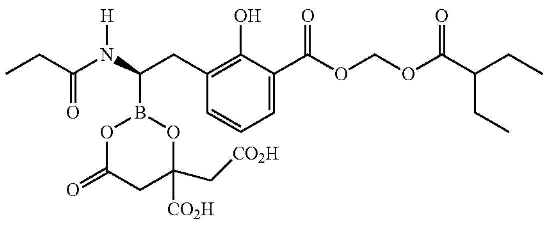 [SMILES: CCC(=O)N[C@@H](Cc1cccc(C(=O)OCOC(=O)C(CC)CC)c1O)B1OC(=O)CC(CC(=O)O)(C(=O)O)O1]

.

In some embodiments of the pharmaceutical composition, the compound is:

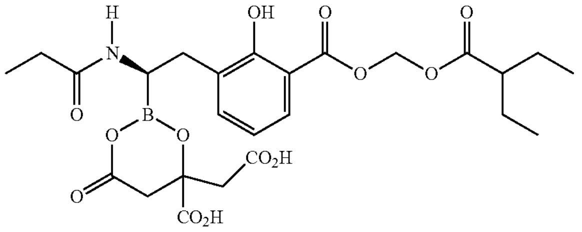

as a monosodium salt.

In some embodiments of the pharmaceutical composition, the compound is:

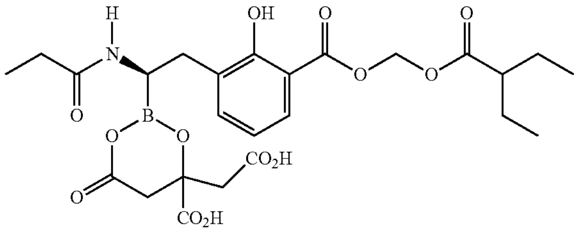 [SMILES: CCC(=O)N[C@@H](Cc1cccc(C(=O)OCOC(=O)C(CC)CC)c1O)B1OC(=O)CC(CC(=O)O)(C(=O)O)O1]

as a disodium salt.

In some embodiments of the pharmaceutical composition, the compound and ceftibuten are formulated in a single dosage form.

In some embodiments of the pharmaceutical composition, the crystalline form and ceftibuten are formulated in a single dosage form.

In some embodiments of the pharmaceutical composition, the single dosage form is a capsule.

In some embodiments of the pharmaceutical composition, the single dosage form is a tablet.

In some embodiments of the pharmaceutical composition, the single dosage form comprises the compound and ceftibuten dihydrate in a ratio adjusted to correspond to between about 1:1 and about 1:4 of

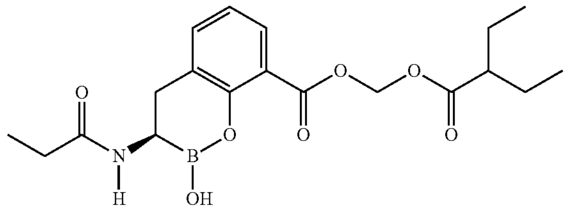 [SMILES: CCC(=O)N[C@H]1Cc2cccc(C(=O)OCOC(=O)C(CC)CC)c2OB1O]

and ceftibuten.

In some embodiments of the pharmaceutical composition, the single dosage form comprises the compound and ceftibuten dihydrate in a ratio adjusted to correspond to between about 1:1 and about 1:3 of

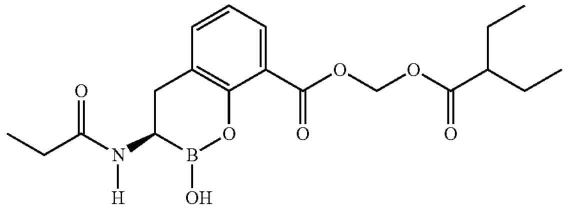 [SMILES: CCC(=O)N[C@H]1Cc2cccc(C(=O)OCOC(=O)C(CC)CC)c2OB1O]

and ceftibuten.

In some embodiments of the pharmaceutical composition, the single dosage form comprises the compound and ceftibuten dihydrate in a ratio adjusted to correspond to between about 1:1 and about 1:2 of

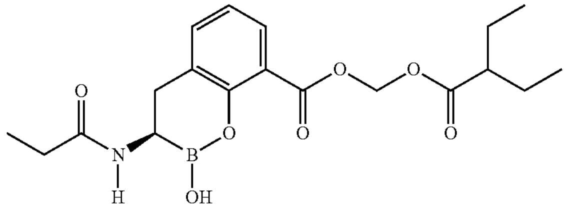 [SMILES: CCC(=O)N[C@H]1Cc2cccc(C(=O)OCOC(=O)C(CC)CC)c2OB1O]

and ceftibuten.

In some embodiments of the pharmaceutical composition, the single dosage form comprises the compound and ceftibuten dihydrate in a ratio adjusted to correspond to between about 1:1 and about 1:1.5 of

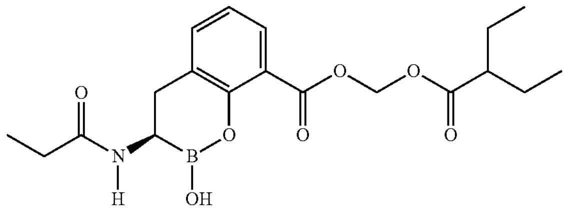 [SMILES: CCC(=O)N[C@H]1Cc2cccc(C(=O)OCOC(=O)C(CC)CC)c2OB1O]

and ceftibuten.

In some embodiments of the pharmaceutical composition, the single dosage form comprises the compound and ceftibuten dihydrate in a ratio adjusted to correspond to about 1:1 of

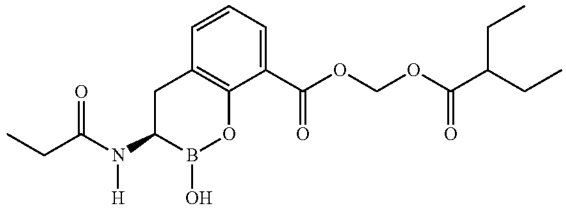 [SMILES: CCC(=O)N[C@H]1Cc2cccc(C(=O)OCOC(=O)C(CC)CC)c2OB1O]

and ceftibuten.

In some embodiments of the pharmaceutical composition, the single dosage form comprises between about 100 mg and about 250 mg of ceftibuten dihydrate.

In some embodiments of the pharmaceutical composition, the single dosage form comprises between about 150 mg and about 250 mg of ceftibuten dihydrate.

In some embodiments of the pharmaceutical composition, the single dosage form comprises between about 150 mg and about 200 mg of ceftibuten dihydrate.

In some embodiments of the pharmaceutical composition, the single dosage form comprises between about 200 mg and about 250 mg of ceftibuten dihydrate.

In some embodiments of the pharmaceutical composition, the single dosage form comprises between about 210 mg and about 240 mg of ceftibuten dihydrate.

In some embodiments of the pharmaceutical composition, the single dosage form comprises between about 210 mg and about 220 mg of ceftibuten dihydrate.

In some embodiments of the pharmaceutical composition, the single dosage form comprises between about 220 mg and about 230 mg of ceftibuten dihydrate.

In some embodiments of the pharmaceutical composition, the single dosage form comprises about 100 mg of ceftibuten dihydrate.

In some embodiments of the pharmaceutical composition, the single dosage form comprises about 110 mg of ceftibuten dihydrate.

In some embodiments of the pharmaceutical composition, the single dosage form comprises about 120 mg of ceftibuten dihydrate.

In some embodiments of the pharmaceutical composition, the single dosage form comprises about 130 mg of ceftibuten dihydrate.

In some embodiments of the pharmaceutical composition, the single dosage form comprises about 140 mg of ceftibuten dihydrate.

In some embodiments of the pharmaceutical composition, the single dosage form comprises about 150 mg of ceftibuten dihydrate.

In some embodiments of the pharmaceutical composition, the single dosage form comprises about 160 mg of ceftibuten dihydrate.

In some embodiments of the pharmaceutical composition, the single dosage form comprises about 170 mg of ceftibuten dihydrate.

In some embodiments of the pharmaceutical composition, the single dosage form comprises about 180 mg of ceftibuten dihydrate.

In some embodiments of the pharmaceutical composition, the single dosage form comprises about 190 mg of ceftibuten dihydrate.

In some embodiments of the pharmaceutical composition, the single dosage form comprises about 200 mg of ceftibuten dihydrate.

In some embodiments of the pharmaceutical composition, the single dosage form comprises about 210 mg of ceftibuten dihydrate.

In some embodiments of the pharmaceutical composition, the single dosage form comprises about 220 mg of ceftibuten dihydrate.

In some embodiments of the pharmaceutical composition, the single dosage form comprises about 230 mg of ceftibuten dihydrate.

In some embodiments of the pharmaceutical composition, the single dosage form comprises ceftibuten dihydrate in an amount adjusted to correspond to 200 mg of ceftibuten.

In some embodiments of the pharmaceutical composition, the single dosage form comprises between about 50 mg and about 100 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises between about 60 mg and about 90 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises between about 70 mg and about 80 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 72 mg of (R)-(2-(3-((((2-ethylbutanoyl)oxy)methoxy)carbonyl)-2-hydroxyphenyl)-1-propionamidoethyl)boronic acid citrate.

In some embodiments of the pharmaceutical composition, the single dosage form comprises between about 200 mg and about 350 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises between about 260 mg and about 310 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises between about 270 mg and about 300 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises between about 280 mg and about 290 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 50 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 60 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 70 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 80 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 90 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 100 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 110 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 120 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 130 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 140 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 150 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 160 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 170 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 180 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 190 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 200 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 210 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 220 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 230 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 240 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 250 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 260 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 270 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 280 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 290 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 300 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises about 310 mg of (R)-(2-(3-((((2-ethylbutanoyl)oxy)methoxy)carbonyl)-2-hydroxyphenyl)-1-propionamidoethyl)boronic acid citrate coordination complex.

In some embodiments of the pharmaceutical composition, the single dosage form comprises (R)-(2-(3-((((2-ethylbutanoyl)oxy)methoxy)carbonyl)-2-hydroxyphenyl)-1-propionamidoethyl)boronic acid citrate coordination complex in an amount adjusted to correspond to 200 mg of (Compound 1)

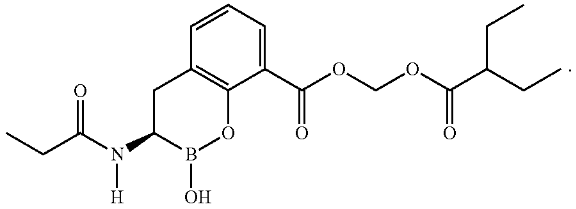

In some embodiments of the pharmaceutical composition, the single dosage form comprises (R)-(2-(3-((((2-ethylbutanoyl)oxy)methoxy)carbonyl)-2-hydroxyphenyl)-1-propionamidoethyl)boronic acid citrate coordination complex in an amount adjusted to correspond to 50 mg of (Compound 1)

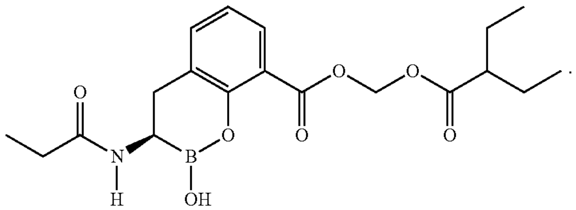

Methods of Treatment

Disclosed herein are methods for inhibiting bacterial growth, by, e.g., reducing bacterial resistance to a β-lactam antibiotic, such methods comprising contacting a bacterial cell culture, or a bacterially infected cell culture, tissue, or organism, the method comprising administering a pharmaceutical composition comprising Compound 1 citrate coordination complex, or a pharmaceutically acceptable salt or solvate thereof. In some embodiments, the pharmaceutical composition further comprises an antibiotic. In some embodiments, the pharmaceutical composition further comprises a beta-lactam antibiotic. In some embodiments, the beta-lactam antibiotic is ceftibuten. In some embodiments, the beta-lactam antibiotic is ceftibuten dihydrate.

In some embodiments, the bacteria to be inhibited by administration of a compound described herein or a pharmaceutical composition described herein, are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)).

These methods are useful for inhibiting bacterial growth in a variety of contexts. In certain embodiments, the compound described herein or the pharmaceutical composition described herein is administered to an experimental cell culture in vitro to prevent the growth of beta-lactam resistant bacteria. In certain other embodiments, the compound described herein or the pharmaceutical composition described herein is administered to a mammal, including a human, to prevent the growth of beta-lactam resistant bacteria in vivo. In some embodiments, the method comprises administering a therapeutically effective amount of a beta-lactamase inhibitor, as a compound described herein or the pharmaceutical composition described herein, for a therapeutically effective period of time to a mammal, including a human. Preferably, the beta-lactamase inhibitor is administered in the form of a pharmaceutical composition as herein. In some embodiments, an antibiotic is co-administered with the beta-lactamase inhibitor. In some embodiments, the antibiotic is a beta-lactam antibiotic. In some embodiments, the beta-lactam antibiotic is ceftibuten. In some embodiments, the beta-lactam antibiotic is ceftibuten dihydrate.

Disclosed herein are methods of treating a bacterial infection, the method comprising administering to a subject a compound described herein or a pharmaceutical composition described herein. In some embodiments, the bacterial infection is an upper or lower respiratory tract infection, a urinary tract infection, an intra-abdominal infection, or a skin infection.

In some embodiments, the bacterial infection is caused by carbapenem-resistant Enterobacteriaceae (CRE) or extended-spectrum beta-lactamase (ESBL) producing gram-negative bacteria.

In some embodiments, the bacterial infection is acute bacterial exacerbations of chronic bronchitis (ABECB), acute bacterial otitis media, pharyngitis, or tonsillitis.

In some embodiments, the bacterial infection is pneumonia, urinary tract infections, enteritis, or gastroenteritis.

In some embodiments, the bacterial infection is otitis media, strep throat, pneumonia, urinary tract infections, gonorrhea, or Lyme disease.

In some embodiments, the infection that is treated comprises a bacteria that includes *Elizabethkingia meningoseptica, Pseudomonas aeruginosa, Pseudomonas luorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella lexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides* ovalus, *Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus.*

In some embodiments, the infection that is treated comprises a bacteria that includes *Escherichia coli, Citrobacter freundii, Salmonella typhimurium, Salmonella typhi, Salmonella paratyphi, Salmonella enteritidis, Shigella dysenteriae, Shigella lexneri, Shigella sonnei, Enterobacter cloacae, Enterobacter aerogenes, Klebsiella pneumoniae, Klebsiella oxytoca, Serratia marcescens, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainluenzae, Haemophilus haemolyticus, Haemophilus parahaemolyticus, Haemophilus ducreyi, Pasteurella multocida, Pasteurella haemolytica, Branhamella catarrhalis, Borrelia burgdorferi, Vibrio cholerae, Vibrio parahaemolyticus, Legionella pneumophila, Neisseria gonorrhoeae, Neisseria meningitidis, Moraxella, Streptococcus pneumoniae, Streptococcus agalactiae*, and *Streptococcus pyogenes.*

In some embodiments, the infection that is treated comprises a bacteria that includes *Elizabethkingia meningoseptica, Pseudomonas aeruginosa, Pseudomonas luorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella lexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis,*

*Yersinia intermedia, Haemophilus influenzae, Haemophilus parainluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, or *Bacteroides splanchnicus*.

In some embodiments, the infection that is treated comprises a bacteria that includes *Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Vibrio cholerae, Vibrio parahaemolyticus, Legionella pneumophila, Listeria monocytogenes, Neisseria gonorrhoeae*, and *Neisseria meningitidis, Moraxella.*

EXAMPLES

Analytical Methods

Mass Spectrometry (MS)

The mass spectrum of Compound 1 citrate coordination complex was obtained using a Waters Single Quad 3100 Mass Detector operating in Electrospray Ionization (ESI) negative ion polarity mode. The sample was prepared in acetonitrile at a concentration of approximately 87 μg/mL. The sample solution was infused directly from the UPLC system into mass spectrometer and the tuning parameters were optimized to the compound.

The sample of Compound 1 citrate coordination complex generated a peak with m/z 564.04 for the [M−H]− is in agreement with the monoisotopic mass of the proposed molecular formula of $C_{25}H_{32}BNO_{13}$ for Compound 1. The molecular mass of Compound 1 citrate coordination complex is 565.34 Da and the exact mass is 564.04 Da.

X-Ray Powder Diffraction

XRPD patterns were collected using a Bruker D8 Advance using Cu Kα radiation of 40 kV/40 mA. Data were collected with a LynxEye detector in Bragg-Brentano reflection geometry with a 0.02°2q step size, 37 s step time over 2.5-50°2q range. The powder samples were measured in 0.05 mm deep silicon single-crystal sample holders covered with a Kapton foil to protect them from moisture. The samples were placed in an inert atmosphere environment ($N_2$-filled glovebox) but no other special treatment was used in preparing the samples other than the application of slight pressure to obtain a flat surface. All samples were rotated during the measurement.

Polarized Light Microscopy (PLM)

Polarized light microscopy was performed using a Leica MZ12.5 or Fisher Scientific Stereomaster stereomicroscope. Samples were observed using 0.8-10× objectives with crossed polarizers.

Differential Scanning Calorimetry (DSC) Analysis

Conventional DSC experiments were performed by using a Q100 (TA® Instruments, New Castle, Delaware, USA) instrument equipped with a refrigerated cooling system (RCS90). The sample cell was purged with dry nitrogen at a flow rate of 50 mL/min. Accurately weighed samples (2-5 mg) placed in TZero pans with a pin hole were scanned at a heating rate of 10° C./min over a desired temperature range.

Dynamic Vapor Sorption (DVS) Analysis

Moisture sorption/desorption data were collected on a DVS-intrinsic vapor sorption analyzer (Surface Measurement Systems NA, Allentown, PA, USA) and operated with DVS-intrinsic control software (Version 1.0.5.1). Samples were not dried prior to analysis. Sorption and desorption data were collected over a range from 5% to 98% relative humidity (RH) via 10% RH increments under a nitrogen purge. The equilibrium criterion used for analysis was less than 0.005% weight change in 10 min with a maximum equilibration time of 3 h.

Thermogravimetric Analysis (TGA)

TGA was performed using a Discovery TGA 5500 (TA® Instruments, New Castle, Delaware, USA) instrument operating with TRIOS software (Version 5.0). The sample was placed in an aluminum pan. The sample cell was purged with dry nitrogen at a flow rate of 15 mL/min. A heating rate of 10° C./min from 25-350° C. was used in all the experiments.

Nuclear Magnetic Resonance (NMR)

All 1D and 2D NMR data were collected at 300K using a Bruker-Biospin 5 mm gradient broadband probe on a Bruker-Biospin AVANCE 500 MHz NMR spectrometer. The 1D proton, 1D carbon and 1D boron spectra were acquired at 500 MHz, 125 MHz, and 160 MHz, respectively. The spectra were referenced using the tetramethylsilane resonance and set equal to 0.0 ppm for both $^{1}H$ and $^{13}C$. All chemical shifts (δ) are given in ppm using TMS as a reference, and J values are given in Hz. Chemical shifts (δ) downfield from the reference standard were assigned as positive values.

Example 1: Preparation and Characterization of Compound 1 Citrate Coordination Complex, Amorphous.

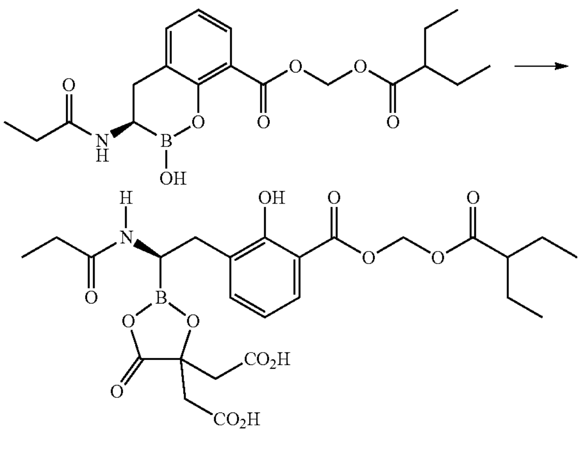

Figure 10:
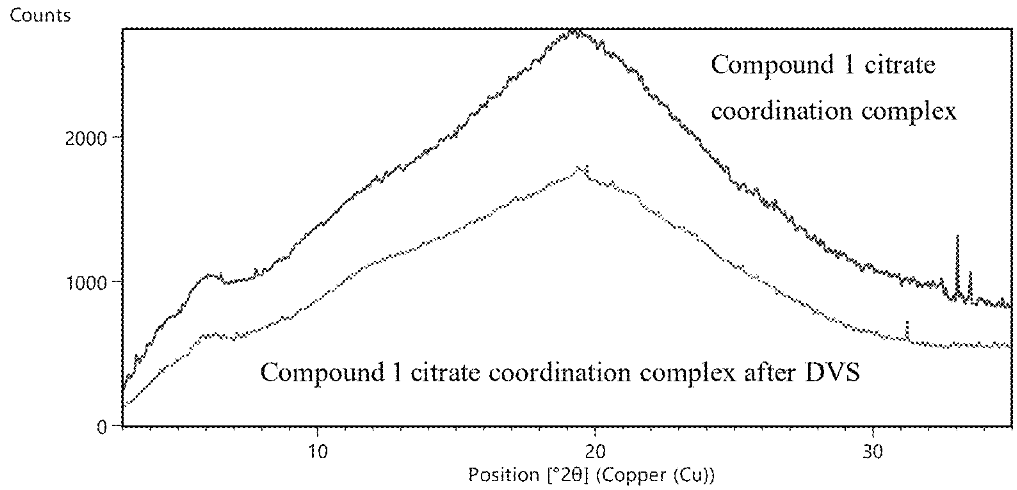
FIG. 10 shows the XRPD pattern for amorphous Compound 1 citrate coordination complex.

2-[4-(carboxymethyl)-2-[(1R)-2-[3-({[(2-ethylbutanoyl)oxy]methoxy}carbonyl)-2-hydroxyphenyl]-1-propanamidoethyl]-5-oxo-1,3,2-dioxaborolan-4-yl]acetic acid, Form A, was dissolved in isopropyl acetate at 75° C. Once all the solid had completely dissolved the hot solution was transferred to room temperature heptane resulting in a precipitate. The solid was filtered and washed with heptane. The solid was dried and analyzed by XRPD indicating the material was amorphous (FIG. 10).

Example 2: Preparation and Characterization of Compound 1 Citrate Coordination Complex, Form A.

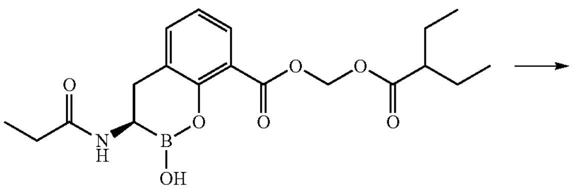

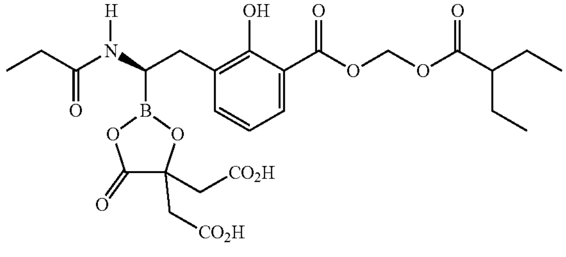

((2-Ethylbutanoyl)oxy)methyl (R)-2-hydroxy-3-propionamido-3,4-dihydro-2H-benzo[e][1,2]oxaborinine-8-carboxylate (Compound 1, 125 grams, 1 eq, 95.0 w/w %) was dissolved in acetonitrile (1250 ml, 10 volumes) followed by addition of citric acid (anhydrous, 54.4 g, 1 eq) to generate a heterogenous solution. The mixture was agitated at ambient temperature for two hours or until a homogenous solution was formed. Acetonitrile was distilled under vacuum to 3-4 volumes followed by addition of 10 volumes of isopropyl acetate. The batch was distilled, under vacuum, to 3-4 volumes followed by addition of 10 volumes of isopropyl acetate two more times or until the water content was below 1000 ppm. The volume of the batch was adjusted to 9-10 volumes of isopropyl acetate and then heated to 65° C. The batch was cooled to 45-50° C. and seeded with 0.1 w/w % Compound 1 Citrate, Form A, and held for 30 min for crystals to form. Once a seed bed formed, the batch was cooled to 20-25° C. and held for 16 h. The batch was cooled to 5° C., held for 2 h, and then filtered, and washed with cold (5° C.) isopropyl acetate/heptane (3x3v, 3/1 v/v). The solid was dried on the filter and then under vacuum to constant weight to yield 144 grams of a white solid. The process above provided Compound 1 citrate coordination complex, Form A, in 90% yield and UHPLC purity of 99.9% and a qNMR assay purity of 99.3 w/w % (ethylene carbonate as internal standard).

Alternative Synthesis of Compound 1 Citrate Coordination Complex, Form A

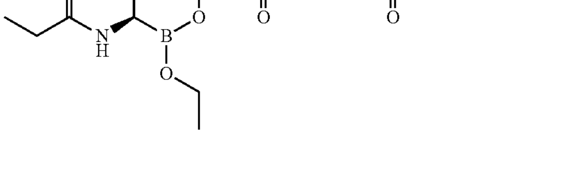

-continued

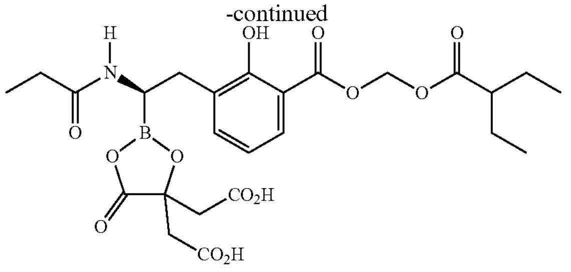

2.105 g of Compound 1 ethanolate and 0.968 g of citric acid (1:1 molar ratio) were added into a 100 mL round-bottom flask with 15 mL of anhydrous ethyl acetate. The resulting solution was heated and maintained at 80° C. for 3.5 hours. Inert atmosphere ($N_2$ atmosphere) was maintained throughout the reaction. The resultant solution from step-1 was evaporated. The obtained glue like material was further dried by purging with $N_2$ for ~15 hours. The resultant solid from Step-2 was treated with 20 mL of diethyl ether and stirred for 1 hour. Added 20 mL of n-heptane to that suspension and stirred for another 24 hours. The solid obtained was filtered and dried at room temperature for ~2 hours.

Mass Spectrometry

The mass spectrum of Compound 1 citrate coordination complex Form A was obtained using an Agilent 6120 quadrupole LC/mass spectrometer using an electrospray ionization source. The instrument was controlled, and data analyzed, using ChemStation v.B.04.03 software. The mass spectrometer was calibrated immediately prior to analysis and was operated in positive and negative ionization mode using an Electrospray Ionization (ESI) source. Samples were prepared by dilution in HPLC grade acetonitrile at 1 mg/ml concentration and eluted with 100% acetonitrile through a pre-equilibrated HPLC column (XBridge BEH C18 Column, 130 Å, 3.5 μm, 4.6 mmx50 mm) prior to infusion into the ion source.

The mass spectrum included peaks with m z 564 for the $[M-H]^-$, and m z 588 for the $[M+Na]^+$ peak, in agreement with the monoisotopic mass of the proposed molecular formula of $C_{25}H_{32}BNO_{13}$. The molecular mass of Compound 1 citrate coordination complex Form A is 565.34 Da and the exact mass is 565.20 Da.

Nuclear Magnetic Resonance (NMR) Spectroscopy

Approximately 25 mg of Compound 1 citrate coordination complex, sample was dissolved in 1 mL of 99.9% deuterated Acetone-$d_6$ with 0.05% (v/v) tetramethylsilane, as the solvent. The following data were collected: 1D proton, 1D carbon, 1D boron, $^1$H-$^1$H gradient COSY (COrrelation SpectroscopY), $^1$H—$^{13}$C Heteronuclear Single Quantum Coherence with Distortionless Enhancement by Polarization Transfer (HSQC-DEPT), and the Heteronuclear Multiple Bond Coherence (HMBC) experiment. All 1D and 2D NMR data were collected at 300K using a Bruker-Biospin 5 mm gradient broadband probe on a Bruker-Biospin AVANCE 500 MHz NMR spectrometer. The 1D proton, 1D carbon and 1D boron spectra were acquired at 500 MHz, 125 MHz, and 160 MHz, respectively. The spectra were referenced using the tetramethylsilane resonance and set equal to 0.0 ppm for both $^1$H and $^{13}$C. The chemical shift of the boron resonance was determined by spiking the sample with methylboronic acid which was set to 31.90 ppm and Compound 1 citrate coordination complex has an $^{11}$B chemical shift of 12.88 ppm relative to methylboronic acid.

The 1D proton spectrum showed the expected chemical shifts, multiplicities and integrations that are consistent with the structure of Compound 1 citrate coordination complex. Duplicate $^{1}H$ and $^{13}C$ resonances were observed (due to the presence conformational isomers of the amide functionality). The data are summarized in Table 3.

TABLE 3

$^{1}H$ and $^{13}C$ NMR Chemical Shift Assignments for Compound 1 Citrate Coordination Complex Form A in Acetone-$d_6$ [300 K]

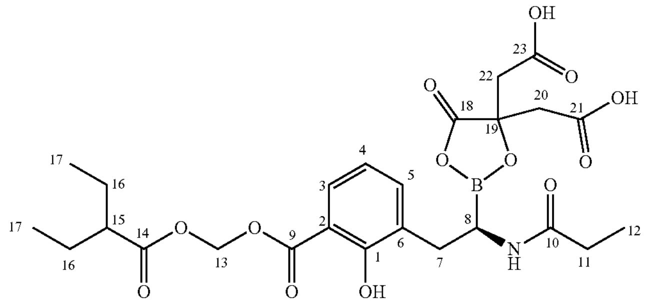 [SMILES: CCC(=O)N[C@@H](Cc1cccc(C(=O)OCOC(=O)C(CC)CC)c1O)B1OC(=O)C(CC(=O)O)(CC(=O)O)O1]

| Position No. | Proton Shift (ppm) | Integration | Proton Multiplicity (J in Hz) | Carbon Shift§ (ppm) |
|---|---|---|---|---|
| 1 | N/A | N/A | N/A | 161.3 |
| 2 | N/A | N/A | N/A | 112.02, 111.99§ |
| 3 | 7.71 | 1 | d (J = 8.0) | 128.9 |
| 4 | 6.90 | 1 | t (J = 7.7) | 120.2 |
| 5 | 7.52 | 1 | d (J = 7.4) | 138.6, 138.4§ |
| 6 | N/A | N/A | N/A | 130.7, 130.6§ |
| 7 | 3.05, 2.78, 2.96, 2.71 | 2 | m | 31.2, 30.9§ |
| 8 | 3.10, 3.04 | 1 | m | 48.4 (br) |
| 9 | N/A | N/A | N/A | 170.1 |
| 10 | N/A | N/A | N/A | 182.2, 182.0§ |
| 11 | 2.56 | 2 | m | 24.38, 24.36§ |
| 12 | 1.20, 1.18 | 3 | t (J = 7.5), t (J = 7.4) | 9.4 |
| 13 | 6.10, 6.093, 6.091, 6.08 | 2 | | 80.68, 80.66§ |
| 14 | N/A | N/A | N/A | 174.9 |
| 15 | 2.32 | 1 | m | 49.2 |
| 16 | 1.60 | 4 | m | 25.47, 25.46§ |
| 17 | 0.89 | 6 | t (J = 7.5) | 11.9 |
| 18 | N/A | N/A | N/A | 178.4, 178.3§ |
| 19 | N/A | N/A | N/A | 77.7, 77.5§ |
| 20 | 2.74, 2.72 | 2 | m | 43.7, 43.8§ |
| 21 | N/A | N/A | N/A | 170.7, 170.6§ |
| 22 | 3.09, 2.99, 2.92, 2.80 | 2 | m | 41.8, 41.7§ |
| 23 | N/A | N/A | N/A | 171.4, 171.2§ |
| 1-OH | 10.74, 10.72 | 2.76¥ | s | N/A |
| 8-NH-10 | 9.43 | 1.0 | d (J = 9.2) | N/A |
| 21, 23-OH | 10.65 | 2.76¥ | br s | N/A |

s = singlet,
t = triplet,
q = quartet,
dt = doublet of triplets,
m = multiplet,
br = broad,
ppm = parts per million.
NA = Not Applicable.
¥Integration for 1-OH and 21,23-OH.
§The splitting of 13C resonances of C2, C5, C6, C7, C10, C11, C13, C16, C18, C19, C20, C21, C22 and C23 is due to the presence of conformational isomers.
The two CH2CO2H of the boron-citric acid coordination complex are in non-equivalent environments.

Example 2. Solubility Studies of Compound 1 Citrate Coordination Complex Form A.

Visual solubility estimates for Compound 1 citrate coordination complex Form A were determined in a variety of solvents and solvent mixtures using an aliquot addition method to aid in experimental design. In general, Compound 1 citrate coordination complex Form A exhibited good solubility in the majority of the tested solvents. Low solubility (<1 mg/mL) was observed in heptane and cyclohexane. Solubility results are provided in Table 4.

TABLE 4

Solubility Estimates of Compound 1 Citrate Coordination Complex Form A at Ambient Temperature

| Solvent | Solubility (mg/mL) |
|---|---|
| Methanol | >77 |
| 1,4-Dioxane | >70 |
| Dimethylformamide | >72 |
| Acetone | >75 |
| Ethyl Acetate | >80 |
| Acetonitrile | >79 |
| Ethanol | >75 |
| 2-Propanol | >72 |
| Acetic acid | >76 |
| 4-Methyl-2-pentanone | >76 |
| Ethylene Glycol | >78 |
| Water | <7.5 |
| Dimethyl sulfoxide | >79.15 |
| 1,2-Propanediol | >19.13 |
| Pentane | <7.5- |
| Heptane | <7.5 |
| Methylcyclohexane | <7.5 |
| Toluene | <7.5 |
| Diethyl ether | <7.5 |
| Dichloromethane | >25.62 |
| Chloroform | >77.60 |
| t-butyl methyl ether | <7.5 |
| Tetrahydrofuran | >78.50 |

Solubilities are calculated based on the total solvent used to give a solution; actual solubilities may be greater because of the volume of the solvent portions utilized or a slow rate of dissolution. Solubilities are rounded to the nearest mg/mL.

Example 3. XRPD Characterization of Compound 1 Citrate Coordination Complex Form A.

XRPD analysis indicates Compound 1 citrate Form A from Example 1 is composed of a crystalline material. FIG. 2 shows the XRPD pattern for Compound 1 citrate Form A.

Example 4. Thermal Analysis of Compound 1 Citrate Coordination Complex Form A.

Figure 4:
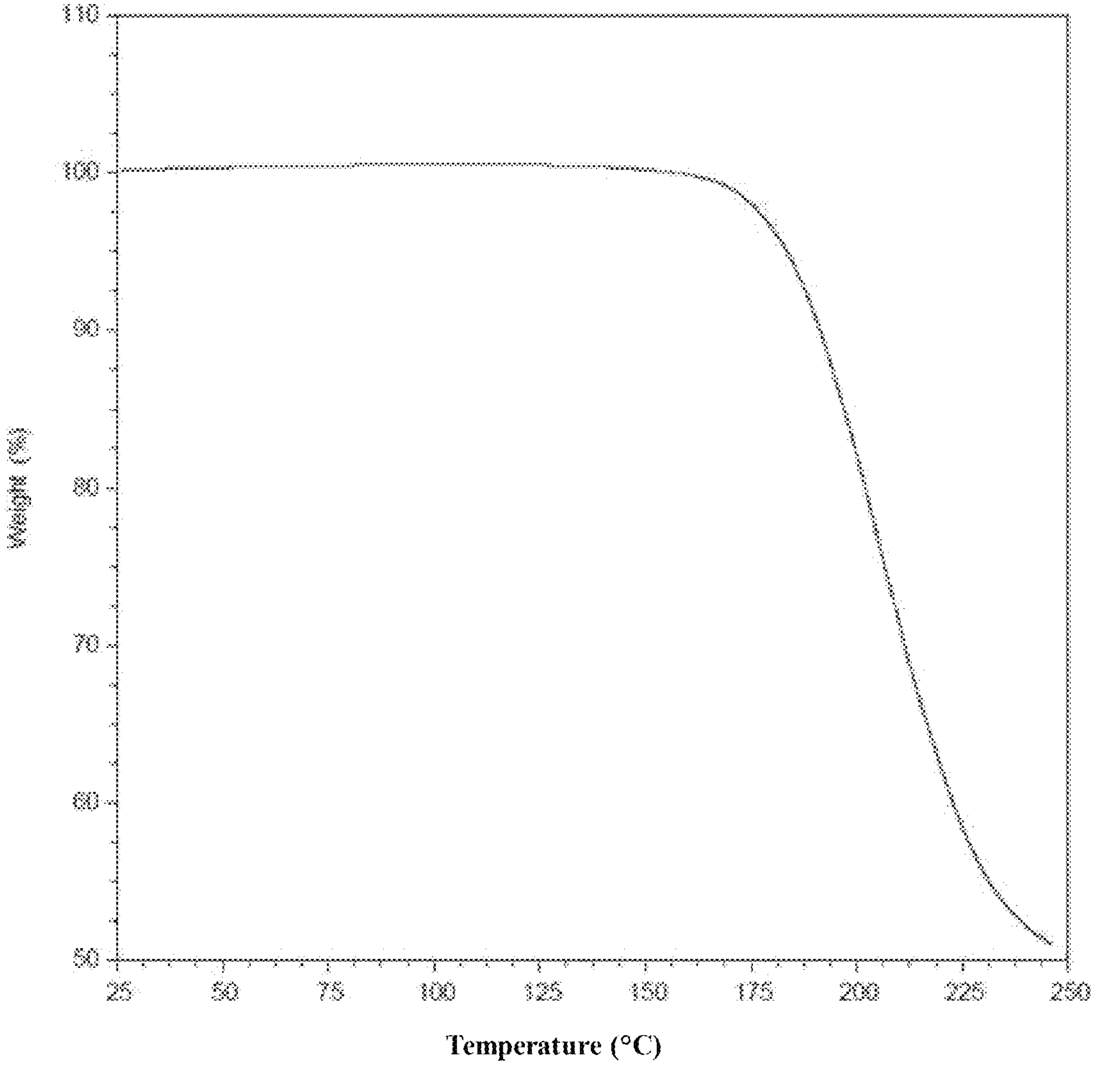
FIG. 4 shows the TGA thermogram of Compound 1 citrate coordination complex Form A.

Thermal analysis of Compound 1 citrate coordination complex Form A is presented in FIG. 3 and FIG. 4. The DSC thermogram of Compound 1 citrate coordination complex Form A Form A (FIG. 3) exhibits a sharp peak, coincident with the onset of a single endotherm, at 146.22° C. (peak maximum). A weight loss of 0.1% is observed in the TGA (FIG. 4) between 24.8 and 120° C.

Example 5: Dynamic Vapor Sorption (DVS) Analysis of Compound 1 Citrate Coordination Complex Form A.

Figure 5:
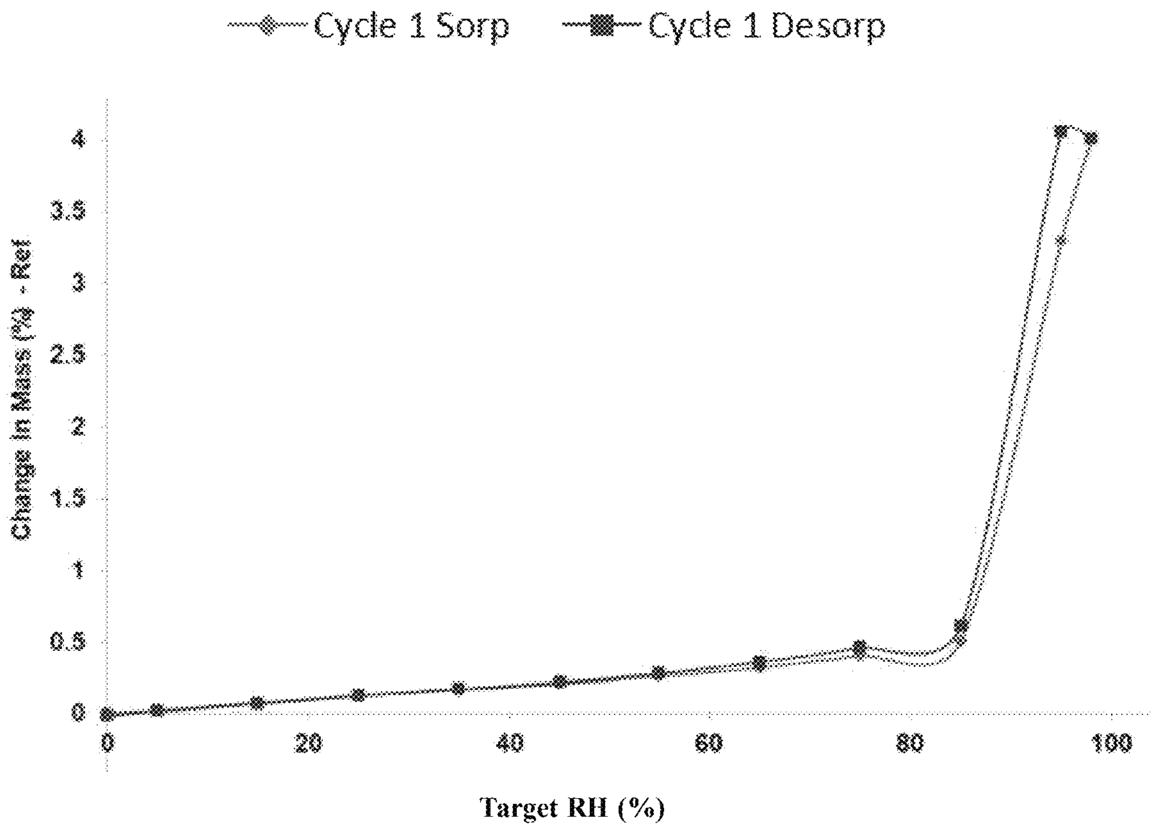
FIG. 5 shows the DVS analysis of Compound 1 citrate coordination complex Form A.

DVS analysis of Compound 1 citrate coordination complex Form A. Form A was conducted from 0% relative humidity (RH) to 98% RH and back to 0% RH at 10% RH increments FIG. 5. With increasing RH, the sample showed 0.5 wt % gain between 0% RH and 85% RH suggesting Form A is non-hygroscopic from 0-85% RH. Above 85% RH Compound 1 citrate coordination complex Form A. Form A sample show 4.0% weight gain and remained as a solid. Decreasing the RH from 98% to 0% the sample displayed minimal hysteresis and the sample remained crystalline, as Form A, by XRPD. These data are summarized in Table 5.

TABLE 5

Time course of water absorption for Compound 1 citrate coordination complex Form A under increasing relative humidity

| Target | Change In Mass (%)-ref | | |
|---|---|---|---|
| RH (%) | Sorption | Desorption | Hysteresis |
| 0.0 | 0.000 | −0.023 | |
| 5.0 | 0.019 | 0.012 | −0.006 |
| 15.0 | 0.073 | 0.065 | −0.008 |
| 25.0 | 0.121 | 0.119 | −0.003 |
| 35.0 | 0.159 | 0.167 | 0.008 |
| 45.0 | 0.205 | 0.218 | 0.013 |
| 55.0 | 0.259 | 0.279 | 0.019 |
| 65.0 | 0.318 | 0.356 | 0.038 |
| 75.0 | 0.401 | 0.457 | 0.056 |
| 85.0 | 0.502 | 0.604 | 0.102 |
| 95.0 | 3.289 | 4.054 | 0.764 |
| 98.0 | 4.006 | 4.006 | |

Example 6. Mass Spectrometric Analyses of Compound 1 Citrate Coordination Complex Form A. Evidence for the Conversion of Compound 1 Citrate Coordination Complex to ((2-ethylbutanoyl)oxy)methyl (R)-2-hydroxy-3-propionamido-3,4-dihydro-2H-benzo[e][1,2]oxaborinine-8-carboxylate (Compound 1) in Aqueous Solution.

Mass spectrometric (MS) analyses were performed to confirm the structure of Compound 1 citrate coordination complex Form A, and evaluate the ability of citric acid to dissociate from Compound 1 citrate coordination complex in water. Compound 1 citrate coordination complex Form A was diluted in acetonitrile water mixtures (2/1 v/v) and analyzed by mass spectrometry. The mass spectrum of Compound 1 citrate coordination complex Form A diluted in anhydrous acetonitrile showed major peaks consistent with Compound 1 citrate coordination complex; $(M-H)^-$ at nominal 564 Da and a sodium bound ion $[M+Na]^+$ at nominal 588 Da.

The mass spectrum of Compound 1 citrate coordination complex diluted in water showed major peaks at nominal with m z 390.1 for the $[M-H]^-$, and m z 392.2 for the $[M+H]^+$ peak, in agreement with the monoisotopic mass of the proposed molecular formula of $C_{19}H_{26}BNO_7$. The molecular mass of Compound 1 is 391.23 Da and the exact mass is 391.18 Da.

Example 7. Single Crystal X-Ray Structure Determination of Compound 1 Citrate Coordination Complex Form A.

A colorless plank having approximate dimensions of 0.29×0.09×0.03 $mm^3$, was mounted on a polymer loop in random orientation. Preliminary examination and data collection were performed on a Rigaku SuperNova diffractometer, equipped with a copper anode microfocus sealed X-ray tube (Cu Kα $\lambda$=1.54184 Å) and a Dectris Pilatus3 R 200K hybrid pixel array detector.

Cell constants and an orientation matrix for data collection were obtained from least-squares refinement using the setting angles of 26685 reflections in the range 3.7980°<θ<75.3640°. The space group was determined by the program CRYSALISPRO to be P1. The data were collected to a maximum diffraction angle (2θ) of 151.7360 at room temperature.

The structure was solved by direct methods using SHELXT. The remaining atoms were located in succeeding difference Fourier syntheses. The structure was refined using SHELXL-2014. Hydrogen atoms residing on nitrogen were refined independently. All other hydrogen atoms were included in the refinement but restrained to ride on the atom to which they are bonded. The structure was refined in full-matrix least-squares by minimizing the function:

$$\sum w(|F_o|^2 - |F_c|^2)^2$$

where the weight, w, is defined as $1/[\sigma^2(F_o^2)+(0.1475P)^2]$, where $P=(F_o^2+2F_c^2)/3$.

Scattering factors were taken from the "International Tables for Crystallography". Of the 21610 reflections used in the refinements, only the reflections with intensities larger than twice their uncertainty [I>2σ(I)], 17355, were used in calculating the fit residual, R. The final cycle of refinement included 1475 variable parameters, 18 restraints, and converged with respective unweighted and weighted agreement factors of:

$$R = \sum|F_o - F_c|/\sum F_o = 0.0627$$

$$R_w = \sqrt{\sum w(F_o^2 - F_c^2)^2/\sum w(F_o^2)^2} = 0.1829$$

Figure 11:
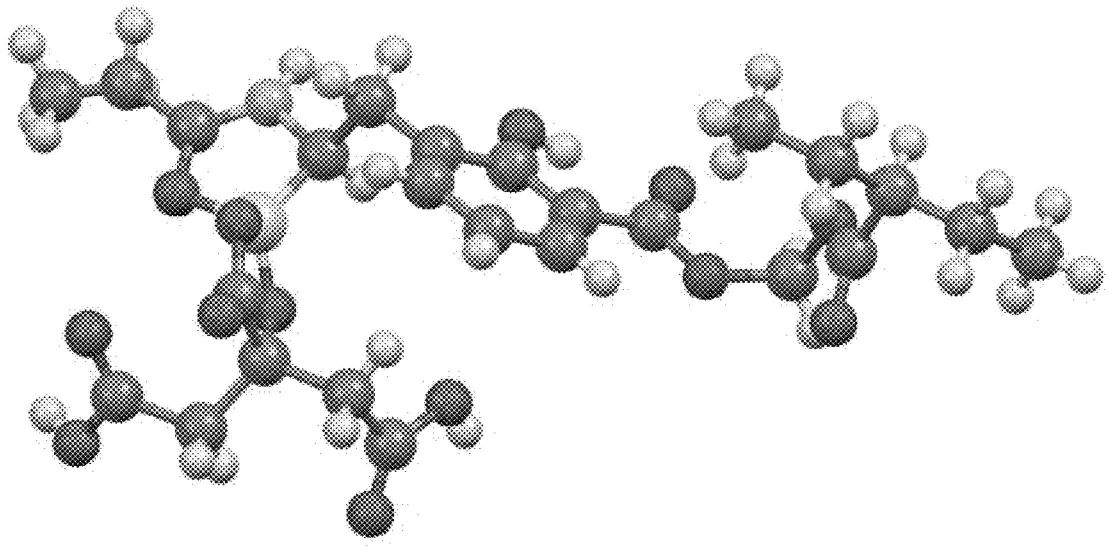
FIG. 11 shows the single crystal x-ray structure for Compound 1 citrate coordination complex Form A.

Table 6 outlines the parameters obtained from the refined structure. FIG. 11 shows a ball-and-stick rendering of the 3-dimensional structure derived from this X-ray crystallography experiment.

TABLE 6

Single Crystal X-ray Data and Collection Parameters, Compound 1 Citrate Coordination Complex, Form A

| | |
|---|---|
| Empirical formula | $C_{25}H_{32}BNO_{13}$ |
| Formula weight (g mol−1) | 565.32 |
| Temperature (K) | 299.6(4) |
| Wavelength (Å) | 1.54184 |
| Crystal system | triclinic |
| Space group | P1 |
| Unit cell parameters | |
| a = 8. 45420(10) Å | α = 89.585(2)° |
| b = 12.1729(2) Å | β = 82.3940(10)° |
| c = 30.0610(6) Å | γ = 71.3240(10)° |
| Unit cell volume ($Å^3$) | 2902.92(8) |
| Cell formula units, Z | 4 |
| Calculated density (g $cm^{-3}$) | 1.294 |
| Absorption coefficient ($mm^{-1}$) | 0.887 |
| F(000) | 1192 |
| Crystal size ($mm^3$) | 0.29 × 0.09 × 0.03 |
| Reflections used for cell measurement | 26685 |
| θ range for cell measurement | 3.7980°-75.3640° |
| Total reflections collected | 59262 |
| Index ranges | −10 ≤ h ≤ 10; −14 ≤ k ≤ 15; −37 ≤ l ≤ 37 |
| θ range for data collection | θmin = 3.836°, $\theta_{ma}$x = 75.868° |
| Completeness to $\theta_{max}$ | 97.6% |
| Completeness to $\theta_{full}$ = 67.684° | 99.8% |
| Absorption correction | multi-scan |
| Transmission coefficient range | 0.761-1.000 |
| Refinement method | full matrix least-squares on F2 |
| Independent reflections | 21610 [Rint = 0.0387, Rσ = 0.0380] |
| Reflections [ I > 2σ(I) ] | 17355 |
| Reflections/restraints/parameters | 21610/18/1475 |
| Goodness-of-fit on F2 | S = 1.04 |
| Final residuals [ I > 2σ(I) ] | R = 0.0627, Rw = 0.1829 |
| Final residuals [ all reflections ] | R = 0.0732, Rw = 0.1958 |
| Largest diff. peak and hole (e $Å^{-3}$) | 0.379, −0.299 |

TABLE 6-continued

Single Crystal X-ray Data and Collection Parameters, Compound 1 Citrate Coordination Complex, Form A

| | |
|---|---|
| Max/mean shift/standard uncertainty | 2.744/0.034 |
| Absolute structure determination | Flack parameter: 0.08(6)<br>Hooft parameter: 0.05(5)<br>Friedel coverage: 80.7% |

Example 8. Preparation of Compound 1 Citrate Coordination Complex Form B.

A unique crystalline material, designated Form B, was observed in initial experiments to produce Compound 1 citrate coordination complex. Compound 1-ethanolate and citric acid (1:1 molar ratio) were added into a 100 mL round-bottom flask with 15 mL of anhydrous ethyl acetate. The resultant solution was heated and maintained at 80° C. for 3.5 hours under an inert atmosphere. The resultant solution was evaporated to obtain a viscous oil which was further dried by purging with $N_2$ for ~15 hours. The material was then treated with diethyl ether and stirred for 1 hour. Heptane was then added to suspension and stirred for another 24 hours. The solid was filtered and dried at room temperature for ~2 hours.

Example 9. XRPD Characterization of Compound 1 Citrate Coordination Complex Form B.

The indexed XRPD pattern of Compound 1 citrate coordination complex, Form B is illustrated in FIG. 6 and indicates crystalline material with some amorphous content.

Example 10. Thermal Analysis of Compound 1 Citrate Coordination Complex Form B.

Figure 8:
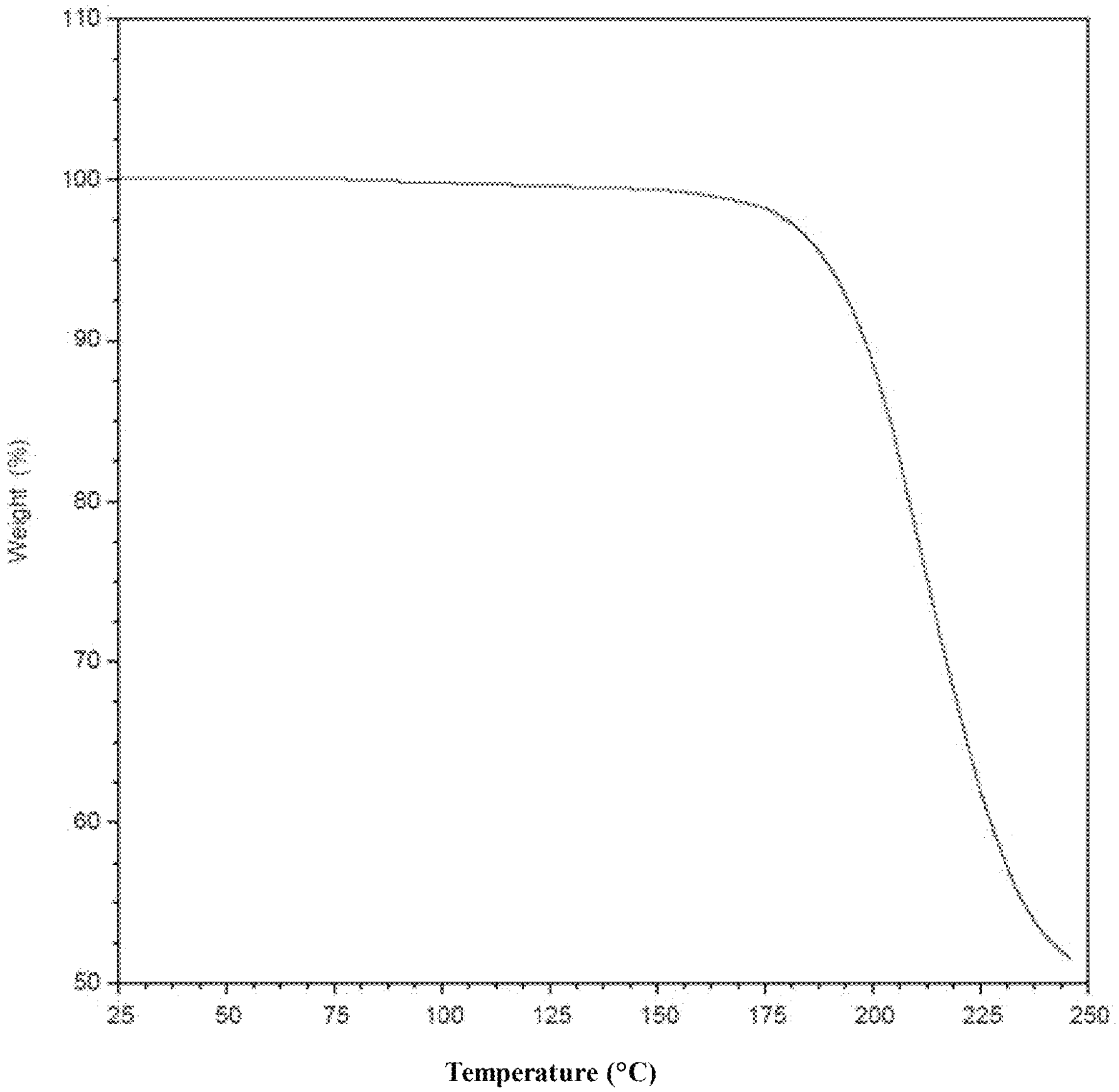
FIG. 8 shows the TGA of Compound 1 citrate coordination complex Form B.

Thermal analysis of Compound 1 citrate coordination complex Form B is presented in FIG. 7 and FIG. 8. The DSC thermogram of Compound 1 citrate coordination complex Form B (FIG. 7) exhibits a sharp peak, coincident with the onset of a single endotherm, at 142.10° C. (peak maximum). A weight loss of 0.7% is observed in the TGA (FIG. 8) between 24.8 and 120° C.

Example 11: Dynamic Vapor Sorption (DVS) Analysis of Compound 1 Citrate Coordination Complex Form B.

Figure 9:
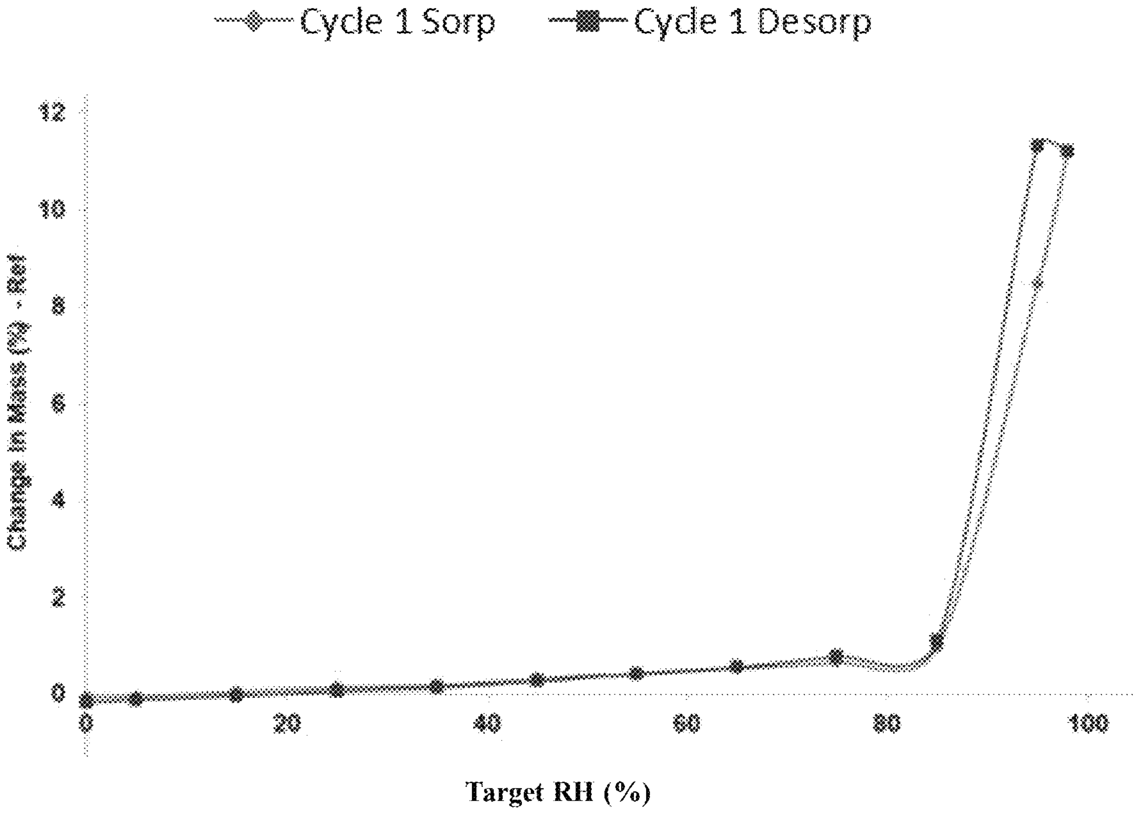
FIG. 9 shows the DVS analysis of Compound 1 citrate coordination complex Form B.

DVS analysis of Compound 1 citrate coordination complex Form B was conducted from 0% RH to 98% RH and back to 0% RH at 10% RH increments (FIG. 9). The DVS isotherm of Form B is qualitatively similar to that of Form A. Form B lost 0.1 wt % upon equilibration at ~0% RH. With increasing RH, the sample showed ~1.0 wt % gain between 0% RH and 85% RH. Above 85% RH the material increased in weight to 11.2% but returned to the initial weight with minimal hysteresis (Table 7). Following DVS analysis, it was noted that the XRPD of the sample matched that of the material before DVS analysis.

TABLE 7

Time course of water absorption for Compound 1 citrate coordination complex Form B under increasing relative humidity

| Target | Change In Mass (%)-ref | | |
|---|---|---|---|
| RH (%) | Sorption | Desorption | Hysteresis |
| 0.0 | −0.07 | −0.17 | |
| 5.0 | −0.05 | −0.13 | −0.07 |
| 15.0 | 0.04 | −0.05 | −0.08 |
| 25.0 | 0.13 | 0.06 | −0.07 |
| 35.0 | 0.17 | 0.13 | −0.04 |
| 45.0 | 0.31 | 0.25 | −0.06 |
| 55.0 | 0.41 | 0.43 | 0.02 |

TABLE 7-continued

| Time course of water absorption for Compound 1 citrate coordination complex Form B under increasing relative humidity | | | |
|---|---|---|---|
| Target | Change In Mass (%)-ref | | |
| RH (%) | Sorption | Desorption | Hysteresis |
| 65.0 | 0.53 | 0.56 | 0.03 |
| 75.0 | 0.66 | 0.79 | 0.12 |
| 85.0 | 0.98 | 1.11 | 0.13 |
| 95.0 | 8.47 | 11.32 | 2.85 |
| 98.0 | 11.18 | 11.18 | |

Example 12. Interconversion Slurries.

The difference in free energy between solid phases of the same composition (i.e. true polymorphs) is related to their relative solubilities, with the most stable polymorph having the lowest solubility in any solvent compared to a metastable polymorph. Therefore, a saturated solution with respect to the most stable form is undersaturated with respect to the less stable form. In the presence of seeds of different polymorphs, the less stable polymorph will therefore dissolve over time, resulting in further growth of the most stable form.

Competitive suspension equilibration experiments of the two polymorphs of the Compound 1 citrate coordination complex in dry isopropyl acetate and in dry TBME confirmed that Form A was thermodynamically more stable than Form B at 25° C. Approximately equal amounts of Form A, and Form B (containing a minor amount of Form A) were added to the filtered saturated solutions, and the suspensions were slurried at room temperature for ~2 weeks, and the isolated solids were observed by polarized light microscopy (PLM) and analyzed by XRPD. XRPD patterns of the solids isolated from both slurries were consistent with Form A. These data suggest Form A is the stable form at room temperature.

Example 13: Ceftibuten and Compound 1 Citrate Coordination Complex Blend Stability.

The physical stability of the ceftibuten dihydrate and Compound 1 citrate coordination complex, crystal Form A, were confirmed by X-Ray Powder Diffraction (XRPD) and Raman spectroscopy to evaluate and change in the crystal form of either drug substance when combined in a 1:1 (w/w) dry powder mixture.

The XRPD data shows that the physical blend of the two drug substances is a combination of ceftibuten dihydrate and Compound 1 citrate coordination complex with no additional peaks observed.

A 1:1 physical blend of ceftibuten dihydrate and Compound 1 citrate coordination complex was prepared and evaluated by XRPD. The resulting powder was stored in a sealed container at ambient temperature for three days and then the XRPD testing was repeated to evaluate any changes in the crystal form. An overlay of the XRPD data for the initial and Day 3 scan shows no change in the crystal forms.

The Raman spectroscopy performed on the 1:1 physical mixture of ceftibuten dihydrate and Compound 1 citrate coordination complex showed no changes from the initial scan after four days.

Analysis of the XRPD and Raman data shows a near perfect match of the two samples indicating that there were no changes in crystal form or exchange of water between the two drug substances.

Chemical stability of the binary blend was confirmed by monitoring HPLC purity (% peak area) of each drug substance and a binary blend that were put on stability at 25° C. and 40° C. Table 8 summarizes the data collected through 12 weeks and shows no degradation of Compound 1 citrate coordination complex at all conditions, and temperature dependent degradation of ceftibuten dihydrate that is comparable to the ceftibuten dihydrate control at the same temperature.

TABLE 8

| Stability Summary for Ceftibuten Dihydrate and Compound 1 Citrate Coordination Complex Controls and Blend | | | | |
|---|---|---|---|---|
| | 40° C. Storage | | | |
| | | Blend | | |
| Time (Weeks) | Compound 1 citrate | Compound 1 citrate | Ceftibuten dihydrate | Ceftibuten dihydrate |
| 0 | 100.0% | 100.0% | 97.5% | 98.6% |
| 5 | 100.0% | 100.0% | 98.2% | 98.4% |
| 8 | 100.0% | 100.0% | 94.8% | 96.7% |
| 12 | 100.0% | 100.0% | 93.7% | 92.8% |
| | 25° C. Storage | | | |
| | | Blend | | |
| Time (Weeks) | Compound 1 citrate | Compound 1 citrate | Ceftibuten dihydrate | Ceftibuten dihydrate |
| 0 | 100.0% | 100.0% | 98.4% | 98.6% |
| 5 | 100.0% | 100.0% | 98.6% | 98.6% |
| 8 | 100.0% | 100.0% | 98.3% | 98.6% |
| 12 | 100.0% | 100.0% | 96.8% | 98.4% |

Example 14: Excipient Compatibility with Ceftibuten Dihydrate and Compound 1 Citrate Coordination Complex Blends The compatibility of the drug substances with select functional excipients was confirmed by comparing the assay and purity of samples stored at 50° C. for 5 weeks to the drug substance control samples. The excipients tested included: microcrystalline cellulose (binder); magnesium stearate (lubricant); sodium starch glycolate (disintegrant); and colloidal silica (glidant). The blend samples were prepared by first combining the two drug substances in a 1:1 weight ratio which was then blended with an equal weight of each excipient to yield a final ratio of 1:1:2 of ceftibuten dihydrate/Compound 1 citrate coordination complex/excipient. The samples were transferred to a 3-dram glass vial with a tight-fitting cap and placed in a 50° C. oven. A summary of the compatibility data is provided in Table 9.

TABLE 9

| Summary of 50° C. Excipient Compatibility HPLC Peak Purity Data | | | | |
|---|---|---|---|---|
| | | Time | HPLC Purity (Peak Area %) | |
| Sample | Function | (Weeks) | Compound 1 | Ceftibuten |
| Ceftibuten dihydrate | Control | 2 | — | 99.2% |
| | | 5 | — | 94.8% |
| Compound 1 Citrate coordination complex | Control | 2 | 100.0% | — |
| | | 5 | 100.0% | — |
| Microcrystalline Cellulose Blend | Filler/Binder | 2 | 100.0% | 98.8% |
| | | 5 | 100.0% | 97.8% |
| Magnesium Stearate Blend | Lubricant | 2 | 100.0% | 97.9% |
| | | 5 | 100.0% | 96.5% |
| Colloidal Silica Blend | Glidant | 2 | 100.0% | 96.4% |
| | | 5 | 100.0% | 95.3% |

TABLE 9-continued

| Summary of 50° C. Excipient Compatibility HPLC Peak Purity Data | | | | |
|---|---|---|---|---|
| | | Time | HPLC Purity (Peak Area %) | |
| Sample | Function | (Weeks) | Compound 1 | Ceftibuten |
| Sodium Starch Glycolate Blend | Disintegrant | 2 | 100.0% | 97.8% |
| | | 5 | 100.0% | 98.2% |

The accelerated data showed that the chemical stability for ceftibuten and Compound 1 citrate coordination complex in the presence of the excipients was comparable to the stability for the drug substance controls confirming the compatibility of the excipients with each drug substance.

Example 15a: Preparation of Fixed Dose Combination (FDC) Capsule Formulations of Ceftibuten Dihydrate-Compound 1 Citrate Coordination Complex.

General Description of Capsule Manufacturing Process

The process to manufacture solid oral dosage forms of ceftibuten dihydrate/Compound 1 citrate coordination complex allows for formulations containing ceftibuten dihydrate and Compound 1 citrate coordination complex at any ratio, along with the addition of common excipients to facilitate processing (fillers, binders, lubricants, glidants etc.) or excipients to adjust the pharmaceutical properties of the capsule (disintegrants).

The manufacturing process involves combining the two drug substances and desired excipients and blending the mixture to produce a homogeneous powder. The resulting blend was then densified using roller compaction to produce ribbons, which were broken down into granules by milling through a screen. The roller compaction process was repeated on the granules to further densify the granules and to ensure uniformity of the blend. The final granules were then encapsulated into the appropriate size capsules and sealed using an automated capsule banding machine. The physical and chemical stability of the capsules were evaluated using standard analytical and pharmaceutical techniques.

Preparation of 200 mg Compound 1/200 mg Ceftibuten Capsules

Fixed dose capsules that contained the equivalent to 200 mg ceftibuten (as ceftibuten dihydrate) and the equivalent to 200 mg of Compound 1 (as Compound 1 citrate coordination complex) were prepared from the formulation composition shown in Table 10.

TABLE 10

Formulation of 200 mg Compound 1 and 200 mg Ceftibuten FDC Capsules

| Ingredients | Function | % w/w | Weight/Capsule (mg) |
|---|---|---|---|
| Ceftibuten Dihydrate[a] | Drug Substance | 39.58 | 229.4 |
| Compound 1 Citrate coordination complex[b] Form A | Drug Substance | 50.11 | 290.4 |
| Microcrystalline Cellulose | Diluent | 8.73 | 50.6 |
| Magnesium Stearate | Lubricant | 0.40 | 2.3 |
| Colloidal Silica | Glidant | 0.40 | 2.3 |
| Sodium Starch Glycolate | Disintegrant | 0.79 | 4.6 |
| Total | | 100.00 | 579.6 |

[a]Equivalent to 200.0 mg of ceftibuten per capsule
[b]Equivalent to 200.0 mg of Compound 1 per capsule (correction factor x0.6922)

Each of the ingredients were weighed out, screened to eliminate any lumps, and transferred to a glass jar. The resulting mixture was blended until uniform using a Turbula® mixer and the homogeneous powder blend was transferred to the feed hopper and compressed into ribbons using a Freund Vector TFC-Lab roller compactor. The ribbons were milled through a stainless-steel screen to yield a coarse powder, which was further densified by a second pass through the roller compactor followed by screening to yield the final granules. The granules were encapsulated into Size 00, gelatin capsules using a manual 100-unit capsule tray filler with a target fill weight of 579.6 mg. The capsules were then band-sealed using a Schaeffer Technologies lab scale banding machine.

Preparation of 50 mg Compound 1/200 mg Ceftibuten Capsules

Fixed dose capsules that contained the equivalent to 200 mg ceftibuten (as ceftibuten dihydrate) and the equivalent to 50 mg Compound 1 (as Compound 1 citrate coordination complex) were prepared from the formulation composition shown in Table 11.

TABLE 11

Formulation of 50 mg Compound 1 and 200 mg Ceftibuten FDC Capsules

| Ingredients | Function | % w/w | Weight/Capsule (mg) |
|---|---|---|---|
| Ceftibuten Dihydrate[a] | Drug Substance | 68.36 | 229.4 |
| Compound 1 Citrate coordination complex[b] Form A | Drug Substance | 21.64 | 72.6 |
| Microcrystalline Cellulose | Diluent | 8.00 | 26.9 |
| Magnesium Stearate | Lubricant | 0.50 | 1.7 |
| Colloidal Silica | Glidant | 0.50 | 1.7 |
| Sodium Starch Glycolate | Disintegrant | 1.00 | 3.4 |
| Total | | 100.00 | 335.7 |

[a]Equivalent to 200.0 mg of ceftibuten per capsule
[b]Equivalent to 50.0 mg of Compound 1 per capsule (correction factor x0.6922)

The appropriate amount of each of the components of the formulation were screened to eliminate any lumps and transferred to a glass jar. The resulting mixture was blended until uniform using a Turbula® mixer. The powder blend was transferred to the feed hopper and compressed into ribbons using a Freund Vector TFC-Lab Micro roller compactor. The ribbons were screened to yield granules, which were further densified by a second pass through the roller compactor followed by screening to yield the final granules. The granules were encapsulated into Size 0, gelatin capsules with a target fill weight of 335.7 mg using a manual 100-unit capsule tray filler. The capsules were then band-sealed using a Schaeffer Technologies lab scale banding machine.

Example 15b: Preparation of Fixed Dose Combination (FDC) Capsule Formulation of Ceftibuten Dihydrate-Compound 1 Ethanolate.

Preparation of 200 mg Compound 1/200 mg Ceftibuten Capsules

Fixed dose capsules that contained the equivalent to 200 mg ceftibuten (as ceftibuten dihydrate) and the equivalent to 200 mg of Compound 1 (as Compound 1 ethanolate) were prepared from the formulation composition shown in Table 12.

TABLE 12

| Formulation of 200 mg Compound 1 and 200 mg Ceftibuten FDC Capsules | | | |
|---|---|---|---|
| Ingredients | Function | % w/w | Weight/Capsule (mg) |
| Ceftibuten Dihydrate[a] | Drug Substance | 45.16 | 229.4 |
| Compound 1 Ethanolate[b] | Drug Substance | 43.07 | 218.80 |
| Microcrystalline Cellulose | Diluent | 9.96 | 50.57 |
| Magnesium Stearate | Lubricant | 0.45 | 2.3 |
| Colloidal Silica | Glidant | 0.45 | 2.3 |
| Sodium Starch Glycolate | Disintegrant | 0.91 | 4.6 |
| Total | | 100.00 | 507.97 |

[a]Equivalent to 200.0 mg of ceftibuten per capsule

[b]Equivalent to 200.0 mg of Compound 1 per capsule (correction factor x0.9141)

Each of the ingredients were weighed out, screened to eliminate any lumps, and transferred to a glass jar. The resulting mixture was blended until uniform, and the homogeneous powder blend was compacted using a manual trituration process. The resulting compact was milled through a stainless-steel screen to yield a coarse powder, which was further densified by a second manual compaction step followed by screening to yield the final granules. The granules were encapsulated into Size 00, gelatin capsules by hand filling with a target fill weight of 507.97 mg.

Example 16: Polymorphic Stability of Compound 1 Citrate Coordination Complex and Ceftibuten Dihydrate in the FDC Capsule The physical (crystal form) stability of the co-encapsulated ceftibuten and Compound 1 citrate coordination complex capsule was confirmed using X-Ray Powder Diffraction (XRPD). The first experiment evaluated the effects of roller compaction by comparing the XRPD data collected on the granules to the historical data for the physical blend of the two drug substances.

The XRPD comparison of the physical blend of Ceftibuten dihydrate/Compound 1 citrate coordination complex and the drug product granules showed no change in the crystal form of either drug substance during the roller compaction and encapsulation process. The second experiment evaluated the stability of the ceftibuten dihydrate and Compound 1 citrate coordination complex crystal forms by measuring the XRPD and Raman spectroscopy on the FDC capsules that were stored at 2-8° C. and 25° C. for ~8 months.

The FDC capsule showed comparable diffractograms between the capsules stored at 2-8° C. and the capsules stored at 25° C. The XRPD data for the stability samples were comparable to the initial blend data confirming no changes in the crystal form on stability.

The FDC capsule showed comparable Raman spectra between the capsules stored at 2-8° C. and the capsules stored at 25° C. The XRPD data for the stability samples were comparable to the initial blend data confirming no changes in the crystal form over the eight months while stored at 2-8° C. or 25° C.

Example 17: Chemical Stability of Compound 1 Citrate Coordination Complex and Ceftibuten Dihydrate in the FDC Capsule The chemical stability of the ceftibuten dihydrate and Compound 1 citrate coordination complex capsules were evaluated by measuring assay and purity of each drug substance for capsules that were put on stability at 25° C. and 40° C. The capsules were analyzed at each time point for appearance, % label claim, related substances, and dissolution. The 40° C. and 25° C. data are summarized in Table 13 and Table 14, respectively.

TABLE 13

Summary of 40° C. Stability Data for 200 mg/200 mg FDC capsules of Ceftibuten dihydrate-Compound 1 Citrate Coordination Complex

| Attribute (Test Method) | Specification | | Testing Interval T = 0 | 1 Month | 2 Months | 3 Months | 4 Months | 6 Months |
|---|---|---|---|---|---|---|---|---|
| Capsule Appearance | * | | * | * | * | * | * | * |
| Appearance of Capsule Contents | Light yellow to tan powder | | Light yellow powder | Light yellow powder | Light yellow powder | Light yellow powder | Light yellow powder | Light yellow powder |
| Compound 1 | % Label Claim | 90.0-110.0% | 93.4% | 96.8% | 97.5% | 100.6% | 102.4% | ≥96.1% |
| | Degradation Products by HPLC | Any single un-specified ≥0.05% | | | | | | |
| | Compound 2 | ≤0.20% area | None Detected | None Detected | None Detected | None Detected | None Detected | None Detected |
| | Total Degradation Products | ≤1.0% | 0.0% | 0.0% | 0.0% | 0.0% | 0.0% | 0.0% |

| | Dissolution | Q = 80%, 30 min | Min | % | Min | % | Min | % | Min | % | Min | % | Min | % |
|---|---|---|---|---|---|---|---|---|---|---|---|---|---|---|
| | | | 15 | 92 | 15 | 100 | 15 | 98 | 15 | 97 | 15 | 98 | 15 | 97 |
| | | | 30 | 96 | 30 | 100 | 30 | 99 | 30 | 98 | 30 | 99 | 30 | 98 |
| | | | 45 | 94 | 45 | 101 | 45 | 100 | 45 | 99 | 45 | 99 | 45 | 99 |
| | | | 60 | 99 | 60 | 101 | 60 | 100 | 60 | 99 | 60 | 100 | 60 | 99 |

TABLE 13-continued

Summary of 40° C. Stability Data for 200 mg/200 mg FDC capsules of Ceftibuten dihydrate-Compound 1 Citrate Coordination Complex

| Attribute (Test Method) | Specification | | Testing Interval T = 0 | | 1 Month | | 2 Months | | 3 Months | | 4 Months | | 6 Months | |
|---|---|---|---|---|---|---|---|---|---|---|---|---|---|---|
| Ceftibuten | % Label Claim | 90.0-110.0% | 92.2% | | 93.5% | | 96.9% | | ≥98.9% | | 106.0% | | ≥83.6% | |
| | Degradation Products by HPLC | Any single un-specified ≥0.05% | | | | | | | | | | | | |
| | Impurity 14 (Decarboxyl) | TBD | 0.21% | | 0.48% | | 0.63% | | 1.62% | | 2.35% | | 11.72% | |
| | Total Degradation Products | Report Results | 0.2% | | 0.5% | | 0.6% | | 1.6% | | 2.4% | | 11.7% | |
| | Dissolution | Q = 80%, 60 min | Min | % | Min | % | Min | % | Min | % | Min | % | Min | % |
| | | | 15 | 96 | 15 | 100 | 15 | 100 | 15 | 99 | 15 | 99 | 15 | 100 |
| | | | 30 | 96 | 30 | 100 | 30 | 100 | 30 | 99 | 30 | 100 | 30 | 100 |
| | | | 45 | 98 | 45 | 99 | 45 | 100 | 45 | 100 | 45 | 100 | 45 | 100 |
| | | | 60 | 100 | 60 | 100 | 60 | 100 | 60 | 100 | 60 | 100 | 60 | 100 |

Capsule Appearance: *: White opaque hard capsule with no holes, cuts, cracks or dents

TABLE 14

Summary of 25° C. Stability Data for 200 mg/200 mg FDC capsules of Ceftibuten dihydrate-Compound 1 Citrate Coordination Complex

| Attribute (Test Method) | Specification | | Testing Interval T= 0 | | 1 Month | | 2 Months | | 3 Months | | 4 Months | | 6 Months | | 9 Months | |
|---|---|---|---|---|---|---|---|---|---|---|---|---|---|---|---|---|
| Capsule Appearance | * | | * | | * | | * | | * | | * | | * | | * | |
| Appearance of Capsule Contents | Light yellow to tan powder | | Light yellow powder | | Light yellow powder | | Light yellow powder | | Light yellow powder | | Light yellow powder | | Light yellow powder | | Light yellow powder | |
| Compound 1 | % Label Claim | 90.0-110.0% | 93.4% | | 108.7% | | 97.5% | | 102.2% | | 101.1% | | 97.0% | | 98.9% | |
| | Degradation Products by HPLC | Any single un-specified ≥0.05% | | | | | | | | | | | | | | |
| | Compound 2 | ≤0.20% area | None Detected | | None Detected | | None Detected | | None Detected | | None Detected | | None Detected | | None Detected | |
| | Total Degradation Products | ≤1.0% | 0.0% | | 0.0% | | 0.0% | | 0.0% | | 0.0% | | 0.0% | | 0.0% | |
| | Dissolution | Q = 80%, 30 min | Min | % | Min | % | Min | % | Min | % | Min | % | Min | % | Min | % |
| | | | 15 | 92 | 15 | 98 | 15 | 98 | 15 | 98 | 15 | 98 | 15 | 103 | 15 | 97 |
| | | | 30 | 96 | 30 | 99 | 30 | 99 | 30 | 99 | 30 | 99 | 30 | 98 | 30 | 99 |
| | | | 45 | 94 | 45 | 99 | 45 | 100 | 45 | 99 | 45 | 100 | 45 | 99 | 45 | 100 |
| | | | 60 | 99 | 60 | 99 | 60 | 100 | 60 | 100 | 60 | 100 | 60 | 101 | 60 | 99 |
| Ceftibuten | % Label Claim | 90.0-110.0% | 92.2% | | 101.6% | | 100.8% | | 102.9% | | 107.2% | | 100.8% | | 101.7% | |
| | Degradation Products by HPLC | Any single un-specified ≥0.05% | | | | | | | | | | | | | | |
| | Impurity 14 (Decarboxyl) | TBD | 0.21% | | 0.37% | | 0.16% | | 0.27% | | 0.28% | | 0.39% | | 0.32% | |

TABLE 14-continued

Summary of 25° C. Stability Data for 200 mg/200 mg FDC capsules of Ceftibuten dihydrate-Compound 1 Citrate Coordination Complex

| Attribute (Test Method) | | Specification | Testing Interval T= 0 | | 1 Month | | 2 Months | | 3 Months | | 4 Months | | 6 Months | | 9 Months | |
|---|---|---|---|---|---|---|---|---|---|---|---|---|---|---|---|---|
| | Total Degradation Products | Report Results | 0.2% | | 0.4% | | 0.2% | | 0.3% | | 0.3% | | 0.4% | | 0.3% | |
| | Dissolution | Q = 80%, 60 min | Min | % | Min | % | Min | % | Min | % | Min | % | Min | % | Min | % |
| | | | 15 | 96 | 15 | 102 | 15 | 99 | 15 | 99 | 15 | 99 | 15 | 100 | 15 | 99 |
| | | | 30 | 96 | 30 | 102 | 30 | 99 | 30 | 100 | 30 | 100 | 30 | 100 | 30 | 100 |
| | | | 45 | 98 | 45 | 102 | 45 | 100 | 45 | 100 | 45 | 100 | 45 | 100 | 45 | 100 |
| | | | 60 | 100 | 60 | 101 | 60 | 100 | 60 | 100 | 60 | 100 | 60 | 100 | 60 | 99 |

Capsule Appearance: *: White opaque hard capsule with no holes, cuts, cracks or dents Example 18: In Vitro and In Vivo Comparison of Compound 1 Citrate Coordination Complex/Ceftibuten Dihydrate FDC Capsules with Co-Dosed Compound 1 Ethanolate Capsules and Ceftibuten Capsules.

Self-Emulsifying Drug Delivery System (SEDDS) Capsules of Compound 1 Ethanolate

The 200 mg SEDDS capsules were prepared from a 400 mg/mL Compound 1 solution. A 20 mL batch of 400 mg/mL Compound 1 SEDDS formulation was prepared by combining 8.71 g of Compound 1 ethanolate complex and 12.3 g of the vehicle stock (20/20/60 v % of Propylene glycol/PEG-400/Tocophersolan) into a 100 mL round bottom flask outfitted with a magnetic stir bar and mixing at ~60° C. on a hot plate until a clear, homogeneous solution was obtained. The resulting solution was filled, by volume (0.500 mL) into a Size 1 white opaque capsule using a positive displacement pipette. The resulting capsules were stored at 2-8° C. prior to use.

In Vitro Study

Figure 12:
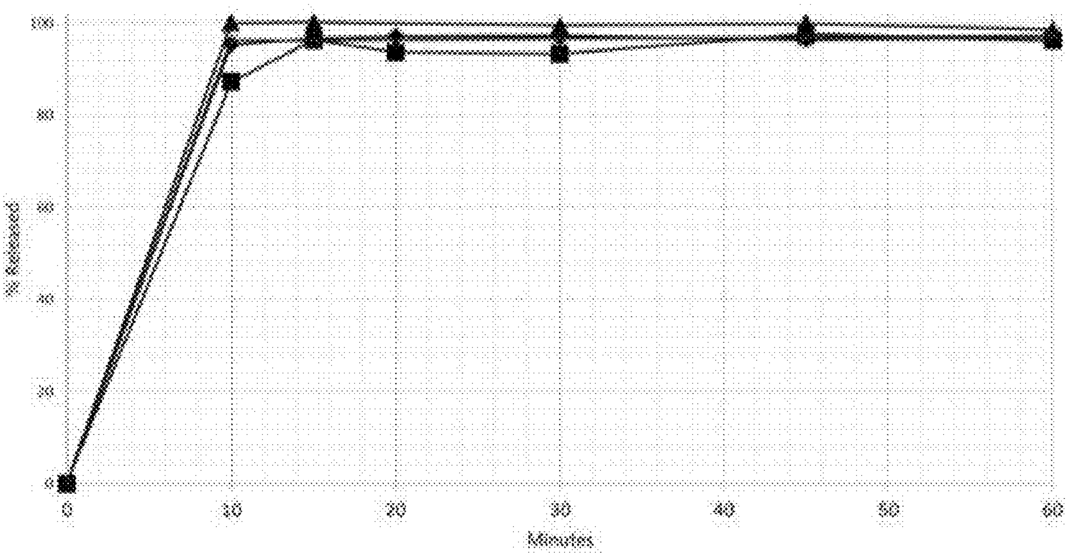
FIG. 12 shows the dissolution profile comparison of the fixed dose capsule prototype of ceftibuten dihydrate combined with compound 1 citrate coordination complex and co-dosed capsules of ceftibuten dihydrate and the SEDDS formulation of Compound 1 ethanolate complex.

Dissolution testing (Apparatus II method) performed using 900 mL of pH 6.8 50 mM sodium bicarbonate buffer solution and a 75 RPM paddle speed on the FDC capsule prototypes described above showed comparable release of ceftibuten and Compound 1 citrate coordination complex to the "co-dosed" (separate capsules) formulations of Compound 1 ethanolate and ceftibuten as shown in FIG. 12. Although the SEDDS based capsule formulation of Compound 1 ethanolate exhibited immediate release of Compound 1, the formulation was not stable when placed on stability at standard ICH stability conditions of 25° C./60% R.H. and 40° C./65% R.H. Table 15 shows the HPLC purity (Peak Area %) for the Compound 1 Ethanolate and Compound 1 Citrate coordination complex capsule formulations.

TABLE 15

Stability Summary of Formulations for Compound 1 Ethanolate SEDDS Capsules and Compound 1 Citrate Coordination Complex FDC Capsules

| | % HPLC Purity of Compound 1 Parent | | | |
|---|---|---|---|---|
| | Ethanolate SEDDS Capsules | | Citrate FDC Capsules | |
| Time (M) | 25° C. | 40° C. | 25° C. | 40° C. |
| 0 | 98.9% | 98.9% | 100.0% | 100.0% |
| 1 | 99.1% | 92.7% | 100.0% | 100.0% |

TABLE 15-continued

Stability Summary of Formulations for Compound 1 Ethanolate SEDDS Capsules and Compound 1 Citrate Coordination Complex FDC Capsules

| | % HPLC Purity of Compound 1 Parent | | | |
|---|---|---|---|---|
| | Ethanolate SEDDS Capsules | | Citrate FDC Capsules | |
| Time (M) | 25° C. | 40° C. | 25° C. | 40° C. |
| 2 | 97.2% | 88.8% | 100.0% | 100.0% |
| 3 | 93.2% | 85.1% | 100.0% | 100.0% |
| 4 | 90.9% | 82.8% | 100.0% | 100.0% |
| 5 | 89.1% | 76.1% | 100.0% | 100.0% |
| 6 | 87.4% | 74.4% | 100.0% | 100.0% |

In Vivo Study

A single dose comparative PK study with the FDC and the single component formulations was conducted in cynomolgus monkeys. The study was performed by administering either a single FDC capsule (200 mg ceftibuten/200 mg Compound 1 citrate coordination complex) or two capsules (200 mg ceftibuten and 200 mg Compound 1 ethanolate SEDDS formulation). Each formulation was dosed in six monkeys (n=3/sex) with a seven-day wash-out period between the cohorts. Ceftibuten has been reported to have low bioavailability (~20%) in monkeys so ceftibuten PK was not evaluated in this study. Standard pharmacokinetic parameters for Compound 2 were calculated for both formulations and the average values are reported in Table 16. In addition, the oral bioavailability of Compound 2 from each formulation was estimated based on an existing intravenous PK study in cynomolgus monkeys with Compound 2 (also presented in Table 16). The two formulations showed comparable plasma levels of Compound 2 and Compound 1 but the oral bioavailability of Compound 2 was higher from the formulation containing Compound 1 citrate coordination complex.

TABLE 16

Formulation Comparison Pharmacokinetic Parameters in non-Human Primates

| Parameter | Co-Dosed Capsules (Compound 1 ethanolate SEDDS Capsules and Ceftibuten Capsules) | | | Fixed Dose Combination Capsule (200 mg Ceftibuten/200 mg Compound 1 Citrate) | | |
|---|---|---|---|---|---|---|
| | Male (n = 3) | Female (n = 3) | Average (n = 6) | Male (n = 3) | Female (n = 3) | Average (n = 6) |
| $AUC_{last}$ (hr * ng/mL)[a] | 115491 ± 66177 | 184236 ± 22397 | 149780 ± 58117 | 192666 ± 64826 | 255975 ± 80087 | 224321 ± 73817 |
| $AUC_{last}$/Dose[b] ([ng * hr/mL]/[mg/kg]) | 3602 ± 1908 | 3242 ± 397 | 3423 ± 1248 | 6216 ± 1657 | 4567 ± 1258 | 5292 ± 1596 |
| $C_{max}$ (ng/mL) | 28567 ± 7343 | 40800 ± 10413 | 34683 ± 10480 | 21870 ± 11437 | 43000 ± 23409 | 32435 ± 20136 |
| $C_{max}$/Dose[b] ([ng/mL]/[mg/kg]) | 811 ± 215 | 718 ± 181 | 811 ± 215 | 714 ± 386 | 761 ± 383 | 737 ± 345 |
| $T_{max}$ (hr)[c] | 2 (0.5-2) | 1 (1-4) | 1.5 (0.5-4) | 4 | 4 | 4 |
| Estimated F % (%)[d] | 42.3 ± 22.4 | 38.1 ± 4.67 | 40.2 ± 14.7 | 73.1 ± 19.5 | 53.7 ± 14.8 | 63.4 ± 18.8 |

NOTE:

The study administered a fixed dose and was not adjusted to account for the animal's weight, resulting in higher group mean PK parameter values for females. There were no gender-related differences in exposure.

[a]Total area under the plasma concentration-time curve, calculated to the last observable time point,

[b]$AUC_{last}$ and $C_{max}$ normalized to each animal's weight-adjusted dose of Compound 1 in mg/kg

[c]Median (min-max). Where no min-max range given in parentheses, $T_{max}$ occurred at the same time in all animals dEstimated oral bioavailability (F %) was calculated using each animal's Compound 2 dose-normalized $AUC_{last}$ (calculated by dividing each animal's $AUC_{last}$/dose by a correction factor ($MW_{Compound\ 2}/MW_{Compound\ 1}$), and dividing the Compound 2 dose-normalized $AUC_{last}$ by the mean $AUC_{last}$ value resulting from IV administration of 1 mg/kg of Compound 2 to cynomolgus monkeys (data generated in a previous study).

The FDC capsule made from the Compound 1 citrate coordination complex results in better overall in vivo exposure and oral bioavailability for Compound 2 compared to the SEDDS based capsules made from the Compound 1 ethanolate. The average AUC value is ~50% higher and the $T_{max}$ is less variable than the SEDDS capsule, resulting in an ~60% increase in estimated oral bioavailability of Compound 2.

Stability Studies

Stability studies were conducted on an FDC capsule containing 200 mg of Compound 1 citrate coordination complex and 200 mg of Ceftibuten. Samples were stored at 40° C., 25° C., and 2-8° C. to assess stability over time. After 6 months at 40° C., a significant increase in ceftibuten-related impurity 14 was observed, reaching 11.72% (see Table 17a and 17b). At 25° C., impurity 14 grew to 0.68% over 24 months (see Table 18a and 18b). Notably, the capsules stored at 2-8° C. remained stable, with no impurity growth detected (see Table 19a and 19b for the summary of the 2-8° C. stability data).

TABLE 17a

Summary of 40° C. Stability Data for 200 mg/200 mg FDC capsules of Ceftibuten-Compound 1 Citrate Coordination Complex (T = 0 to 2 months)

| Attribute (Test Method) | Specification | | Testing Interval T = 0 | 1 Month | 2 Months |
|---|---|---|---|---|---|
| Capsule Appearance | White opaque hard capsule with no holes, cuts, cracks or dents | | White opaque hard capsule with no holes, cuts, cracks or dents | White opaque hard capsule with no holes, cuts, cracks or dents | White opaque hard capsule with no holes, cuts, cracks or dents |
| Appearance of Capsule Contents | Light yellow to tan powder | | Light yellow powder | Light yellow powder | Light yellow powder |
| Compound 1 | % Label Claim | 90.0-110.0% | 93.4% | 96.8% | 97.5% |
| | Degradation Products by HPLC | Any single unspecified ≥0.05% | | | |
| | Compound 2 | ≤0.20% area | None Detected | None Detected | None Detected |
| | Total Degradation Products | ≤1.0% | 0.0% | 0.0% | 0.0% |
| | Dissolution | Q = 80%, 30 min | Min % <br> 15 92 <br> 30 96 <br> 45 94 <br> 60 99 | Min % <br> 15 100 <br> 30 100 <br> 45 101 <br> 60 101 | Min % <br> 15 98 <br> 30 99 <br> 45 100 <br> 60 100 |
| Ceftibuten | % Label Claim | 90.0-110.0% | 92.2% | 93.5% | 96.9% |
| | Degradation Products by HPLC | Any single unspecified ≥0.05% | | | |
| | Impurity 14 (Decarboxyl) | TBD | 0.21% | 0.48% | 0.63% |

TABLE 17a-continued

Summary of 40° C. Stability Data for 200 mg/200 mg FDC capsules of Ceftibuten-Compound 1 Citrate Coordination Complex (T = 0 to 2 months)

| Attribute (Test Method) | | Specification | Testing Interval T = 0 | | 1 Month | | 2 Months | |
|---|---|---|---|---|---|---|---|---|
| | Total Degradation Products | Report Results | 0.2% | | 0.5% | | 0.6% | |
| | Dissolution (Normalized) | Q = 80%, 60 min | Min | % | Min | % | Min | % |
| | | | 15 | 96 | 15 | 100 | 15 | 100 |
| | | | 30 | 96 | 30 | 100 | 30 | 100 |
| | | | 45 | 98 | 45 | 99 | 45 | 100 |
| | | | 60 | 100 | 60 | 100 | 60 | 100 |

TABLE 17b

Summary of 40° C. Stability Data for 200 mg/200 mg FDC capsules of Ceftibuten-Compound 1 Citrate Coordination Complex (T = 3 months to 6 months)

| Attribute (Test Method) | Specification | | | Testing Interval 3 Months | | 4 Months | | 6 Months | |
|---|---|---|---|---|---|---|---|---|---|
| Capsule Appearance | White opaque hard capsule with no holes, cuts, cracks or dents | | | White opaque hard capsule with no holes, cuts, cracks or dents | | White opaque hard capsule with no holes, cuts, cracks or dents | | White opaque hard capsule with no holes, cuts, cracks or dents | |
| Appearance of Capsule Contents | Light yellow to tan powder | | | Light yellow powder | | Light yellow powder | | Light yellow powder | |
| Compound 1 | % Label Claim | 90.0-110.0% | | 100.6% | | 102.4% | | 96.1% | |
| | Degradation Products by HPLC | Any single unspecified ≥0.05% | | | | | | | |
| | Compound 2 | ≤0.20% area | | None Detected | | None Detected | | None Detected | |
| | Total Degradation Products | ≤1.0% | | 0.0% | | 0.0% | | 0.0% | |
| | Dissolution | Q = 80%, 30 min | | Min | % | Min | % | Min | % |
| | | | | 15 | 97 | 15 | 98 | 15 | 97 |
| | | | | 30 | 98 | 30 | 99 | 30 | 98 |
| | | | | 45 | 99 | 45 | 99 | 45 | 99 |
| | | | | 60 | 99 | 60 | 100 | 60 | 99 |
| Ceftibuten | % Label Claim | 90.0-110.0% | | 98.9% | | 106.0% | | 83.6% | |
| | Degradation Products by HPLC | Any single unspecified ≥0.05% | | | | | | | |
| | Impurity 14 (Decarboxy1) | TBD | | 1.62% | | 2.35% | | 11.72% | |
| | Total Degradation Products | Report Results | | 1.6% | | 2.4% | | 11.7% | |
| | Dissolution (Normalized) | Q = 80%, 60 min | | Min | % | Min | % | Min | % |
| | | | | 15 | 99 | 15 | 99 | 15 | 100 |
| | | | | 30 | 99 | 30 | 100 | 30 | 100 |
| | | | | 45 | 100 | 45 | 100 | 45 | 100 |
| | | | | 60 | 100 | 60 | 100 | 60 | 100 |

TABLE 18a

Summary of 25° C. Stability Data for 200 mg/200 mg FDC capsules of Ceftibuten-Compound 1 Citrate Coordination Complex (T = 0 to 4 months)

| Attribute (Test Method) | Specification | Testing Interval T = 0 | 1 Month | 2 Month | 3 Month | 4 Month |
|---|---|---|---|---|---|---|
| Capsule Appearance | White opaque hard capsule with no holes, cuts, cracks, or dents | White opaque hard capsule with no holes, | White opaque hard capsule with no holes, | White opaque hard capsule with no holes, | White opaque hard capsule with no holes, | White c opaque hard apsule with no holes, |

TABLE 18a-continued

Summary of 25° C. Stability Data for 200 mg/200 mg FDC capsules of Ceftibuten-Compound 1 Citrate Coordination Complex (T = 0 to 4 months)

| Attribute (Test Method) | Specification | | Testing Interval T = 0 | 1 Month | 2 Month | 3 Month | 4 Month |
|---|---|---|---|---|---|---|---|
| | | | cuts, cracks, or dents | cuts, cracks, or dents | cuts, cracks, or dents | cuts, cracks, or dents | cuts, cracks, or dents |
| Appearance of Capsule Contents | Light yellow to tan powder | | Light yellow powder | Light yellow powder | Light yellow powder | Light yellow powder | Light yellow powder |
| Compound 1 | % Label Claim | 90.0-110.0% | 93.4% | 108.7% | 97.5% | 102.2% | 101.1% |
| | Degradation Products by HPLC | Any single unspecified ≥0.05% | | | | | |
| | Compound 2 | ≤0.20% area | None Detected | None Detected | None Detected | None Detected | None Detected |
| | Total Degradation Products | ≤1.0% | 0.0% | 0.0% | 0.0% | 0.0% | 0.0% |

| | Dissolution | Q = 80%, 30 min | Min | % | Min | % | Min | % | Min | % | Min | % |
|---|---|---|---|---|---|---|---|---|---|---|---|---|
| | | | 15 | 92 | 15 | 98 | 15 | 98 | 15 | 98 | 15 | 98 |
| | | | 30 | 96 | 30 | 99 | 30 | 99 | 30 | 99 | 30 | 99 |
| | | | 45 | 94 | 45 | 99 | 45 | 100 | 45 | 99 | 45 | 100 |
| | | | 60 | 99 | 60 | 99 | 60 | 100 | 60 | 100 | 60 | 100 |

| | | | | | | | |
|---|---|---|---|---|---|---|---|
| Ceftibuten | % Label Claim | 90.0-110.0% | 92.2% | 101.6% | 100.8% | 102.9% | 107.2% |
| | Degradation Products by HPLC | Any single unspecified ≥0.05% | | | | | |
| | Impurity 14 (Decarboxyl) | TBD | 0.21% | 0.37% | 0.16% | 0.27% | 0.28% |
| | Total Degradation Products | Report Results | 0.2% | 0.4% | 0.2% | 0.3% | 0.3% |

| | Dissolution | Q = 80%, 60 min | Min | % | Min | % | Min | % | Min | % | Min | % |
|---|---|---|---|---|---|---|---|---|---|---|---|---|
| | | | 15 | 96 | 15 | 102 | 15 | 99 | 15 | 99 | 15 | 99 |
| | | | 30 | 96 | 30 | 102 | 30 | 99 | 30 | 100 | 30 | 100 |
| | | | 45 | 98 | 45 | 102 | 45 | 100 | 45 | 100 | 45 | 100 |
| | | | 60 | 100 | 60 | 101 | 60 | 100 | 60 | 100 | 60 | 100 |

TABLE 18b

Summary of 25° C. Stability Data for 200 mg/200 mg FDC capsules of Ceftibuten-Compound 1 Citrate Coordination Complex (T = 6 months to 24 months)

| Attribute (Test Method) | Specification | | Testing Interval 6 Months | 9 Months | 12 Months | 18 Months | 24 Months |
|---|---|---|---|---|---|---|---|
| Capsule Appearance | White opaque hard capsule with no holes, cuts, cracks, or dents | | White opaque hard capsule with no holes, cuts, cracks, or dents | White opaque hard capsule with no holes, cuts, cracks, or dents | White opaque hard capsule with no holes, cuts, cracks, or dents | White opaque hard capsule with no holes, cuts, cracks, or dents | White opaque hard capsule with no holes, cuts, cracks, or dents |
| Appearance of Capsule Contents | Light yellow to tan powder | | Light yellow powder | Light yellow powder | Light yellow powder | Light yellow powder | Light yellow powder |
| Compound 1 | % Label Claim | 90.0-110.0% | 97.0% | 98.9% | 99.4% | 97.8% | 102.8% |
| | Degradation Products by HPLC | Any single unspecified ≥0.05% | | | | | |

TABLE 18b-continued

Summary of 25° C. Stability Data for 200 mg/200 mg FDC capsules of Ceftibuten-Compound 1 Citrate Coordination Complex (T = 6 months to 24 months)

| Attribute (Test Method) | | Specification | Testing Interval 6 Months | | 9 Months | | 12 Months | | 18 Months | | 24 Months | |
|---|---|---|---|---|---|---|---|---|---|---|---|---|
| | Compound 2 | ≤0.20% area | None Detected | | None Detected | | None Detected | | None Detected | | None Detected | |
| | Total Degradation Products | ≤1.0% | 0.0% | | 0.0% | | 0.0% | | 0.0% | | 0.0% | |
| | Dissolution | Q = 80%, 30 min | Min | % | Min | % | Min | % | Min | % | Min | % |
| | | | 15 | 103 | 15 | 97 | 15 | 95 | 15 | 91 | 15 | 97 |
| | | | 30 | 98 | 30 | 99 | 30 | 97 | 30 | 92 | 30 | 99 |
| | | | 45 | 99 | 45 | 100 | 45 | 97 | 45 | 92 | 45 | 99 |
| | | | 60 | 101 | 60 | 99 | 60 | 97 | 60 | 92 | 60 | 100 |
| Ceftibuten | % Label Claim | 90.0-110.0% | 100.8% | | 101.7% | | 103.3% | | 97.2% | | 94.5% | |
| | Degradation Products by HPLC | Any single unspecified ≥0.05% | | | | | | | | | | |
| | Impurity 14 (Decarboxyl) | TBD | 0.39% | | 0.32% | | 0.40% | | 0.51% | | 0.68% | |
| | Total Degradation Products | Report Results | 0.4% | | 0.3% | | 0.4% | | 0.5% | | 0.7% | |
| | Dissolution | Q = 80%, 60 min | Min | % | Min | % | Min | % | Min | % | Min | % |
| | | | 15 | 100 | 15 | 99 | 15 | 105 | 15 | 103 | 15 | 106 |
| | | | 30 | 100 | 30 | 100 | 30 | 105 | 30 | 103 | 30 | 106 |
| | | | 45 | 100 | 45 | 100 | 45 | 105 | 45 | 103 | 45 | 106 |
| | | | 60 | 100 | 60 | 99 | 60 | 105 | 60 | 103 | 60 | 106 |

TABLE 19a

Summary of 2-8° C. Stability Data for 200 mg/200 mg FDC capsules of Ceftibuten-Compound 1 Citrate Coordination Complex (T = 0 to 9 months)

| Attribute (Test Method) | | Specification | Testing Interval T = 0 | | 6 Months | | 9 Months | |
|---|---|---|---|---|---|---|---|---|
| Capsule Appearance | | White opaque hard capsule with no holes, cuts, cracks, or dents | White opaque hard capsule with no holes, cuts, cracks, or dents | | White opaque hard capsule with no holes, cuts, cracks, or dents | | White opaque hard capsule with no holes, cuts, cracks, or dents | |
| Appearance of Capsule Contents | | Light yellow to tan powder | Light yellow powder | | Light yellow powder | | Light yellow powder | |
| Compound 1 | % Label Claim | 90.0-110.0% | 93.4% | | 107.8% | | 103.8% | |
| | Degradation Products by HPLC | Any single unspecified ≥0.05% | | | | | | |
| | Compound 2 | ≤0.20% area | None Detected | | None Detected | | None Detected | |
| | Total Degradation Products | ≤1.0% | 0.0% | | 0.0% | | 0.0% | |
| | Dissolution | Q = 80%, 30 min | Min | % | Min | % | Min | % |
| | | | 15 | 92 | 15 | 96 | 15 | 96 |
| | | | 30 | 96 | 30 | 97 | 30 | 97 |
| | | | 45 | 94 | 45 | 97 | 45 | 98 |
| | | | 60 | 99 | 60 | 97 | 60 | 98 |
| Ceftibuten | % Label Claim | 90.0-110.0% | 92.2% | | 105.0% | | 107.2% | |

TABLE 19a-continued

Summary of 2-8° C. Stability Data for 200 mg/200 mg FDC capsules of Ceftibuten-Compound 1 Citrate Coordination Complex (T = 0 to 9 months)

| Attribute (Test Method) | Specification | | Testing Interval T = 0 | | 6 Months | | 9 Months | |
|---|---|---|---|---|---|---|---|---|
| | Degradation Products by HPLC | Any single unspecified ≥0.05% | | | | | | |
| | Impurity 14 (Decarboxyl) | TBD | 0.21% | | ND | | 0.09% | |
| | Total Degradation Products | Report Results | 0.2% | | NA | | 0.1% | |
| | Dissolution (Normalized) | Q = 80%, 60 min | Min | % | Min | % | Min | % |
| | | | 15 | 96 | 15 | 101 | 15 | 100 |
| | | | 30 | 96 | 30 | 101 | 30 | 101 |
| | | | 45 | 98 | 45 | 101 | 45 | 101 |
| | | | 60 | 100 | 60 | 101 | 60 | 101 |

TABLE 19b

Summary of 2-8° C. Stability Data for 200 mg/200 mg FDC capsules of Ceftibuten-Compound 1 Citrate Coordination Complex (T = 12 months to 24 months)

| Attribute (Test Method) | Specification | | Testing Interval 12 Months | | 18 Months | | 24 Months | |
|---|---|---|---|---|---|---|---|---|
| Capsule Appearance | White opaque hard capsule with no holes, cuts, cracks, or dents | | White opaque hard capsule with no holes, cuts, cracks, or dents | | White opaque hard capsule with no holes, cuts, cracks, or dents | | White opaque hard capsule with no holes, cuts, cracks, or dents | |
| Appearance of Capsule Contents | Light yellow to tan powder | | Light yellow powder | | Light yellow powder | | Light yellow powder | |
| Compound 1 | % Label Claim | 90.0-110.0% | 102.8% | | 97.2% | | 103.3% | |
| | Degradation Products by HPLC | Any single unspecified ≥0.05% | | | | | | |
| | Compound 2 | ≤0.20% area | None Detected | | None Detected | | None Detected | |
| | Total Degradation Products | ≤1.0% | 0.0% | | 0.0% | | 0.0% | |
| | Dissolution | Q = 80%, 30 min | Min | % | Min | % | Min | % |
| | | | 15 | 96 | 15 | 91 | 15 | 95 |
| | | | 30 | 96 | 30 | 93 | 30 | 97 |
| | | | 45 | 98 | 45 | 94 | 45 | 98 |
| | | | 60 | 98 | 60 | 93 | 60 | 98 |
| Ceftibuten | % Label Claim | 90.0-110.0% | 108.8% | | 98.9% | | 104.4% | |
| | Degradation Products by HPLC | Any single unspecified ≥0.05% | | | | | | |
| | Impurity 14 (Decarboxyl) | TBD | 0.07% | | 0.11% | | 0.12% | |
| | Total Degradation Products | Report Results | 0.1% | | 0.1% | | 0.1% | |
| | Dissolution (Normalized) | Q = 80%, 60 min | Min | % | Min | % | Min | % |
| | | | 15 | 101 | 15 | 108 | 15 | 108 |
| | | | 30 | 101 | 30 | 109 | 30 | 108 |
| | | | 45 | 101 | 45 | 109 | 45 | 108 |
| | | | 60 | 102 | 60 | 109 | 60 | 108 |

What is claimed:

1. A compound that is (R)-(2-(3-((((2-ethylbutanoyl)oxy)methoxy)carbonyl)-2-hydroxyphenyl)-1-propionamidoethyl)boronic acid citrate coordination complex:

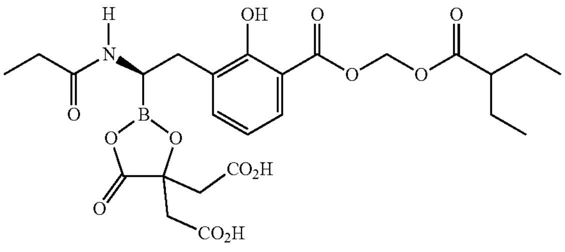
, or a pharmaceutically acceptable salt or solvate thereof.

2. The compound of claim 1, wherein the compound is:

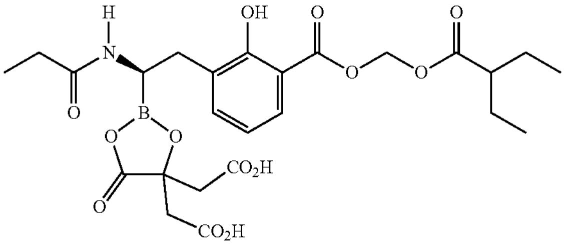
.

3. A crystalline form of a compound that is (R)-(2-(3-((((2-ethylbutanoyl)oxy)methoxy)carbonyl)-2-hydroxyphenyl)-1-propionamidoethyl)boronic acid citrate coordination complex:

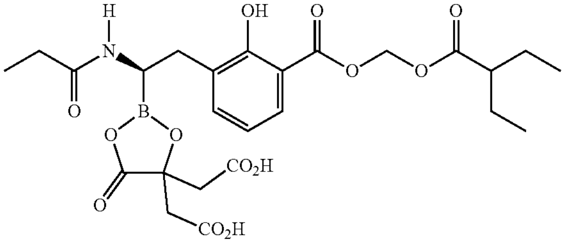
;

wherein the crystalline form has an X-ray powder diffraction (XRPD) pattern comprising characteristic peaks at 5.9°±0.1° 2θ, 9.5°±0.1° 2θ, 11.1°±0.1° 2θ, 11.9°±0.1° 2θ, and 13.9°±0.1° 2θ.

4. The crystalline form of claim 3, wherein the X-ray powder diffraction (XRPD) pattern further comprises characteristic peaks at 11.4°±0.1° 2θ, 13.3°±0.1° 2θ, 14.4°±0.1° 2θ, and 17.7°±0.1° 2θ.

5. The crystalline form of claim 4, wherein the X-ray powder diffraction (XRPD) pattern further comprises characteristic peaks at 8.1°±0.1° 2θ, 8.3°±0.1° 2θ, 11.5°±0.1° 2θ, and 17.2°±0.1° 2θ.

6. A crystalline form of a compound that is (R)-(2-(3-((((2-ethylbutanoyl)oxy)methoxy)carbonyl)-2-hydroxyphenyl)-1-propionamidoethyl)boronic acid citrate coordination complex:

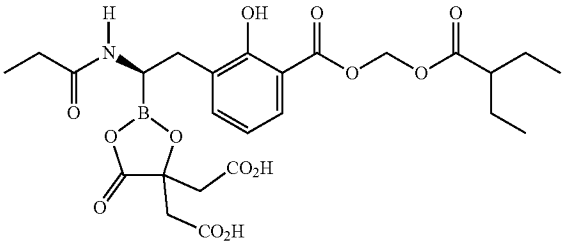
;

wherein the crystalline form has a DSC thermogram with an endotherm having an onset at about 143.7° C.

7. A crystalline form of a compound that is (R)-(2-(3-((((2-ethylbutanoyl)oxy)methoxy)carbonyl)-2-hydroxyphenyl)-1-propionamidoethyl)boronic acid citrate coordination complex:

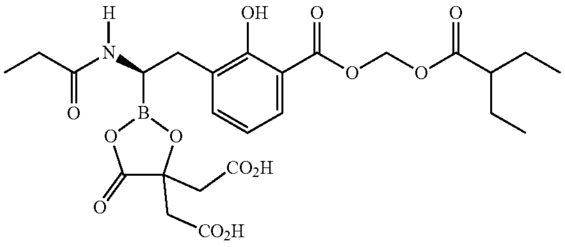
;

wherein the crystalline form has an X-ray powder diffraction (XRPD) pattern comprising characteristic peaks at 10.1°±0.1° 2θ and 12.7°±0.1° 2θ.

8. The crystalline form of claim 7, wherein the X-ray powder diffraction (XRPD) pattern further comprises a characteristic peak at 16.3°±0.1° 2θ.

9. The crystalline form of claim 8, wherein the X-ray powder diffraction (XRPD) pattern further comprises a characteristic peak at 18.1°±0.1° 2θ.

10. A pharmaceutical composition comprising:

(i) a compound that is (R)-(2-(3-((((2-ethylbutanoyl)oxy)methoxy)carbonyl)-2-hydroxyphenyl)-1-propionamidoethyl)boronic acid citrate coordination complex:

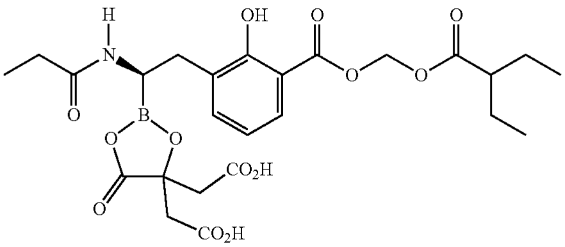
, or a pharmaceutically acceptable salt or solvate thereof; and (ii) ceftibuten.

11. The pharmaceutical composition of claim 10, wherein ceftibuten is in the form of ceftibuten dihydrate.

12. The pharmaceutical composition of claim 10, wherein the compound is:

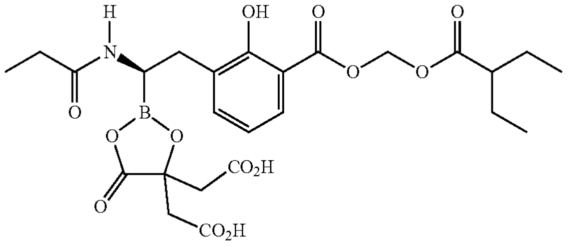
.

13. A pharmaceutical composition comprising:

(i) a crystalline form of a compound that is (R)-(2-(3-((((2-ethylbutanoyl)oxy)methoxy)carbonyl)-2-hydroxyphenyl)-1-propionamidoethyl)boronic acid citrate coordination complex:

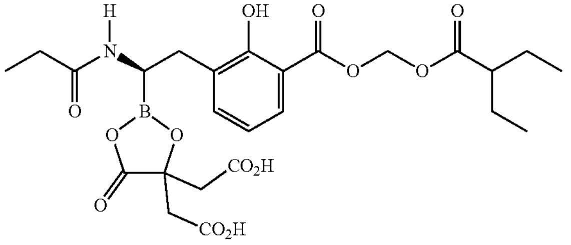
, or a pharmaceutically acceptable salt or solvate thereof; and (ii) ceftibuten.

14. The pharmaceutical composition of claim 13, wherein ceftibuten is in the form of ceftibuten dihydrate.

15. The pharmaceutical composition of claim 13, wherein the compound is:

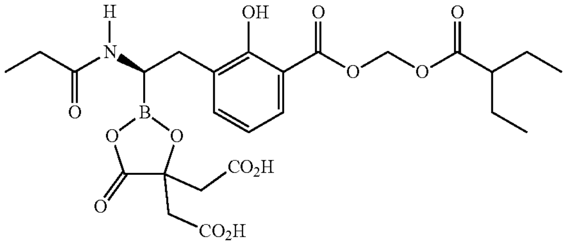
.

16. The pharmaceutical composition of claim 15, wherein the crystalline form has an X-ray powder diffraction (XRPD) pattern comprising characteristic peaks at 5.9°±0.1° 2θ, 9.5°±0.1° 2θ, 11.1°±0.1° 2θ, 11.9°±0.1° 2θ, and 13.9°±0.1° 2θ.

17. The pharmaceutical composition of claim 16, wherein the X-ray powder diffraction (XRPD) pattern further comprises characteristic peaks at 11.4°±0.1° 2θ, 13.3°±0.1° 2θ, 14.4°±0.1° 2θ, and 17.7°±0.1° 2θ.

18. The pharmaceutical composition of claim 17, wherein the X-ray powder diffraction (XRPD) pattern further comprises characteristic peaks at 8.1°±0.1° 2θ, 8.3°±0.1° 2θ, 11.5°±0.1° 2θ, and 17.2°±0.1° 2θ.

19. The pharmaceutical composition of claim 15, wherein the crystalline form has an X-ray powder diffraction (XRPD) pattern comprising characteristic peaks at 10.1°±0.1° 2θ and 12.7°±0.1° 2θ.

20. The pharmaceutical composition of claim 19, wherein the X-ray powder diffraction (XRPD) pattern further comprises a characteristic peak at 16.3°±0.1° 2θ.

21. The pharmaceutical composition of claim 20, wherein the X-ray powder diffraction (XRPD) pattern further comprises a characteristic peak at 18.1°±0.1° 2θ.

22. The pharmaceutical composition of claim 11, wherein the pharmaceutical composition comprises the compound and ceftibuten dihydrate in a ratio adjusted to correspond to between about 1:1 and about 1:4 of

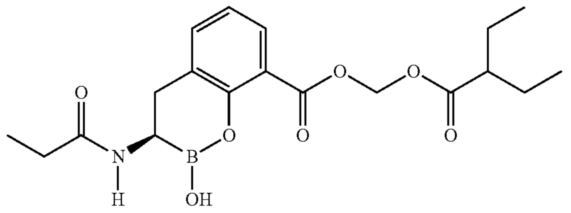 [SMILES: CCC(=O)N[C@H]1Cc2cccc(C(=O)OCOC(=O)C(CC)CC)c2OB1O]

and ceftibuten.

* * * * *